US009474742B2

United States Patent
Wiles et al.

(10) Patent No.: US 9,474,742 B2
(45) Date of Patent: *Oct. 25, 2016

(54) SUBSTITUTED ALIPHANES, CYCLOPHANES, HETERAPHANES, HETEROPHANES, HETERO-HETERAPHANES AND METALLOCENES USEFUL FOR TREATING HCV INFECTIONS

(71) Applicant: Achillion Pharmaceuticals, Inc, New Haven, CT (US)

(72) Inventors: Jason Allan Wiles, Hamden, CT (US); Qiuping Wang, Bethany, CT (US); Akihiro Hashimoto, Branford, CT (US); Godwin Pais, Hamden, CT (US); Xiangzhu Wang, Madison, CT (US); Venkat Gadhachanda, Hamden, CT (US); Avinash Phadke, Branford, CT (US); Milind Deshpande, Madison, CT (US); Dawei Chen, Middletown, CT (US)

(73) Assignee: Achillion Pharmaceuticals, Inc., New Haven, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/972,913

(22) Filed: Dec. 17, 2015

(65) Prior Publication Data

US 2016/0113907 A1     Apr. 28, 2016

Related U.S. Application Data

(63) Continuation of application No. 14/328,312, filed on Jul. 10, 2014, now Pat. No. 9,273,082, which is a continuation of application No. 13/482,558, filed on May 29, 2012, now Pat. No. 8,809,313.

(60) Provisional application No. 61/567,216, filed on Dec. 6, 2011, provisional application No. 61/504,905, filed on Jul. 6, 2011, provisional application No. 61/490,881, filed on May 27, 2011.

(51) Int. Cl.
A61K 31/4184     (2006.01)
A61K 9/20         (2006.01)
(Continued)

(52) U.S. Cl.
CPC ......... *A61K 31/4184* (2013.01); *A61K 9/0053* (2013.01); *A61K 9/20* (2013.01); *A61K 31/4178* (2013.01); *A61K 31/422* (2013.01); *A61K 31/427* (2013.01); *A61K 31/439* (2013.01); *A61K 31/454* (2013.01); *A61K 31/496* (2013.01); *A61K 31/555* (2013.01); *A61K 45/06* (2013.01); *C07D 209/42* (2013.01); *C07D 401/14* (2013.01); *C07D 403/04* (2013.01); *C07D 403/14* (2013.01); *C07D 413/14* (2013.01); *C07D 417/14* (2013.01); *C07D 453/06* (2013.01); *C07D 471/08* (2013.01);
(Continued)

(58) Field of Classification Search
None
See application file for complete search history.

(56) References Cited

U.S. PATENT DOCUMENTS 5,147,882 A    9/1992  Psiorz et al.
6,448,392 B1   9/2002  Hostetler et al.
(Continued)

FOREIGN PATENT DOCUMENTS

WO    2008021927 A2    2/2008
WO    2010059937 A1    5/2010
(Continued)

OTHER PUBLICATIONS

Shafer, S., Kolkhof, P. Failure is an option: learning from unsuccessful proof-of-concept trials. Drug Discovery Today. Nov. 2008, 13, 913-916.*

(Continued)

*Primary Examiner* — Rebecca Anderson
*Assistant Examiner* — Po-Chih Chen
(74) *Attorney, Agent, or Firm* — Knowles IP Strategies, LLC

(57) ABSTRACT

The present disclosure provides substituted aliphanes, cyclophanes, heteraphanes, heterophanes, hetero-heteraphanes and metallocenes, of Formula I D-M-D     (Formula I)

useful as antiviral agents. In certain embodiments disclosed herein M is a group —P-A-P— where A is

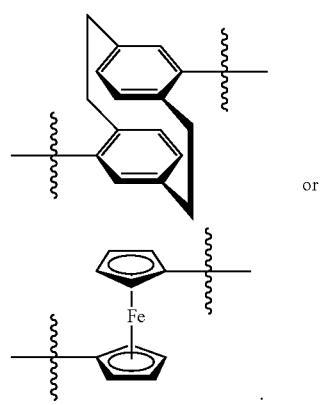

Certain substituted aliphanes, cyclophanes, heteraphanes, heterophanes, hetero-heteraphanes and metallocenes disclosed herein are potent and/or selective inhibitors of viral replication, particularly Hepatitis C virus replication. Pharmaceutical compositions/and combinations containing one or more substituted aliphanes, cyclophanes, heteraphanes, heterophanes, hetero-heteraphanes and metallocenes and a pharmaceutically acceptable carrier are also provided by this disclosure. Methods for treating viral infections, including Hepatitis C viral infections are provided by the disclosure.

41 Claims, No Drawings

(51) Int. Cl.
A61K 9/00 (2006.01)
A61K 45/06 (2006.01)
C07D 403/04 (2006.01)
C07D 401/14 (2006.01)
C07D 403/14 (2006.01)
C07D 413/14 (2006.01)
C07D 417/14 (2006.01)
C07D 471/08 (2006.01)
C07D 491/10 (2006.01)
C07D 519/00 (2006.01)
A61K 31/4178 (2006.01)
A61K 31/439 (2006.01)
A61K 31/496 (2006.01)
A61K 31/555 (2006.01)
C07F 17/02 (2006.01)
A61K 31/422 (2006.01)
A61K 31/427 (2006.01)
A61K 31/454 (2006.01)
C07D 453/06 (2006.01)
C07D 491/113 (2006.01)
C07F 15/02 (2006.01)
C07D 209/42 (2006.01)
C07F 5/02 (2006.01)

(52) U.S. Cl.
CPC ......... *C07D 491/10* (2013.01); *C07D 491/113* (2013.01); *C07D 519/00* (2013.01); *C07F 5/025* (2013.01); *C07F 15/02* (2013.01); *C07F 17/02* (2013.01)

(56) References Cited

U.S. PATENT DOCUMENTS

| 6,599,887 | B2 | 7/2003 | Hostetler et al. |
| 7,749,983 | B2 | 7/2010 | Hostetler et al. |
| 7,906,619 | B2 | 3/2011 | Phadke et al. |
| 8,088,806 | B2 | 1/2012 | Zhang et al. |
| 8,809,313 | B2 | 8/2014 | Wiles et al. |
| 9,273,082 | B2 | 3/2016 | Wiles et al. |
| 2008/0050336 | A1 | 2/2008 | Bachand et al. |
| 2009/0041720 | A1 | 2/2009 | Wang et al. |
| 2009/0082261 | A1 | 3/2009 | Chen et al. |
| 2010/0152103 | A1 | 6/2010 | Phadke et al. |
| 2010/0158862 | A1 | 6/2010 | Kim et al. |
| 2010/0216725 | A1 | 8/2010 | Phadke et al. |
| 2010/0310512 | A1 | 12/2010 | Guo et al. |

FOREIGN PATENT DOCUMENTS

| WO | 2010068760 A2 | 6/2010 |
| WO | 2010111483 A1 | 9/2010 |
| WO | 2010132601 A1 | 11/2010 |
| WO | 2011031904 A1 | 3/2011 |
| WO | 2011050146 A1 | 4/2011 |
| WO | 2011091532 A1 | 8/2011 |
| WO | 2012166716 A2 | 6/2012 |

OTHER PUBLICATIONS

Horig, H., Pullman, W. From bench to clinic and back: Perspective on the 1st IQPC Translational Research conference. Journal of Translational Medicine. Dec. 2004, 2, 44.*
Lemm et al., Identification of Hepatitis C Virus NS5A Inhibitors. Journal of Virology 2010, 84, 428-491.*
Belda et al., Small molecule inhibitors of the hepatitis C virus-encoded NS5A protein. Virus Research 2012, 170, 1-14.*
Belda et al., "Small Molecule Inhibitors of the Hepatitis C Virus-Encoded NS5A Protein", Virus Research; vol. 170, 2012, pp. 1-14.
Horig et al., "From Bench to Clinic and Back: Perspective on the 1st IQPC Translational Research Conference"; Journal of Translational Medicine; vol. 2, No. 44; 2004; 8 Pages.
International Preliminary Report on Patentability for International Application No. PCT/US2012/039835; International Filing Date: May 29, 2012; Date of Mailing: Dec. 12, 2013; 7 Pages.
International Search Report for the International Searching Authority Application No. PCT/US2012/039835; International Filing Date: May 29, 2012; Date of Mailing: Dec. 6, 2012; 7 Pages.
Lemm et al., "Identification of Hepatitis C Virus NS5A Inhibitors", Journal of Virology; vol. 84, No. 1; 2010; pp. 482-491.
Schafer et al., "Failure is an Option: Learning from Unsuccessful Proof-of-Concept Trials", Drug Discovery Today; vol. 13, Nos: 21/22; 2008; pp. 913-916.
Written Opinion of the International Searching Authority Application No. PCT/US2012/039835; International Filing Date: May 29, 2012; Date of Mailing: Dec. 6, 2012; 5 Pages.

\* cited by examiner

SUBSTITUTED ALIPHANES, CYCLOPHANES, HETERAPHANES, HETEROPHANES, HETERO-HETERAPHANES AND METALLOCENES USEFUL FOR TREATING HCV INFECTIONS

PRIORITY INFORMATION

This application is a continuation of U.S. application Ser. No. 14/328,312, which is a continuation of U.S. application Ser. No. 13/482,558, which claims priority from U.S. Provisional Application Nos. 61/490,881 filed May 27, 2011, 61/504,905, filed Jul. 6, 2011, and 61/567,216, filed Dec. 6, 2011 all of which are hereby incorporated by reference in their entirety.

FIELD OF THE DISCLOSURE

The present disclosure provides substituted aliphanes, cyclophanes, heteraphanes, heterophanes, hetero-heteraphanes and metallocenes, useful as antiviral agents. Certain substituted aliphanes, cyclophanes, heteraphanes, heterophanes, hetero-heteraphanes and metallocenes disclosed herein are potent and/or selective inhibitors of viral replication, particularly Hepatitis C virus replication. Pharmaceutical compositions/and combinations containing one or more substituted aliphanes, cyclophanes, heteraphanes, heterophanes, hetero-heteraphanes and metallocenes and a pharmaceutically acceptable carrier are also provided by this disclosure. Methods for treating viral infections, including Hepatitis C viral infections are provided by the disclosure.

BACKGROUND

An estimated 3% of the world's population is infected with the hepatitis C virus. Of those exposed to HCV, 80% to 85% become chronically infected, at least 30% develop cirrhosis of the liver and 1-4% develop hepatocellular carcinoma. Hepatitis C Virus (HCV) is one of the most prevalent causes of chronic liver disease in the United States, reportedly accounting for about 15 percent of acute viral hepatitis, 60 to 70 percent of chronic hepatitis, and up to 50 percent of cirrhosis, end-stage liver disease, and liver cancer. Chronic HCV infection is the most common cause of liver transplantation in the U.S., Australia, and most of Europe. Hepatitis C causes an estimated 10,000 to 12,000 deaths annually in the United States. While the acute phase of HCV infection is usually associated with mild symptoms, some evidence suggests that only about 15% to 20% of infected people will spontaneously clear HCV.

HCV is an enveloped, single-stranded RNA virus that contains a positive-stranded genome of about 9.6 kb. HCV is classified as a member of the Hepacivirus genus of the family Flaviviridae. At least 4 strains of HCV, GT-1-GT-4, have been characterized.

The HCV lifecycle includes entry into host cells; translation of the HCV genome, polyprotein processing, and replicase complex assembly; RNA replication, and virion assembly and release. Translation of the HCV RNA genome yields a more than 3000 amino acid long polyprotein that is processed by at least two cellular and two viral proteases. The HCV polyprotein is:

NH2-C-E1-E2-p7-NS2-NS3-NS4A-NS4B-NS5A-NS5B-COOH.

The cellular signal peptidase and signal peptide peptidase have been reported to be responsible for cleavage of the N-terminal third of the polyprotein (C-E1-E2-p7) from the nonstructural proteins (NS2-NS3-NS4A-NS4B-NS5A-NS5B). The NS2-NS3 protease mediates a first cis cleavage at the NS2-NS3 site. The NS3-NS4A protease then mediates a second cis-cleavage at the NS3-NS4A junction. The NS3-NS4A complex then cleaves at three downstream sites to separate the remaining nonstructural proteins. Accurate processing of the polyprotein is asserted to be essential for forming an active HCV replicase complex.

Once the polyprotein has been cleaved, the replicase complex comprising at least the NS3-NS5B nonstructural proteins assembles. The replicase complex is cytoplasmic and membrane-associated. Major enzymatic activities in the replicase complex include serine protease activity and NTPase helicase activity in NS3, and RNA-dependent RNA polymerase activity of NS5B. In the RNA replication process, a complementary negative strand copy of the genomic RNA is produced. The negative strand copy is used as a template to synthesize additional positive strand genomic RNAs that may participate in translation, replication, packaging, or any combination thereof to produce progeny virus. Assembly of a functional replicase complex has been described as a component of the HCV replication mechanism. U.S. Provisional Application No. 60/669,872 "Pharmaceutical Compositions and Methods of Inhibiting HCV Replication" filed Apr. 11, 2005, is hereby incorporated by reference in its entirety for its disclosure related to assembly of the replicase complex.

Current treatment of hepatitis C infection typically includes administration of an interferon, such as pegylated interferon (IFN), in combination with ribavirin. The success of current therapies as measured by sustained virologic response (SVR) depends on the strain of HCV with which the patient is infected and the patient's adherence to the treatment regimen. Only 50% of patients infected with HCV strain GT-1 exhibit a sustained virological response. Direct acting antiviral agents such as ACH-1625, telaprevir, BMS-790052, and BMS-650032 are in clinical development for treatment of chronic HCV. Due to lack of effective therapies for treatment for certain HCV strains and the high mutation rate of HCV, new therapies are needed. The present disclosure fulfills this need and provides additional advantages, which are described herein.

SUMMARY

Substituted aliphanes, cyclophanes, heteraphanes, heterophanes, hetero-heteraphanes and metallocenes of Formula I are provided herein. The compounds of Formula I provided in this disclosure posses antiviral activity.

The disclosure provides compounds of Formula I that are potent and/or selective inhibitors of Hepatitis C virus replication. Without being bound to any particular theory it is believed the present compounds are potent and selective inhibitors of HCV NS5a. Pharmaceutical compositions containing one or more compounds of Formula I, or a salt of such compounds, and one or more pharmaceutically acceptable carriers are also provided herein. Pharmaceutical combinations containing one or more compounds of Formula I, or a salt of such compounds, at least one additional active agent, and one or more pharmaceutically acceptable carriers are also provided herein.

Also disclosed are methods of treating patients suffering from certain viral infections, particularly HCV infections, by providing to such patients an amount of a compound of Formula I effective to reduce signs or symptoms of the viral infection. Methods of treatment include providing a compound of Formula I as a single active agent or providing a compound of Formula I in combination with one or more other therapeutic active agents.

In a first aspect the disclosure includes compounds of Formula I $$D\text{-}M\text{-}D \qquad \text{(Formula I)}$$

or a pharmaceutically acceptable salt thereof.

Within Formula I, the variables D and M carry the following definitions.

D is T-R— where M is covalently bound to R.

M is —P-A-P—.

P is -J-W— where J is covalently bound to R and W is covalently bound to A, or

P is -J- where J is covalently bound to R and A.

J is independently chosen at each occurrence and is $J^i$ where i is an integer from 1 to 2.

T is independently chosen at each occurrence and is $T^k$ where k is an integer from 1 to 2; $T^1$ is —Y—Z, where Y is covalently bound to R and Y is a bond, $C_1$-$C_4$alkylene optionally substituted with oxo; and Z is a 5 or 6-membered heterocyclic group, each of which $T^1$ is substituted with (i) at least one substituent selected from —(C=O)OH, —(C=O)NH$_2$, —(C=O)H, —$C_1$-$C_4$alkoxy, $C_2$-$C_4$alkanoyl, $C_1$-$C_4$alkylester, $C_1$-$C_4$alkenylester, mono- or di-$C_1$-$C_4$alkylcarboxamide and (ii) optionally substituted with one or more substituents independently chosen from halogen, hydroxyl, $C_1$-$C_2$alkyl, and $C_1$-$C_2$alkoxy; and $T^2$ is independently chosen at each occurrence from $C_2$-$C_6$alkanoyl, $C_1$-$C_6$alkylester, $C_1$-$C_6$alkenylester, $C_1$-$C_6$alkylsulfonamide, $C_1$-$C_6$alkylsulfonyl, $C_2$-$C_6$alkanoyl substituted with mono- or di-$C_1$-$C_6$hydrocarbylcarbamate, $C_2$-$C_6$alkanoyl substituted with urea or mono- or di-$C_1$-$C_6$alkylurea, and $C_2$-$C_6$alkanoyl substituted with mono- or di-$C_1$-$C_6$alkylcarboxamide, each of which T is optionally substituted with 1 or more substituents independently chosen from amino, cyano, hydroxyl, halogen, ($C_1$-$C_4$alkoxy) $C_0$-$C_4$alkyl, (mono- and di-$C_1$-$C_4$alkylamino)$C_0$-$C_4$alkyl, $C_1$-$C_6$alkyl, ($C_1$-$C_4$thioalkyl)$C_0$-$C_4$alkyl, $C_3$-$C_7$cycloalkyl, phenyl, $C_1$-$C_4$haloalkyl, and $C_1$-$C_4$haloalkoxy;

R is independently chosen at each occurrence from (a) 4- to 6-membered rings containing one or two nitrogen atoms with remaining ring atoms being carbon, which R is saturated or contains 1 unsaturated bond and is optionally bridged with an methylene or ethylene bridge, fused to a phenyl or 5- to 6-membered heteroaryl ring; and (b) 6- to 10-membered fused or spiro bicyclic ring systems containing one or two nitrogen atoms with remaining ring atoms being carbon, which 6- to 10-membered bicyclic ring is saturated or contains 1 unsaturated bond; each R is optionally substituted with one or more substituents independently chosen from cyano, hydroxyl, halogen, $C_1$-$C_2$alkyl, $C_1$-$C_2$alkoxy, $C_1$-$C_2$haloalkyl, $C_1$-$C_2$haloalkyl, $C_1$-$C_2$haloalkylene, and $C_1$-$C_2$alkylsulfonyl.

$J^1$ is phenyl or a 5- to 6-membered heteroaryl group containing 1 to 3 heteroatoms independently chosen from N, O, and S, where each $J^1$ is optionally substituted with one or more substituents independently chosen from amino, cyano, hydroxyl, halogen, $C_1$-$C_4$alkyl, $C_1$-$C_4$alkoxy, mono- and di-$C_1$-$C_4$alkylamino, $C_1$-$C_2$haloalkyl, and $C_1$-$C_2$haloalkoxy.

$J^2$ is an 8- to 10-membered heteroaryl group containing 1 to 4 heteroatoms independently chosen from N, O, and S, wherein $J^2$ is optionally substituted with one or more substituents independently chosen from amino, cyano, hydroxyl, halogen, $C_1$-$C_4$alkyl, $C_1$-$C_4$alkoxy, mono- and di-$C_1$-$C_4$alkylamino, $C_1$-$C_2$haloalkyl, and $C_1$-$C_2$haloalkoxy.

W is independently chosen at each occurrence and is a phenyl, pyridyl or alkynyl group, optionally substituted with one or more substituents independently chosen from amino, cyano, hydroxyl, halogen, $C_1$-$C_4$alkyl, $C_1$-$C_4$alkoxy, mono- and di-$C_1$-$C_4$alkylamino, $C_1$-$C_2$haloalkyl, and $C_1$-$C_2$haloalkoxy.

A is [j.k]-cyclophane, [j.k]-hetera-phane, [j.k]-hetero-phane, [j.k]-hetero-hetera-phane, or [j.k]-aliphane; where j is an integer from 1 to 4, k is an integer from 0 to 4, the difference between j and k is not more than 2, and each j and k linker optionally contains a heteroatom selected from N, O, and S, and is optionally substituted with 1 oxo group, and one or more substituents independently chosen from halogen, hydroxy, amino, $C_1$-$C_2$alkyl, and $C_1$-$C_2$alkoxy; or A is a [j.k.j'.k']-cyclophane, where j, j', k, and k' are integers from 1 to 4, the difference between j and k or k' is not more than 2, the difference between j' and k or k' is not more than 2, and each j, j', k, and k' linker optionally contains a heteroatom selected from N, O, and S, and is optionally substituted with 1 oxo group, and one or more substituents independently chosen from halogen, hydroxy, amino, $C_1$-$C_2$alkyl, and $C_1$-$C_2$alkoxy;

or

A is a group of the formula

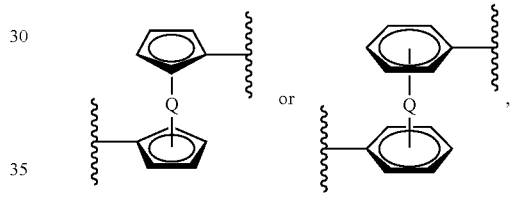

wherein Q is a neutral or cationic metal, each of which A is optionally substituted with one or more substituents independently chosen from halogen, $C_1$-$C_2$alkyl, and $C_1$-$C_2$alkoxy. In certain embodiments Q is chosen from Fe, Co, Cr, Ni, V, Li, Rb, and K; or A is a group of the formula

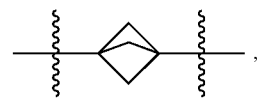 [SMILES: *C12CC(*)(C1)C2]

which A is optionally substituted with one or more substituents independently chosen from halogen, $C_1$-$C_2$alkyl, and $C_1$-$C_2$alkoxy.

Pharmaceutical compositions and combinations containing a compound of Formula I, together with a pharmaceutically acceptable carrier are provided by the disclosure. The compositions and combinations provided by this disclosure may include a compound of Formula I as the only active agent or may include one ore more additional active agents. In certain embodiments the additional active agent is an NS3a protease inhibitor. This disclosure also includes a method of treating hepatitis C infection in a patient, comprising providing a therapeutically effective amount of one or more compounds of Formula I to the patient. The compound of Formula I may be provided as the only active agent or may be provided together with one or more additional active agents such as an NS3a protease inhibitor.

Certain compounds of Formula I disclosed herein exhibit good activity in an HCV replication assay, such as the HCV replicon assay set forth in Example 9, which follows. Preferred compounds of Formula I exhibit an $EC_{50}$ of about 10 micromolar or less, or more preferably an $EC_{50}$ of about 1 micromolar or less; or still more preferably an $EC_{50}$ of about 100 nanomolar or less in an HCV replicon replication assay.

DETAILED DESCRIPTION

Chemical Description and Terminology

Prior to setting forth the invention in detail, it may be helpful to provide definitions of certain terms to be used in this disclosure. Compounds are described using standard nomenclature. Unless defined otherwise, all technical and scientific terms used herein have the same meaning as is commonly understood by one of skill in the art to which this invention belongs. Unless clearly contraindicated by the context each compound name includes the free acid or free base form of the compound as well as all pharmaceutically acceptable salts of the compound.

The term "compounds of Formula I" encompasses all compounds that satisfy Formula I, including any enantiomers, racemates and stereoisomers, as well as all pharmaceutically acceptable salts of such compounds. The phrase "a compound of Formula I" includes all subgeneric groups of Formula I, and also includes pharmaceutically acceptable salts of a compound of Formula I, unless clearly contraindicated by the context in which this phrase is used.

"Formula II" encompasses all compounds that satisfy Formula II, including any enantiomers, racemates and stereoisomers, as well as all pharmaceutically acceptable salts of such compounds. The phrase "a compound of Formula II" includes all sub generic groups of Formula II, and also includes pharmaceutically acceptable salts of a compound of Formula II, unless clearly contraindicated by the context in which this phrase is used.

The terms "a" and "a" do not denote a limitation of quantity, but rather denote the presence of at least one of the referenced item. The term "or" means "and/or". The open-ended transitional phrase "comprising" encompasses the intermediate transitional phrase "consisting essentially of" and the close-ended phrase "consisting of." Claims reciting one of these three transitional phrases, or with an alternate transitional phrase such as "containing" or "including" can be written with any other transitional phrase unless clearly precluded by the context or art. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein. Unless defined otherwise, technical and scientific terms used herein have the same meaning as is commonly understood by one of skill in the art to which this invention belongs.

An "active agent" means a compound (including a compound disclosed herein), element, or mixture that when administered to a patient, alone or in combination with another compound, element, or mixture, confers, directly or indirectly, a physiological effect on the patient. The indirect physiological effect may occur via a metabolite or other indirect mechanism.

A dash ("-") that is not between two letters or symbols is used to indicate a point of attachment for a substituent. For example, —(C=O)NH2 is attached through carbon of the keto (C=O) group.

An "aliphane" as used herein is a group composed of one or two cycloalkyl rings, with at least one aliphatic bridge between two non-adjacent positions of the single cycloalkyl ring or between the two cycloalkyl rings. The aliphatic bridges contain between 1 and 4 carbon atoms. The aliphatic bridges are optionally substituted with an oxo group.

"Alkenyl" is an alkyl group as defined herein, covalently bound to the group it substitutes by a keto (—(C=O)—) bridge. Alkanoyl groups have the indicated number of carbon atoms, with the carbon of the keto group being included in the numbered carbon atoms. For example a $C_2$alkanoyl group is an acetyl group having the formula $CH_3(C=O)$—.

"Alkyl" is a branched or straight chain saturated aliphatic hydrocarbon group, having the specified number of carbon atoms, generally from 1 to about 12 carbon atoms. The term $C_1$-$C_6$alkyl as used herein indicates an alkyl group having from 1, 2, 3, 4, 5, or 6 carbon atoms. Other embodiments include alkyl groups having from 1 to 8 carbon atoms, 1 to 4 carbon atoms or 1 or 2 carbon atoms, e.g. $C_1$-$C_8$alkyl, $C_1$-$C_4$alkyl, and $C_1$-$C_2$alkyl. When $C_0$-$C_n$ alkyl is used herein in conjunction with another group, for example, ($C_1$-$C_4$alkoxy)$C_0$-$C_4$ alkyl, the indicated group, in this case alkoxy, is either directly bound by a single covalent bond ($C_0$alkyl), or attached by an alkyl chain having the specified number of carbon atoms, in this case 1, 2, 3, or 4 carbon atoms. Examples of alkyl include, but are not limited to, methyl, ethyl, n-propyl, isopropyl, n-butyl, 3-methylbutyl, t-butyl, n-pentyl, and sec-pentyl.

"Alkynyl" is a branched or straight chain aliphatic hydrocarbon group having one or more triple carbon-carbon bonds that may occur at any stable point along the chain, having the specified number of carbon atoms. Examples of alkynyl include, but are not limited to, ethynyl and propynyl.

"Alkoxy" is an alkyl group as defined above with the indicated number of carbon atoms covalently bound to the group it substitutes by an oxygen bridge (—O—). Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy.

The term "alkylester" indicates an alkyl group as defined herein covalently bound to the group it substitutes by an ester linkage. The ester linkage may be in either orientation, e.g., a group of the formula —O(C=O)alkyl or a group of the formula —(C=O)Oalkyl.

"Alkylsulfonyl" is a group of the formula —$SO_2$alkyl, where the alkyl group carries the definition set forth herein.

"Cycloalkyl" is a saturated hydrocarbon ring group, having the specified number of carbon atoms. Monocyclic cycloalkyl groups typically have from 3 to about 8 carbon ring atoms or from 3 to 7 (3, 4, 5, 6, or 7) carbon ring atoms. Cycloalkyl substituents may be pendant from a substituted nitrogen or carbon atom, or a substituted carbon atom that may have two substituents may have a cycloalkyl group, which is attached as a spiro group. Examples of cycloalkyl groups include cyclopropyl, cyclobutyl, cyclopentyl, and cyclohexyl.

A "cyclophane" as used herein is a group composed of one or two aromatic rings, usually benzene rings, with at least one aliphatic bridge between two non-adjacent positions of the single aromatic ring or between the two aromatic rings. The aliphatic bridges are in the meta or para or meta, para (meta on one aromatic ring and para on the other) orientation and contain between 1 and 4 carbon atoms. The aliphatic bridges are optionally substituted with an oxo group.

"Haloalkyl" indicates both branched and straight-chain alkyl groups having the specified number of carbon atoms, substituted with 1 or more halogen atoms, up to the maximum allowable number of halogen atoms. Examples of haloalkyl include, but are not limited to, trifluoromethyl, difluoromethyl, 2-fluoroethyl, and penta-fluoroethyl.

"Haloalkoxy" indicates a haloalkyl group as defined herein attached through an oxygen bridge (oxygen of an alcohol radical).

"Halo" or "halogen" indicates any of fluoro, chloro, bromo, and iodo.

"Heteroaryl" indicates a stable monocyclic aromatic ring having the indicated number of ring atoms which contains from 1 to 3, or in some embodiments from 1 to 2, heteroatoms chosen from N, O, and S, with remaining ring atoms being carbon, or a stable bicyclic or tricyclic system containing at least one 5- to 7-membered aromatic ring which contains from 1 to 3, or in some embodiments from 1 to 2, heteroatoms chosen from N, O, and S, with remaining ring atoms being carbon. Monocyclic heteroaryl groups typically have from 5 to 7 ring atoms. In some embodiments bicyclic heteroaryl groups are 9- to 10-membered heteroaryl groups, that is, groups containing 9 or 10 ring atoms in which one 5- to 7-member aromatic ring is fused to a second aromatic or non-aromatic ring. When the total number of S and O atoms in the heteroaryl group exceeds 1, these heteroatoms are not adjacent to one another. It is preferred that the total number of S and O atoms in the heteroaryl group is not more than 2. It is particularly preferred that the total number of S and O atoms in the aromatic heterocycle is not more than 1. Examples of heteroaryl groups include, but are not limited to, oxazolyl, pyranyl, pyrazinyl, pyrazolopyrimidinyl, pyrazolyl, pyridizinyl, pyridyl, pyrimidinyl, pyrrolyl, quinolinyl, tetrazolyl, thiazolyl, thienylpyrazolyl, thiophenyl, triazolyl, benzo[d]oxazolyl, benzofuranyl, benzothiazolyl, benzothiophenyl, benzoxadiazolyl, dihydrobenzodioxynyl, furanyl, imidazolyl, indolyl, and isoxazolyl. "Heteroaryloxy" is a heteroaryl group as described bound to the group it substituted via an oxygen bridge.

A "hetera-phane" as used herein is a group composed of one or two aromatic rings, usually benzene rings, with at least one aliphatic bridge between two non-adjacent positions of the single aromatic ring or between the two aromatic rings that contains a heteroatom. The aliphatic bridges are in the meta or para or meta, para (meta on one aromatic ring and para on the other) orientation and contain between 1 and 4 atoms, at least one of which is a heteroatom with the remaining atoms being carbon atoms. The aliphatic bridges are optionally substituted with an oxo group.

A "hetero-phane" as used herein is a group composed of one or two aromatic rings, wherein at least one aromatic ring is heteroaryl, with at least one aliphatic bridge between two non-adjacent positions of the single aromatic ring or between the two aromatic rings. The aliphatic bridges are in the meta or para or meta, para (meta on one aromatic ring and para on the other) orientation and contain between 1 and 4 carbon atoms. The aliphatic bridges are optionally substituted with an oxo group.

A "hetero-hetera-phane" as used herein is a group composed of one or two aromatic rings, wherein at least one aromatic ring is heteroaryl, with at least one aliphatic bridge between two non-adjacent positions of the single aromatic ring or between the two aromatic rings that contains a hetero atom chosen from N, O, or S, and one aliphatic bridge between two non-adjacent positions of the single aromatic ring or between the two aromatic rings that does not contain a heteroatom. The aliphatic bridges are in the meta or para or meta, para (meta on one aromatic ring and para on the other) orientation and contain between 1 and 4 atoms, at least one of which is a heteroatom with the remaining atoms being carbon atoms. The aliphatic bridges are optionally substituted with an oxo group.

"Hydrocarbyl" is a saturated or unsaturated aliphatic group containing the indicated number of carbon atoms. "Hydrocarbyl may be used in conjunction with other groups, such as carbamate, as in "mono- or di-hydrocarbylcarbamate." Mono- or di-hydrocarbylcarbamate include groups of the formula $(alkyl_1)NH(C=O)O-$ and $(alkyl_1)N(alkyl_2)(C=O)O-$ as well as groups in which one or both of the alkyl groups are replaced by an hydrocarbon group containing unsaturated carbon-carbon bonds.

A "metallocene" is a compound consisting of two 5- or 6-membered aromatic carbocyclic groups bound to a metal center, where the metal is neutral or cationic. An example of metallocene includes, but is not limited to, ferrocene.

The term "mono- and/or di-alkylamino" indicates secondary or tertiary alkyl amino groups, wherein the alkyl groups are independently chosen alkyl groups, as defined herein, having the indicated number of carbon atoms. The point of attachment of the alkylamino group is on the nitrogen. Examples of mono- and di-alkylamino groups include ethylamino, dimethylamino, and methyl-propyl-amino.

"Mono- and/or di-alkylcarbamate" includes mono-alkylcarbamate groups of formula $(alkyl_1)O(C=O)NH-$ or a dialkylcarboxamide groups of the formula $(alkyl_1)O(C=O)N(alkyl_2)$- in which the point of attachment of the mono- or di-alkylcarboxamide substituent to the molecule it substitutes is on the nitrogen of the carbamate amino. The term "mono and/or di-alkylcarbamate" also includes groups of the formula $(alkyl_1)NH(C=O)O-$ and $(alkyl_1)N(alkyl_2)(C=O)O-$ in which the carbamate is covalently bound to the group it substitutes by its non-keto oxygen atom. The groups $alkyl_1$ and $alkyl_2$ are independently chosen alkyl groups, carrying the alkyl definition set forth in this disclosure and having the indicated number of carbon atoms.

"Mono- and/or di-alkylcarboxamide" indicates a mono-alkylcarboxamide group of formula $(alkyls)-NH-(C=O)-$ or a dialkylcarboxamide group of the formula $(alkyl_1)(alkyl_2)-N-(C=O)-$ in which the point of attachment of the mono- or dialkylcarboxamide substituent to the molecule it substitutes is on the carbon of the carbonyl group. The term "mono and/or di-alkylcarboxamide" also includes groups of the formula $(alkyl_1)(C=O)NH-$ and $(alkyl_1)(C=O)(alkyl_2)N-$ in which the point of attachment is the nitrogen atom. The groups $alkyl_1$ and $alkyl_2$ are independently chosen alkyl groups having the indicated number of carbon atoms. Likewise "mono- and/or di-alkyl sulfonamide" is any of a mono-alkylsulfonamide group of formula $(alkyl_1)-NH-(SO_2)-$, a mono-alkyl sulfonamide group of formula $(alkyl_1)-(SO_2)-NH-$, a dialkylsulfonamide group of the formula $(alkyl_1)(alkyl_2)-N-(SO_2)-$, and a group of the formula $(alkyl_1)-(SO_2)-(alkyl_2)N-$.

"Thioalkyl" is an alkyl group as defined above with the indicated number of carbon atoms covalent bound to the group it substitutes by an sulfur bridge (—S—).

The term "substituted", as used herein, means that any one or more hydrogens on the designated atom or group is replaced with a selection from the indicated group, provided that the designated atom's normal valence is not exceeded. When the substituent is oxo (i.e., =O) then 2 hydrogens on the atom are replaced. When an oxo group substitutes aromatic moieties, the corresponding partially unsaturated ring replaces the aromatic ring. For example a pyridyl group substituted by oxo is a pyridone. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation into an effective therapeutic agent. Unless otherwise specified substituents are named into the core structure. For example, it is to be understood that when aminoalkyl is listed as a possible substituent the point of attachment of this substituent to the core structure is in the alkyl portion.

Suitable groups that may be present on a "substituted" position include, but are not limited to, e.g., halogen; cyano; hydroxyl; nitro; azido; alkanoyl (such as a $C_2$-$C_6$ alkanoyl group); carboxamide; alkyl groups (including cycloalkyl groups) having 1 to about 8 carbon atoms, or 1 to about 6 carbon atoms; alkenyl and alkynyl groups including groups having one or more unsaturated linkages and from 2 to about 8, or 2 to about 6 carbon atoms; alkoxy groups having one or more oxygen linkages and from 1 to about 8, or from 1 to about 6 carbon atoms; aryloxy such as phenoxy; alkylthio groups including those having one or more thioether linkages and from 1 to about 8 carbon atoms, or from 1 to about 6 carbon atoms; alkylsulfinyl groups including those having one or more sulfinyl linkages and from 1 to about 8 carbon atoms, or from 1 to about 6 carbon atoms; alkylsulfonyl groups including those having one or more sulfonyl linkages and from 1 to about 8 carbon atoms, or from 1 to about 6 carbon atoms; aminoalkyl groups including groups having one or more N atoms and from 1 to about 8, or from 1 to about 6 carbon atoms; aryl having 6 or more carbons and one or more rings, (e.g., phenyl, biphenyl, naphthyl, or the like, each ring either substituted or unsubstituted aromatic); arylalkyl having 1 to 3 separate or fused rings and from 6 to about 18 ring carbon atoms, with benzyl being an exemplary arylalkyl group; arylalkoxy having 1 to 3 separate or fused rings and from 6 to about 18 ring carbon atoms, with benzyloxy being an exemplary arylalkoxy group; or a saturated, unsaturated, or aromatic heterocyclic group having 1 to 3 separate or fused rings with 3 to about 8 members per ring and one or more N, O or S atoms, e.g. coumarinyl, quinolinyl, isoquinolinyl, quinazolinyl, pyridyl, pyrazinyl, pyrimidinyl, furanyl, pyrrolyl, thienyl, thiazolyl, triazinyl, oxazolyl, isoxazolyl, imidazolyl, indolyl, benzofuranyl, benzothiazolyl, tetrahydrofuranyl, tetrahydropyranyl, piperidinyl, morpholinyl, piperazinyl, and pyrrolidinyl. Such heterocyclic groups may be further substituted, e.g. with hydroxy, alkyl, alkoxy, halogen and amino.

A "dosage form" means a unit of administration of an active agent. Examples of dosage forms include tablets, capsules, injections, suspensions, liquids, emulsions, creams, ointments, suppositories, inhalable forms, transdermal forms, and the like.

"Pharmaceutical compositions" are compositions comprising at least one active agent, such as a compound or salt of Formula I, and at least one other substance, such as a carrier. Pharmaceutical compositions optional contain one or more additional active agents. When specified, pharmaceutical compositions meet the U.S. FDA's GMP (good manufacturing practice) standards for human or non-human drugs. "Pharmaceutical combinations" are combinations of at least two active agents which may be combined in a single dosage form or provided together in separate dosage forms with instructions that the active agents are to be used together to treat a disorder, such as hepatitis C.

"Pharmaceutically acceptable salts" includes derivatives of the disclosed compounds in which the parent compound is modified by making inorganic and organic, non-toxic, acid or base addition salts thereof. The salts of the present compounds can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are preferred, where practicable. Salts of the present compounds further include solvates of the compounds and of the compound salts.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—$(CH_2)_n$—COOH where n is 0-4, and the like. Lists of additional suitable salts may be found, e.g., in *Remington's Pharmaceutical Sciences*, 17th ed., Mack Publishing Company, Easton, Pa., p. 1418 (1985).

The term "carrier" applied to pharmaceutical compositions/combinations of the invention refers to a diluent, excipient, or vehicle with which an active compound is provided.

A "pharmaceutically acceptable excipient" means an excipient that is useful in preparing a pharmaceutical composition/combination that is generally safe, non-toxic and neither biologically nor otherwise undesirable, and includes an excipient that is acceptable for veterinary use as well as human pharmaceutical use. A "pharmaceutically acceptable excipient" as used in the present application includes both one and more than one such excipient.

A "patient" is a human or non-human animal in need of medical treatment. Medical treatment can include treatment of an existing condition, such as a disease or disorder, prophylactic or preventative treatment, or diagnostic treatment. In some embodiments the patient is a human patient.

"Providing" means giving, administering, selling, distributing, transferring (for profit or not), manufacturing, compounding, or dispensing.

"Providing a compound of Formula I with at least one additional active agent" means the compound of Formula I and the additional active agent(s) are provided simultaneously in a single dosage form, provided concomitantly in separate dosage forms, or provided in separate dosage forms for administration separated by some amount of time that is within the time in which both the compound of Formula I and the at least one additional active agent are within the blood stream of a patient. In certain embodiments the compound of Formula I and the additional active agent need not be prescribed for a patient by the same medical care worker. In certain embodiments the additional active agent or agents need not require a prescription. Administration of the compound of Formula I or the at least one additional active agent can occur via any appropriate route, for example, oral tablets, oral capsules, oral liquids, inhalation, injection, suppositories or topical contact.

"Treatment," as used herein includes providing a compound of Formula I, either as the only active agent or together with at least one additional active agent sufficient to: (a) prevent a disease or a symptom of a disease from occurring in a patient who may be predisposed to the disease but has not yet been diagnosed as having it (e.g. including diseases that may be associated with or caused by a primary disease (as in liver fibrosis that can result in the context of chronic HCV infection); (b) inhibiting the disease, i.e. arresting its development; and (c) relieving the disease, i.e., causing regression of the disease. "Treating" and "treatment" also means providing a therapeutically effective amount of a compound of Formula I, as the only active agent or together with at least one additional active agent to a patient having or susceptible to a hepatitis C infection.

A "therapeutically effective amount" of a pharmaceutical composition/combination of this invention means an amount effective, when administered to a patient, to provide a therapeutic benefit such as an amelioration of symptoms, e.g., an amount effective to decrease the symptoms of a hepatitis C infection. For example a patient infected with a hepatitis C virus may present elevated levels of certain liver enzymes, including AST and ALT. Normal levels of AST are from 5 to 40 units per liter of serum (the liquid part of the blood) and normal levels of ALT are from 7 to 56 units per liter of serum. A therapeutically effect amount is thus an amount sufficient to provide a significant reduction in elevated AST and ALT levels or an amount sufficient to provide a return of AST and ALT levels to the normal range. A therapeutically effective amount is also an amount sufficient to prevent a significant increase or significantly reduce the detectable level of virus or viral antibodies in the patient's blood, serum, or tissues. One method of determining treatment efficacy includes measuring HCV RNA levels by a conventional method for determining viral RNA levels such as the Roche TaqMan assay. In certain preferred embodiments treatment reduces HCV RNA levels below the limit of quantitation (30 IU/mL, as measured by the Roche TaqMan® assay) or more preferably below the limit of detection (10 IU/mL, Roche TaqMan).

A significant increase or reduction in the detectable level of virus or viral antibodies is any detectable change that is statistically significant in a standard parametric test of statistical significance such as Student's T-test, where $p<0.05$.

Chemical Description

Formula I and Formula II (shown below) include all subformulae thereof. In certain situations, the compounds of Formula I or Formula II may contain one or more asymmetric elements such as stereogenic centers, stereogenic axes and the like, e.g. asymmetric carbon atoms, so that the compounds can exist in different stereoisomeric forms. These compounds can be, for example, racemates or optically active forms. For compounds with two or more asymmetric elements, these compounds can additionally be mixtures of diastereomers. For compounds having asymmetric centers, it should be understood that all of the optical isomers and mixtures thereof are encompassed. In addition, compounds with carbon-carbon double bonds may occur in Z- and E-forms, with all isomeric forms of the compounds being included in the present invention. In these situations, single enantiomers, i.e., optically active forms, can be obtained by asymmetric synthesis, synthesis from optically pure precursors, or by resolution of the racemates. Resolution of the racemates can also be accomplished, for example, by conventional methods such as crystallization in the presence of a resolving agent, or chromatography, using, for example using a chiral HPLC column.

Where a compound exists in various tautomeric forms, the invention is not limited to any one of the specific tautomers, but rather includes all tautomeric forms.

The present invention is intended to include all isotopes of atoms occurring in the present compounds. Isotopes include those atoms having the same atomic number but different mass numbers. By way of general example, and without limitation, isotopes of hydrogen include tritium and deuterium and isotopes of carbon include $^{11}C$, $^{13}C$, and $^{14}C$.

Certain compounds are described herein using a general formula that includes variables, e.g. D, M, A, P, J, and W. Unless otherwise specified, each variable within such a formula is defined independently of other variables. Thus, if a group is said to be substituted, e.g. with 0-2 R*, then the group may be substituted with up to two R* groups and R* at each occurrence is selected independently from the definition of R*. Also, combinations of substituents and/or variables are permissible only if such combinations result in stable compounds.

In addition the compounds and salts of Formula I discussed in the SUMMARY section, the disclosure includes compounds and salt of Formula I, and pharmaceutical compositions/combinations of such compounds in which the variables meet any of the following conditions.

(i) D-M-D is any of

T-R-J¹-A-W-J¹-R-T;

T-R-J¹-A-J¹-R-T;

T-R-J²-A-J²-R-T;

T-R-J¹-W-A-J²-R-T; and

T-R-J¹-A-J²-R-T.

(ii) A is

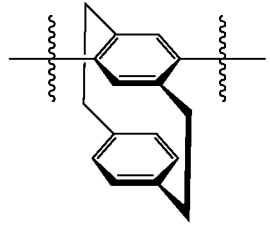

(iii) A is
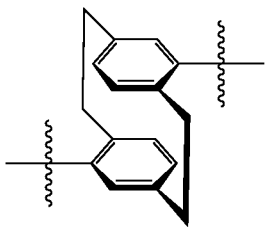
(iv) A is
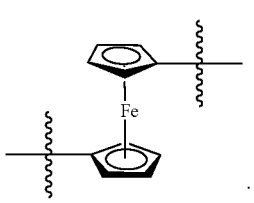
(v) A is
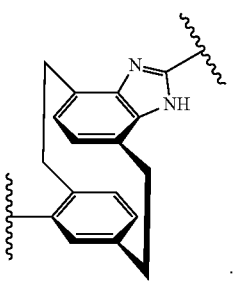
(vi) A is
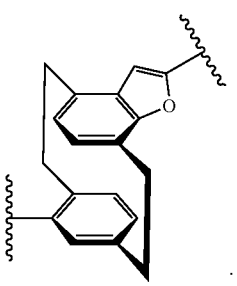
(vii) A is
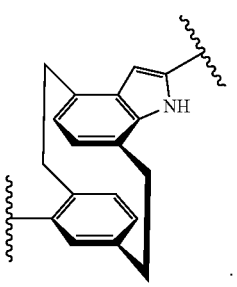
(viii) A is
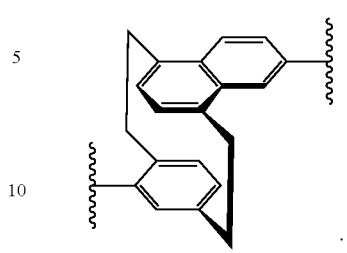
(ix) A is
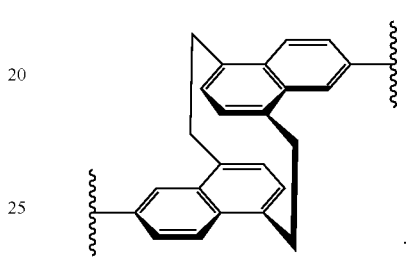
(x) A is
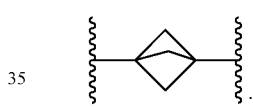
(xi) A is
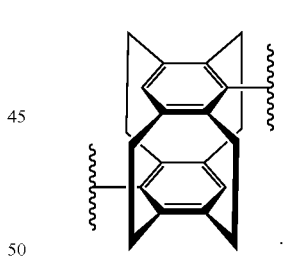
(xii) A is
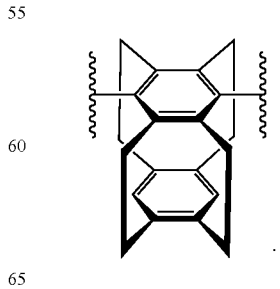

(xiii) A is

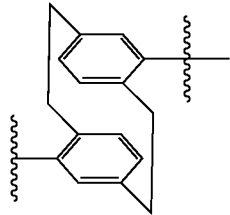

(xiv) A is

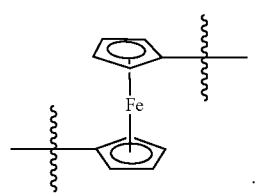

(xv) At least one P is $J^1$-W; and W is phenyl, optionally substituted with one or more substituents independently chosen from halogen, $C_1$-$C_2$alkyl, and $C_1$-$C_2$alkoxy.

(xvi) P is J-W or J, wherein at least one J is $J^1$ and $J^1$ is

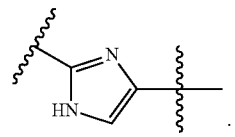 [SMILES: *c1c[nH]c(*)n1]

(xvii) At least one P is $J^1$ and $J^1$ is

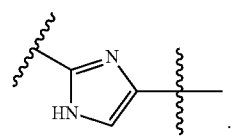 [SMILES: *c1c[nH]c(*)n1]

(xviii) At least one P is $J^2$ and $J^2$ is a benzimidazole group, optionally substituted with one or more substituents independently chosen from halogen, $C_1$-$C_2$alkyl, and $C_1$-$C_2$alkoxy.

(xix) R is independently chosen from

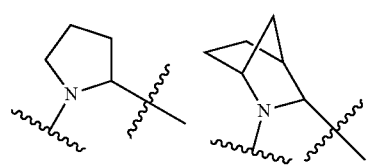

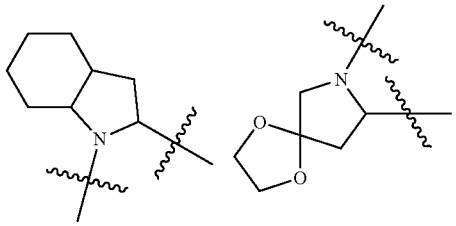

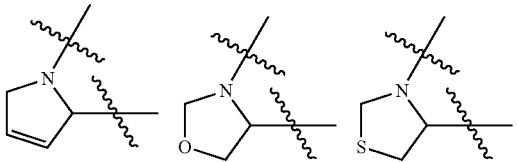

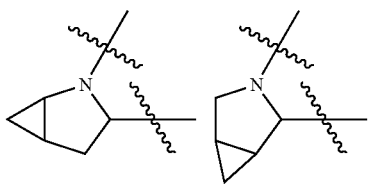

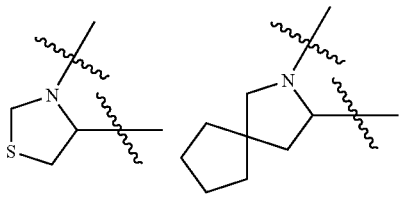

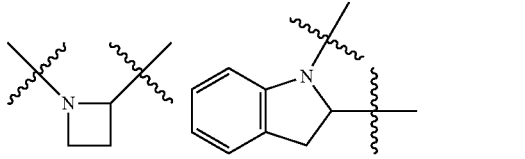

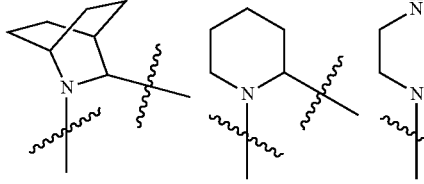

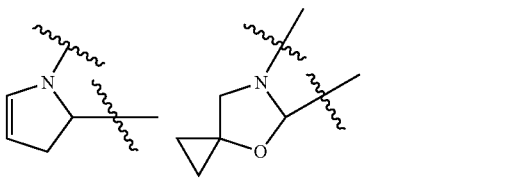

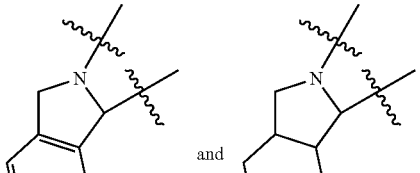

and

each of which is optionally substituted with one or more substituents independently chosen from halogen, $C_1$-$C_4$alkyl, and $C_1$-$C_4$alkoxy.

(xx) R is independently chosen from

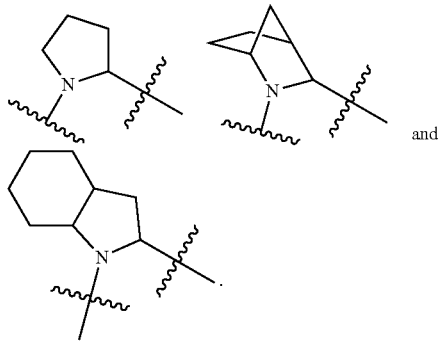

and

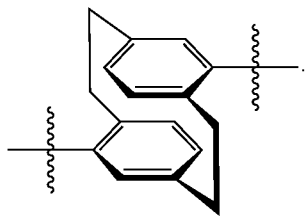

.

(xxi) T is independently chosen $C_2$-$C_6$alkanoyl substituted with mono- and di-$C_1$-$C_6$alkylcarbamate, each of which T is optionally substituted with ($C_1$-$C_4$thioalkyl)$C_0$-$C_4$alkyl.

(xxii) Also included are compounds and salts of the formula T-R-$J^2$-A-$J^2$-R-T.

A, in the formula T-R-$J^2$-A-$J^2$-R-T, is a group of the formula

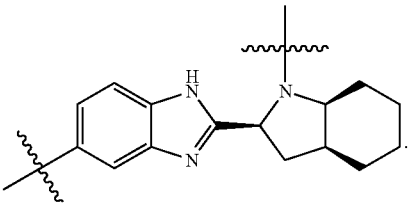 [SMILES: *c1ccc2[nH]c([C@@H]3C[C@@H]4CCCC[C@@H]4N3*)nc2c1]

$J^2$ is an 8- to 10-membered heteroaryl group containing for 2 heteroatoms independently chosen from N, O, and S, wherein $J^2$ is optionally substituted with one or more substituents independently chosen from amino, cyano, hydroxyl, halogen, $C_1$-$C_4$alkyl, $C_1$-$C_4$alkoxy, mono- and di-$C_1$-$C_4$alkylamino, $C_1$-$C_2$haloalkyl, and $C_1$-$C_2$haloalkoxy.

Each R is an independently chosen 8- to 10-membered bicyclic ring systems containing one or two nitrogen atoms with remaining ring atoms being carbon, which 8- to 10-membered bicyclic ring is saturated or contains 1 unsaturated bond; and R is optionally substituted with one or more substituents independently chosen from cyano, hydroxyl, halogen, $C_1$-$C_2$alkyl, $C_1$-$C_2$alkoxy, $C_1$-$C_2$haloalkyl, $C_1$-$C_2$haloalkyl, $C_1$-$C_2$haloalkylene, and $C_1$-$C_2$alkylsulfonyl.

$T^2$ is independently chosen at each occurrence from $C_2$-$C_6$alkanoyl, $C_1$-$C_6$alkylester, $C_1$-$C_6$alkenylester, $C_1$-$C_6$alkylsulfonamide, $C_1$-$C_6$alkylsulfonyl, $C_2$-$C_6$alkanoyl substituted with mono- or di-$C_1$-$C_6$hydrocarbylcarbamate, $C_2$-$C_6$alkanoyl substituted with urea or mono- or di-$C_1$-$C_6$alkylurea, and $C_2$-$C_6$alkanoyl substituted with mono- or di-$C_1$-$C_6$alkylcarboxamide, each of which $T^2$ is optionally substituted with 1 or more substituents independently chosen from amino, cyano, hydroxyl, halogen, ($C_1$-$C_4$alkoxy)$C_0$-$C_4$alkyl, (mono- and di-$C_1$-$C_4$alkylamino)$C_0$-$C_4$alkyl, $C_1$-$C_6$alkyl, ($C_1$-$C_4$thioalkyl)$C_0$-$C_4$alkyl, $C_3$-$C_7$cycloalkyl, phenyl, $C_1$-$C_2$haloalkyl, and $C_1$-$C_2$haloalkoxy.

In certain embodiments of xxii, it is preferred that -$J^2$-R— is a group of the formula

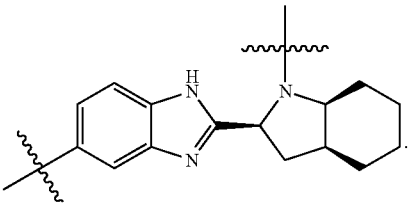 [SMILES: *c1ccc2[nH]c([C@@H]3C[C@@H]4CCCC[C@@H]4N3*)nc2c1]

or more particularly

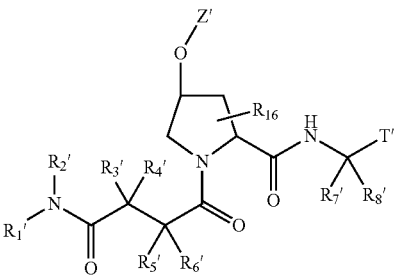

.

$J^2$-R— may be unsubstituted or substituted with one or more substituents independently chosen from amino, cyano, hydroxyl, halogen, $C_1$-$C_4$alkyl, $C_1$-$C_4$alkoxy, mono- and di-$C_1$-$C_4$alkylamino, $C_1$-$C_2$haloalkyl, and $C_1$-$C_2$haloalkoxy.

In certain embodiments of xxii, it is also preferred that $T^2$ is $C_2$-$C_6$alkanoyl substituted with mono- or di-$C_1$-$C_6$hydrocarbylcarbamate, which $T^2$ is optionally substituted with 1 or more substituents independently chosen from amino, cyano, hydroxyl, halogen, ($C_1$-$C_4$alkoxy)$C_0$-$C_4$alkyl, (mono- and di-$C_1$-$C_4$alkylamino)$C_0$-$C_4$alkyl, $C_1$-$C_6$alkyl, ($C_1$-$C_4$thioalkyl)$C_0$-$C_4$alkyl, $C_3$-$C_7$cycloalkyl, phenyl, $C_1$-$C_2$haloalkyl, and $C_1$-$C_2$haloalkoxy.

Any of the preceding conditions for compounds of Formula I may be used together to define a subgeneric formula of Formula I so long as a stable compound results. All such subgeneric formulas are included in this disclosure.

In addition the compounds and salts of Formula I discussed in the SUMMARY section, the disclosure includes compositions and combinations of Formula I and Formula II, wherein Formula II is:

Formula II

Within Formula II the variables $R_1'$, $R_2'$, $R_3'$, $R_4'$, $R_6'$, $R_7'$, $R_8'$, $R_{16}$, and T' carry the definitions set forth below.

$R_1'$ and $R_2'$ are joined to form a 5- to 7-membered heterocycloalkyl ring containing 1 or 2 heteroatoms independently chosen from N, O, and S which ring is optionally fused to a phenyl or 5- or 6-membered heteroaryl to form a bicyclic ring system, each of which 5- to 7-membered heterocycloalkyl ring or bicyclic ring system is optionally substituted.

For the variables $R_3'$-$R_8'$ one of the following conditions is met. $R_3'$, $R_4'$, $R_5'$, and $R_6'$ are independently hydrogen, $C_1$-$C_4$alkyl, or $(C_3$-$C_7$cycloalkyl$)C_0$-$C_4$alkyl; and $R_7'$ and $R_8'$ are joined to form an optionally substituted 3- to 7-membered cycloalkyl ring.

$R_3'$, $R_4'$, and $R_6'$ are independently hydrogen, $C_1$-$C_4$alkyl, or $(C_3$-$C_7$cycloalkyl$)C_0$-$C_4$alkyl; and $R_8'$ is hydrogen or $C_1$-$C_4$alkyl; and $R_5'$ is joined to $R_7'$ by a $C_6$-$C_{10}$ saturated or unsaturated hydrocarbon chain.

$R_3'$, $R_4'$, and $R_6'$ are independently hydrogen, $C_1$-$C_4$alkyl, or $(C_3$-$C_7$cycloalkyl$)C_0$-$C_4$alkyl; and $R_7'$ and $R_8'$ are joined to form an optionally substituted 3- to 7-membered cycloalkyl ring; and $R_5'$ is joined to the 3- to 7-membered optionally substituted cycloalkyl ring formed by $R_7$ and $R_8$ by a $C_6$-$C_{10}$ saturated, partially unsaturated or unsaturated hydrocarbon chain.

T' is a group of the formula:

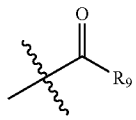

$R_9$ is hydroxyl, amino, —COOH, —$NR_{10}R_{11}$, —$OR_{12}$, —$NR_{10}(S=O)R_{11}$, or —$NR_{10}SO_2R_{11}$. $R_{10}$, $R_{11}$, and $R_{12}$ are independently at each occurrence hydrogen, or $C_1$-$C_6$alkyl, $C_2$-$C_6$alkenyl, (aryl)$C_0$-$C_2$alkyl, $(C_3$-$C_7$cycloalkyl$)C_0$-$C_2$alkyl, (heterocycloalkyl)$C_0$-$C_2$alkyl, or (5- to 10-membered heteroaryl)$C_0$-$C_2$alkyl, each of which is optionally substituted with 1 to 3 substituents independently chosen from halogen, hydroxyl, oxo, $C_1$-$C_2$alkyl, $C_1$-$C_2$alkoxy, trifluoromethyl, and trifluoromethoxy:

Z' is

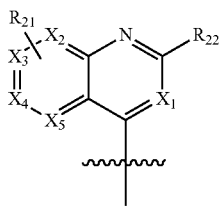

where $X_1$, $X_2$, $X_3$, $X_4$, and $X_5$ are independently N or CH and no more than two of $X_1$-$X_5$ are N.

$R_{21}$ represents from 0 to 3 groups independently chosen from halogen, hydroxyl, amino, cyano, —$CONH_2$, —COOH, $C_1$-$C_4$alkyl, $C_2$-$C_4$alkanoyl, $C_1$-$C_4$alkoxy, $C_1$-$C_4$alkylthio, mono- and di-$C_1$-$C_4$alkylamino, $C_1$-$C_2$haloalkyl, and $C_1$-$C_2$haloalkoxy.

$R_{22}$ is hydrogen, halogen, hydroxyl, amino, cyano, —$CONH_2$, —COOH, $C_1$-$C_4$alkyl, $C_2$-$C_4$alkanoyl, $C_1$-$C_4$alkoxy, $C_1$-$C_4$alkylthio, mono- and di-$C_1$-$C_4$alkylamino, $C_1$-$C_4$alkylester, $C_1$-$C_2$haloalkyl, and $C_1$-$C_2$haloalkoxy; or $R_{22}$ is $(C_3$-$C_7$cycloalkyl$)C_0$-$C_2$alkyl, (phenyl)$C_0$-$C_2$alkyl, (phenyl)$C_0$-$C_2$alkoxy, (5- or 6-membered heteroaryl)$C_0$-$C_2$alkyl, (5- or 6-membered heteroaryl)$C_0$-$C_2$alkoxy, naphthyl, indanyl, (5- or 6-membered heterocycloalkyl)$C_0$-$C_2$alkyl, or 9- or 10 membered bicyclic heteroaryl, each of which is substituted with 0, 1, or 2 substituents independently chosen from (i) halogen, hydroxyl, amino, cyano, nitro, —COOH, —$CONH_2$, $CH_3(C=O)NH$—, $C_1$-$C_4$alkyl, $C_1$-$C_4$alkoxy, $C_1$-$C_4$hydroxyalkyl, mono- and di-$C_1$-$C_4$alkylamino, —$NR_8SO_2R_{11}$, —$C(O)OR_{11}$, —$NR_8COR_{11}$, —$NR_8C(O)OR_{11}$, trifluoromethyl, trifluoromethoxy, and (ii) phenyl and 5- or 6-membered heteroaryl, each of which is substituted with 0 or 1 or more of halogen, hydroxyl, $C_1$-$C_4$alkyl, and $C_1$-$C_2$alkoxy; wherein $R_8$ is hydrogen, $C_1$-$C_4$alkyl, or $C_3C_6$cycloalkyl, and $R_{11}$ is as defined above.

$R_{16}$ represents 0 to 4 substituents is independently chosen at from halogen, $C_1$-$C_2$alkyl, and $C_1$-$C_2$alkoxy.

Any of the preceding conditions for compounds of Formula I may be used together to define a subgeneric formula of Formula I so long as a stable compound results and all such subgeneric formulas are included in this disclosure.

This disclosure also includes pharmaceutical compositions and combinations comprising a compound of Formula I and a compound of Formula II. As well as methods of treatment comprising administering such compositions/combinations to a patient infected with hepatitis C.

For example the disclosure includes compositions and combinations in which the compound of Formula II is

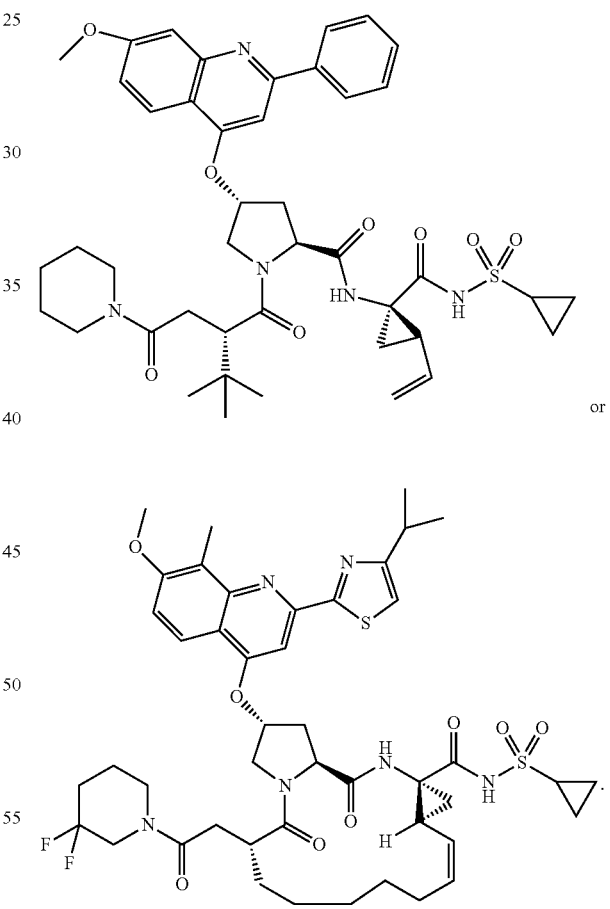

or

This disclosure also includes pharmaceutical compositions and combinations comprising a compound of Formula I and a compound of Formula II. As well as methods of treatment comprising administering such compositions/combinations to a patient infected with hepatitis C.

For example the disclosure includes compositions and combinations in which the compound of Formula II is

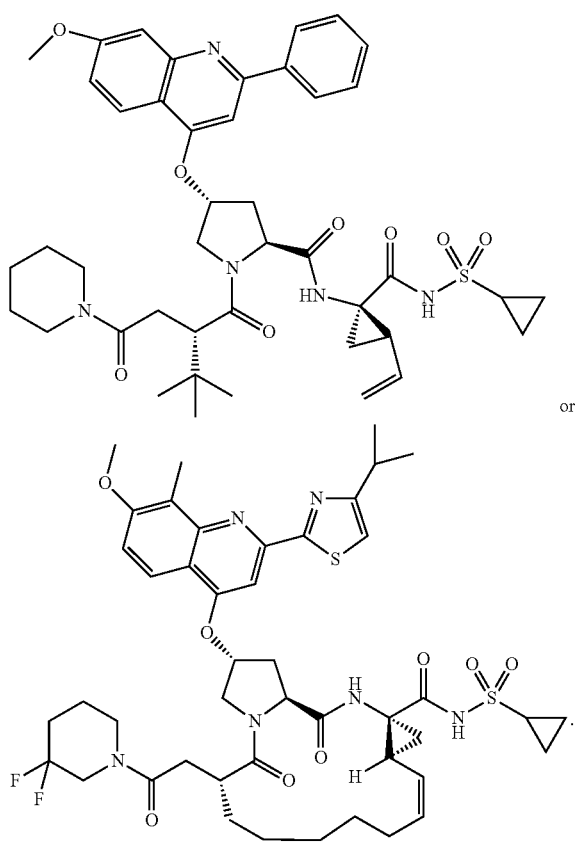

NS3a protease inhibitors of Formula II, useful in the pharmaceutical compositions and combinations described here have been disclosed previously. U.S. Pat. No. 7,906,619, issued Mar. 15, 2011, is hereby incorporated by reference in its entirety for its teachings regarding 4-amino-4-oxobutanoyl peptides. The '619 patent is particularly incorporated by reference at the Examples section beginning in column 50 and extending to column 85 which discloses compounds useful in compositions/combination with Compounds of Formula I described here.

Published US Pat. Appl. No. 2010-0216725, published Aug. 26, 2010, is hereby incorporated by reference in its entirety for its teachings regarding 4-amino-4-oxobutanoyl peptides. The '725 application is particularly incorporated by reference at the Examples section beginning at page 22 and extending to page 100 which discloses compounds useful in compositions/combination with Compounds of Formula I described here.

Published US Pat. Appl. No. 2010-0152103, published Jun. 17, 2010, is hereby incorporated by reference in its entirety for its teachings regarding 4-amino-4-oxobutanoyl peptide cyclic analogues. The '103 application is particularly incorporated by reference at the Examples section beginning at page 19 and extending to page 60 which discloses compounds useful in compositions/combination with Compounds of Formula I described here.

Pharmaceutical Preparations

Compounds disclosed herein can be administered as the neat chemical, but are preferably administered as a pharmaceutical composition. Accordingly, the disclosure provides pharmaceutical compositions comprising a compound or pharmaceutically acceptable salt of Formula I, together with at least one pharmaceutically acceptable carrier. The pharmaceutical composition/combination may contain a compound or salt of Formula I as the only active agent, but is preferably contains at least one additional active agent. In certain embodiments it is preferred that the additional active agent is an NS3a protease inhibitor, such as a compound of salt of Formula II. In certain embodiments the pharmaceutical composition is in a dosage form that contains from about 0.1 mg to about 2000 mg, from about 10 mg to about 1000 mg, from about 100 mg to about 800 mg, or from about 200 mg to about 600 mg of a compound of Formula I and optionally from about 0.1 mg to about 2000 mg, from about 10 mg to about 1000 mg, from about 100 mg to about 800 mg, or from about 200 mg to about 600 mg of an additional active agent in a unit dosage form. The pharmaceutical composition may also include a molar ratio of a compound of Formula I and an additional active agent. For example the pharmaceutical composition may contain a molar ratio of about 0.5:1, about 1:1, about 2:1, about 3:1 or from about 1.5:1 to about 4:1 of an NS3a protease inhibitor of Formula II to NS5a inhibitor of Formula I.

Compounds disclosed herein may be administered orally, topically, parenterally, by inhalation or spray, sublingually, transdermally, via buccal administration, rectally, as an ophthalmic solution, or by other means, in dosage unit formulations containing conventional pharmaceutically acceptable carriers. The pharmaceutical composition may be formulated as any pharmaceutically useful form, e.g., as an aerosol, a cream, a gel, a pill, a capsule, a tablet, a syrup, a transdermal patch, or an ophthalmic solution. Some dosage forms, such as tablets and capsules, are subdivided into suitably sized unit doses containing appropriate quantities of the active components, e.g., an effective amount to achieve the desired purpose.

Carriers include excipients and diluents and must be of sufficiently high purity and sufficiently low toxicity to render them suitable for administration to the patient being treated. The carrier can be inert or it can possess pharmaceutical benefits of its own. The amount of carrier employed in conjunction with the compound is sufficient to provide a practical quantity of material for administration per unit dose of the compound.

Classes of carriers include, but are not limited to binders, buffering agents, coloring agents, diluents, disintegrants, emulsifiers, flavorants, glidents, lubricants, preservatives, stabilizers, surfactants, tableting agents, and wetting agents. Some carriers may be listed in more than one class, for example vegetable oil may be used as a lubricant in some formulations and a diluent in others. Exemplary pharmaceutically acceptable carriers include sugars, starches, celluloses, powdered tragacanth, malt, gelatin; talc, and vegetable oils. Optional active agents may be included in a pharmaceutical composition, which do not substantially interfere with the activity of the compound of the present invention.

The pharmaceutical compositions/combinations can be formulated for oral administration. These compositions contain between 0.1 and 99 weight % (wt. %) of a compound of Formula I and usually at least about 5 wt. % of a compound of Formula. Some embodiments contain from about 25 wt. % to about 50 wt. % or from about 5 wt. % to about 75 wt. % of the compound of Formula.

Methods of Treatment

The pharmaceutical compositions/combinations disclosed herein are useful for treating hepatitis C infections in patients.

This disclosure provides methods of treating viral infections, including hepatitis C infections, by providing an effective amount of a compound or pharmaceutically acceptable salt of Formula I to patient infected with a hepatitis C virus. A compound or salt of Formula I may be provided as the only active agent or may be provided together with one or more additional active agents. In certain embodiments the compound or salt of Formula I is administered together with a compound or salt of Formula II or other NS3a protease inhibitor. In certain embodiment the pharmaceutical composition contains a compound of Formula I together with an NS5b inhibitor, and optionally an additional active agent.

An effective amount of a pharmaceutical composition/combination of the invention may be an amount sufficient to (a) inhibit the progression of hepatitis C; (b) cause a regression of the hepatitis C infection; or (c) cause a cure of a hepatitis C infection such that HCV virus or HCV antibodies can no longer be detected in a previously infected patient's blood or plasma. An amount of a pharmaceutical composition/combination effective to inhibit the progress or cause a regression of hepatitis C includes an amount effective to stop the worsening of symptoms of hepatitis C or reduce the symptoms experienced by a patient infected with the hepatitis C virus. Alternatively a halt in progression or regression of hepatitis C may be indicated by any of several markers for the disease. For example, a lack of increase or reduction in the hepatitis C viral load or a lack of increase or reduction in the number of circulating HCV antibodies in a patient's blood are markers of a halt in progression or regression of hepatitis C infection. Other hepatitis C disease markers include aminotransferase levels, particularly levels of the liver enzymes AST and ALT. Normal levels of AST are from 5 to 40 units per liter of serum (the liquid part of the blood) and normal levels of ALT are from 7 to 56 units per liter of serum. These levels will typically be elevated in a HCV infected patient. Disease regression is usually marked by the return of AST and ALT levels to the normal range.

Symptoms of hepatitis C that may be affected by an effective amount of a pharmaceutical composition/combination of the invention include decreased liver function, fatigue, flu-like symptoms: fever, chills, muscle aches, joint pain, and headaches, nausea, aversion to certain foods, unexplained weight loss, psychological disorders including depression, tenderness in the abdomen, and jaundice.

"Liver function" refers to a normal function of the liver, including, but not limited to, a synthetic function including synthesis of proteins such as serum proteins (e.g., albumin, clotting factors, alkaline phosphatase, aminotransferases (e.g., alanine transaminase, aspartate transaminase), 5'-nucleosidase, y glutaminyltranspeptidase, etc.), synthesis of bilirubin, synthesis of cholesterol, and synthesis of bile acids; a liver metabolic function, including carbohydrate metabolism, amino acid and ammonia metabolism, hormone metabolism, and lipid metabolism; detoxification of exogenous drugs; and a hemodynamic function, including splanchnic and portal hemodynamics.

An effective amount of a pharmaceutical composition/combination described herein will also provide a sufficient concentration of the active agents in the concentration when administered to a patient. A sufficient concentration of an active agent is a concentration of the agent in the patient's body necessary to prevent or combat the infection. Such an amount may be ascertained experimentally, for example by assaying blood concentration of the agent, or theoretically, by calculating bioavailability. The amount of an active agent sufficient to inhibit viral infection in vitro may be determined with a conventional assay for viral infectivity such as a replicon based assay, which has been described in the literature.

Pharmaceutical compositions/combinations and methods of treatment in which a compound or salt of Formula I is provided together with one or more additional active agents are included herein. In preferred embodiments a compound of Formula I is provided together with an NS3a protease inhibitor, either in a single pharmaceutical composition or a in separate dosage forms with instructions to the patient to use the compound of Formula I and additional active agent together. Compounds of Formula II and compounds disclosed in U.S. Pat. No. 7,906,619, US Pat. Appl. No. 2010-0216725, and US Pat. Appl. No. 2010-0152103, most of which are within the scope of Formula II, are suitable NS3a protease inhibitors for use in combination with compounds and salts of Formula I. In certain embodiments the active agent (or agents) is an HCV protease inhibitor or HCV polymerase inhibitor. For example the protease inhibitor may be telaprevir (VX-950) and the polymerase inhibitor may be valopicitabine, or NM 107, the active agent which valopicitabine is converted into in vivo. In certain embodiments the at least one additional active agent is ribavirin, interferon, or Peg-interferon alpha conjugate. In certain embodiments the at least one additional active agent is ACH-1625 or ACH-2684.

According to the methods of the invention, the compound or pharmaceutically acceptable salt of Formula I and at least one additional active agent may be: (1) co-formulated and administered or delivered simultaneously in a combined formulation; (2) delivered by alternation or in parallel as separate formulations; or (3) by any other combination therapy regimen known in the art. When delivered in alternation therapy, the methods of the invention may comprise administering or delivering the compound or salt of Formula I and an additional active agent sequentially, e.g., in separate solution, emulsion, suspension, tablets, pills or capsules, or by different injections in separate syringes. In general, during alternation therapy, an effective dosage of each active ingredient is administered sequentially, i.e., serially, whereas in simultaneous therapy, effective dosages of two or more active ingredients are administered together. Various sequences of intermittent combination therapy may also be used.

Methods of treatment and pharmaceutical combinations including compounds or pharmaceutically acceptable salts of Formula I described herein together with any one or combination of the following compounds and substances as an additional active agent are provided by the disclosure:

Anti-fibrotics: IP-501 (InterMune)

Caspase Inhibitors: IDN-6556 (Idun Pharmaceuticals) and GS-9450 (Gilead)

Cyclophilin Inhibitors: for example, NIM811 (Novartis), SCY-635 (Scynexis), and DEBIO-025 (Debiopharm);

Cytochrome P450 monooxygenase inhibitors: ritonavir, ketoconazole, troleandomycin, 4-methyl pyrazole, cyclosporin, clomethiazole, cimetidine, itraconazole, fluconazole, miconazole, fluvoxamine, fluoxetine, nefazodone, sertraline, indinavir, nelfinavir, amprenavir, fosamprenavir, saquinavir, lopinavir, delavirdine, erythromycin, VX-944, and VX-497 (Merimebodib). Preferred CYP inhibitors include ritonavir, ketoconazole, troleandomycin, 4-methyl pyrazole, cyclosporin, and clomethiazole;

Glucocorticoids: hydrocortisone, cortisone, prednisone, prednisolone, methylprednisolone, triamcinolone, paramethasone, betamethasone, and dexamethasone.

HCV Protease Inhibitors: for example ACH-1625 and ACH-2684. U.S. Pat. No. 7,906,619 is hereby incorporated for its teachings regarding anti-HCV compounds. U.S. patent application Ser. No. 12/635,270 at pages 52-167 and Ser.

No. 12/635,049 at pages 43-92 are hereby incorporated by reference for their teachings regarding anti-HCV compounds, ACH 1625 and ACH 2684 (Achillion), ABT-450 (Abbott), ACL-181 and AVL-192 (Avila), BI-335 (Boehringer Ingelheim), BMS-032 (Bristol Meyers Squibb), boceprevir (Merck), TMC-435, MK-7152 (Merck), GS-9256 (Gilead), GS-9451 (Gilead), R7227 (Intermune), VX-500 (Vertex), VX-950 (telaprevir, Vertex), VX-985 (Vertex), TMC-435 (Tibotec), GW-433908 (prodrug of Amprenavir, Glaxo/Vertex), indinavir (CRIXIVAN, Merck), ITMN-191 (Intermune/Array Biopharma), BILN 2061 (Boehringer-Ingelheim), TMC435350 (Tibotec/Medivir), BI 201335 (Boehringer Ingelheim), PHX-1766 (Phenomix), MK-7009 (Merck), narlaprevir (SCH900518, Schering)

Hematopoietins: hematopoietin-1 and hematopoietin-2. Other members of the hematopoietin superfamily such as the various colony stimulating factors (e.g. G-CSF, GM-CSF, M-CSF), Epo, and SCF (stem cell factor)

Homeopathic Therapies: Milk Thistle, silymarin, ginseng, glycyrrhizin, licorice root, schisandra, vitamin C, vitamin E, beta carotene, and selenium Immunomodulatory compounds: thalidomide, IL-2, hematopoietins, IMPDH inhibitors, for example Merimepodib (Vertex Pharmaceuticals Inc.), interferon, including natural interferon (such as OMNIFERON, Viragen and SUMIFERON, Sumitomo, a blend of natural interferons), natural interferon alpha (ALFERON, Hemispherx Biopharma, Inc.), interferon alpha nl from lymphblastoid cells (WELLFERON, Glaxo Wellcome), oral alpha interferon, Peg-interferon, Peg-interferon alfa 2a (PEGASYS, Roche), recombinant interferon alfa 2a (ROFERON, Roche), inhaled interferon alpha 2b (AERX, Aradigm), Peg-interferon alpha 2b (ALBUFERON, Human Genome Sciences/Novartis, PEGINTRON, Schering), recombinant interferon alfa 2b (INTRON A, Schering), pegylated interferon alfa 2b (PEG-INTRON, Schering, VIRAFERONPEG, Schering), interferon beta-1a (REBIF, Ares-Serono, Inc. and Pfizer), consensus interferon alpha (INFERGEN, Intermune), interferon gamma-1b (ACTIMMUNE, Intermune, Inc.), un-pegylated interferon alpha, alpha interferon, and its analogs, and synthetic thymosin alpha 1 (ZADAXIN, SciClone Pharmaceuticals Inc.), and lamdba interferon (BMS)

Immunosupressants: sirolimus (RAPAMUNE, Wyeth)

Interleukins: (IL-1, IL-3, IL-4, IL-5, IL-6, IL-10, IL-11, IL-12), LIF, TGF-beta, TNF-alpha) and other low molecular weight factors (e.g. AcSDKP, pEEDCK, thymic hormones, and minicytokines)

Interferon Enhancers: EMZ702 (Transition Therapeutics)

IRES inhibitors: VGX-410C (VGX Pharma)

Monoclonal and Polyclonal antibodies: XTL-6865 (HEPX-C, XTL), HuMax-HepC (Genmab), Hepatitis C Immune Globin (human) (CIVACIR, Nabi Biopharmceuticals), XTL-002 (XTL), Rituximab (RITUXAN, Genentech/IDEC)

Nucleoside analogues: IDX-184 (Idenix), PSI-7977 and PSI-938 (Pharmasset), INX-189 (Inhibitex), R7128 (Roche), R7348 (Roche), GS-6620 (Gilead), TMC-649 (Tibotec), Lamivudine (EPIVIR, 3TC, GlaxoSmithKline), MK-0608 (Merck), zalcitabine (HIVID, Roche US Pharmaceuticals), ribavirin (including COPEGUS (Roche), REBETOL (Schering), VILONA (ICN Pharmaceuticals, and VIRAZOLE (ICN Pharmaceuticals), isatoribine (Anadys Pharmaceuticals), ANA971 (Anadys Pharmaceuticals), ANA245 (Anadys Pharmaceuticals), and viramidine (ICN), an amidine prodrug of ribavirin. Combinations of nucleoside analogues may also be employed.

Non-nucleoside inhibitors: PSI-6130 (Roche/Pharmasset), ABT-333 and ABT-072 (Abbott), delaviridine (RESCRIPTOR, Pfizer), PF-868554 (Pfizer), GSK-852 (GlaxoSmithKline), IDX-325 (Idenix), ANA-598 (Anadys), VX-222 and VX-759 (Vertex), MK-3281 (Merck), BI-127 (Boehringer Ingelheim), BMS-325 (Bristol Meyers), and HCV-796 (Viropharm)

NS4a inhibitors: for example ACH-1095. US patent application no. US2007/0004711 is hereby incorporated by reference in its entirety for its teachings regarding HCV inhibitors and U.S. patent application Ser. No. 12/125,554 at pages 45-90 is hereby incorporated by reference for its teachings regarding HCV inhibitors.

NS4b inhibitors: clemizole (Arrow Therapeutics)

NS5a inhibitors: A-382 (Arrow Therapeutics), BMS-790052 (BMS) NS5b inhibitors: INX-181, IDX-375, MK-3281, PSI-7977, PSI-7851, PSI-938, RG-9190, VX-222 (Vertex), and BMS-791325 (Bristol Meyers Squibb).

P7 protein inhibitor: amantadine (SYMMETREL, Endo Pharmaceuticals, Inc.)

Polymerase inhibitors: Filibuvir (PF-00868554, Pfizer), NM283 (valopicitabine) (Idenix), JTK 003 (AKROS Pharma), HCV-796 (ViroPharma/Wyeth), IDX184 (Idenix), VCH-916 (Vertx), R7128 (PSI6130, Roche), R1626 (Roche), MK-3281 (Merck), PSI-7851 (Pharmasset), ANA598 (Anadys), BI207127 (Boehringer-Ingelheim), GS 9190 (Gilead).

RNA interference: SIRNA-034 RNAi (Sirna Therapeutics) and ISI 14803 (Isis Pharmaceutical/Elan)

Therapeutic Vaccines: $IC_{41}$ (Intercell), IMN-0101 (Imnogenetics), GI 5005 (Globeimmune), Chronvac-C (Tripep/Inovio), ED-002 (Imnogenetics), Hepavaxx C (ViRex Medical)

TNF agonists: adalimumab (HUMIRA, Abbott), entanercept (ENBREL, Amgen and Wyeth), infliximab (REMICADE, Centocor, Inc.)

Tubulin inhibitors: Colchicine

Sphingosine-1-phosphate receptor modulators: FTY720 (Novartis)

TLR agonists: ANA-975 (Anadys Pharmaceuticals), TLR7 agonist (Anadys Pharmaceuticals), CPG10101 (Coley), and TLR9 agonists including CPG 7909 (Coley).

Vaccines: HCV/MF59 (Chiron), $IC_{41}$ (Intercell), E-1 (Innogenetics)

Patients receiving hepatitis C medications are typically given interferon together with another active agent. Thus methods of treatment and pharmaceutical combinations in which a compound of The invention is provided together with an interferon, such as pegylated interferon alfa 2a, as the additional active agents are included as embodiments. Similarly methods and pharmaceutical combinations in which ribavirin is an additional active agent are provided herein.

Methods of inhibiting HCV replication in vivo comprising providing a compound or pharmaceutically acceptable salt of Formula I to a patient infected with HCV, a concentration of the compound or salt of Formula I sufficient to inhibit HCV replicon replication in vitro are included herein. In this instance the concentration includes an in vivo concentration, such as a blood or plasma concentration. The concentration of compound sufficient to inhibit HCV replicon replication in vitro may be determined from an assay of replicon replication such as the assay provided in Example 9, herein.

Methods of treatment include providing certain dosage amounts of a compound or pharmaceutically acceptable salt of Formula I to a patient. Dosage levels of each active agent of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single unit dosage form will vary depending upon the patient treated and the particular mode of administration. In certain embodiments about 0.1 mg to about 2000 mg, from about 10 mg to about 1500 mg, from about 100 mg to about 1000 mg, from about 200 mg to about 800 mg, or from about 300 to about 600 mg of a compound of Formula I and optionally from about 0.1 mg to about 2000 mg, from about 10 mg to about 1500 mg, from about 100 mg to about 1000 mg, from about 200 mg to about 800 mg, or from about 300 to about 600 mg of a compound of an additional active agent, for example an NS3a protease inhibitor such as a compound of Formula II are provided daily to a patient. It is preferred that each unit dosage form contains less than 1200 mg of active agent in total. Frequency of dosage may also vary depending on the compound used and the particular disease treated. However, for treatment of most infectious disorders, a dosage regimen of 4 times daily or less is preferred and a dosage regimen of 1 or 2 times daily is particularly preferred.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease in the patient undergoing therapy.

Packaged Formulations

Methods comprising providing a compound or salt of Formula I in a container together with instructions for using the compound to treat a patient suffering from Hepatitis C infection are included herein.

Packaged pharmaceutical compositions/combinations are also included herein. Such packaged combinations include a compound of Formula I in a container together with instructions for using the combination to treat or prevent a viral infection, such as a hepatitis C infection, in a patient.

The packaged pharmaceutical composition/combination may include one or more additional active agents. In certain embodiments the additional active agent is an NS3a protease inhibitor, such as a compound of Formula II.

The packaged pharmaceutical combination may include a compound or pharmaceutically acceptable salt of Formula I and the additional active agent provided simultaneously in a single dosage form, concomitantly in separate dosage forms, or provided in separate dosage forms for administration separated by some amount of time that is within the time in which both the compound of Formula I and the additional active agent are within the bloodstream of the patient.

The packaged pharmaceutical combination may include a compound or pharmaceutically acceptable salt of Formula I provided in a container with an additional active agent provided in the same or separate container, with instructions for using the combination to treat an HCV infection in a patient.

EXAMPLES

Abbreviations

The following abbreviations are used in the reaction schemes and synthetic examples, which follow. This list in not meant to be an all-inclusive list of abbreviations used in the application as additional standard abbreviations, which are readily understood by those skilled in the art of organic synthesis, may also be used in the synthetic schemes and examples.

Ac acetyl

ACN acetonitrile aq. aqueous

BOC t-butoxycarbonyl

DCM dichloromethane

DIEA N,N-diisopropylethylamine

DIPEA N,N-diisopropylethylamine

DME 1,2-dimethoxyethane

DMF N,N-dimethylformamide dppf 1,1'-bis(diphenylphosphino)ferrocene

EDCI N-(3-Dimethylaminopropyl)-N-ethylcarbodiimide hydrochloride

Et ethyl $Et_2O$ diethyl ether

FCC flash column chromatography

HATU O-(7-azabenzotriazol-1-yl)-N,N,N',N'-tetramethyl-uronium hexafluorophosphate MTBE methyl tert-butyl ether PTLC preparative thin layer chromatography rt room temperature TEA triethylamine TFA trifluoroacetic acid THF tetrahydrofuran TPP triphenylphosphine General Considerations All nonaqueous reactions were performed under an atmosphere of dry argon gas using oven-dried glassware and anhydrous solvents. The progress of reactions and the purity of target compounds were determined using one of the following two HPLC methods: (1) Waters AQUITY UPLC BEH C18 1.7 µm 2.1×50 mm column with an isocratic elution of 0.24 min at 90:10 water:acetonitrile containing 0.05% formic acid followed by a 4.26-min linear gradient elution from 90:10 to 10:90 at a flow rate of 1.0 mL/min with UV (PDA), ELS, and MS (SQ in APCI mode) detection (method 1); and (2) Waters AQUITY UPLC BEH C18 1.7 µm 2.1×50 mm column with an isocratic elution of 0.31 min at 95:5 water:acetonitrile containing 0.05% formic acid followed by a 17.47-min linear gradient elution from 95:5 to 5:95 at a flow rate of 0.4 mL/min with UV (PDA), ELS, and MS (SQ in APCI mode) detection (method 2).

Target compounds were purified via preparative reverse-phase HPLC using a YMC Pack Pro C18 5 µm 150×20 mm column with an isocratic elution of 0.35 min at 95:5 water:acetonitrile containing 0.1% trifluoroacetic acid followed by a 23.3-min linear gradient elution from 95:5 to 5:95 at a flow rate of 18.9 mL/min with UV and mass-based fraction collection.

GENERAL SYNTHETIC SCHEME
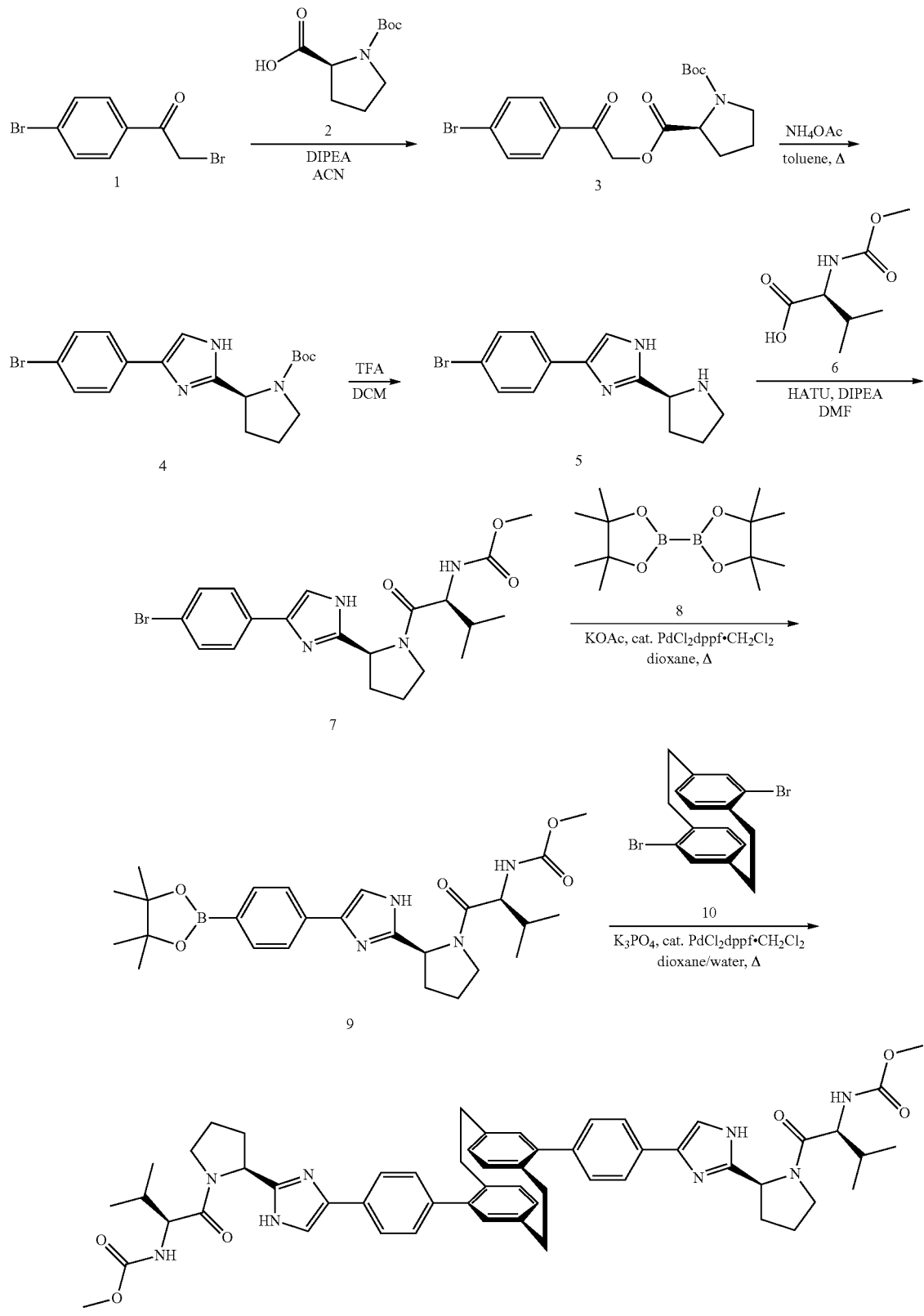

Example 1

Synthesis of Compound 10

Compound 10 was prepared via bromination of [2.2] paracyclophane as outlined previously (Reich, H. J.; Cram, D. J. *J. Am. Chem. Soc.* 1969, 91, 3527-3533; Reich, H. J.; Cram, D. J. *J. Am. Chem. Soc.* 1969, 91, 3534-3543). Compounds 1, 2, 6, 8, and 10 can be obtained from commercial sources. Compounds 3-7 and 9 were prepared using general synthetic methods known in the art.

Example 2

Synthesis of Compound 11

A deoxygenated (argon) mixture of 9 (284.2 mg), 10 (52.3 mg), $K_3PO_4$ (248.1 mg), and $PdCl_2dppf·CH_2Cl_2$ (7.4 mg) in dioxane/water (5.5. mL/0.55 mL) was irradiated in a microwave for 2 h at 80° C. The resulting mixture was evaporated under reduced pressure and the remaining solid was extracted with DCM. This crude material was purified by PTLC (20 cm×20 cm×2000 μm glass plates; eluted with 45:50:5 v/v/v DCM:EtOAc:MeOH, $R_f$ 0.28) to give 75.3 mg of 11. The purity of 11 was determined via analytical reverse-phase HPLC using a 3.5-min gradient elution of increasing concentrations of ACN in water (10-90%) containing 0.05% formic acid with a flow rate of 1.0 mL/min on a Waters AQUITY UPLC BEH C18 1.7 μm 2.1×50 mm column with UV (PDA), ELS, and MS (SQ in APCI mode) detection. HPLC: $t_R$ 1.57 min (98% purity). MS m/z calculated for $C_{56}H_{64}N_8O_6$ ([M]+), 945. found, 946 ([M+1]+).

Example 3

Synthesis of Dimethyl ((2S,2'S)-((2S,2'S,3aS,3a'S,7aS,7a'S)-2,2'-(5,5'-(tricyclo[8.2.2.2$^{4,7}$]hexadeca-4,6,10,12,13,15-hexaene-5,11-diyl)bis(1H-benzo[d]imidazole-5,2-diyl))bis(octahydro-1H-indole-2,1-diyl))bis(3-methyl-1-oxobutane-2,1-diyl))dicarbamate (20)

Step 1

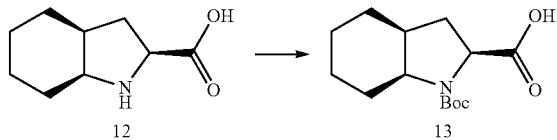 [SMILES: O=C(O)[C@@H]1C[C@@H]2CCCC[C@@H]2N1 ; CC(C)(C)OC(=O)N1[C@H](C(=O)O)C[C@@H]2CCCC[C@@H]21]

To a stirred solution of (2R,3aS,7aS)-octahydro-1H-indole-2-carboxylic acid (250 g, 1.0 equiv) (12) in THF (3 L) and water (1.5 L) at 0° C., was added dropwise a cooled aq solution of 2.5 M NaOH (1 L). The reaction mixture was stirred for 15 min at the same temperature. Then di-tert-butyl dicarbonate (1.3 equiv) was added dropwise, maintaining the temperature at 0° C. The resulting reaction mixture was stirred at rt for 12 h. The reaction mixture was washed with MTBE (3 times). The aq phase was acidified with 1 M aq citric acid and extracted with ethyl acetate (3 times). The combined organic layers were dried over sodium sulphate and concentrated to dryness to give (2R,3aS,7aS)-1-(tert-butoxycarbonyl)octahydro-1H-indole-2-carboxylic acid (368 g) (13).

Step 2

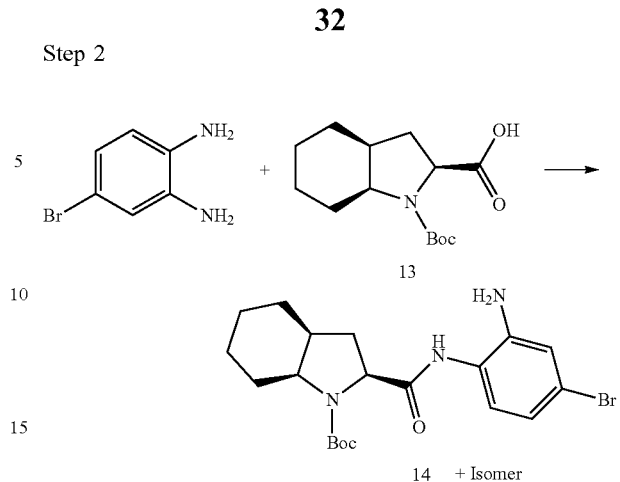

To a stirred solution of 4-bromo-1,2-diaminobenzene (23.1 g, 1.2 equiv), (2R,3aS,7aS)-1-(tert-butoxycarbonyl)octahydro-1H-indole-2-carboxylic acid (26.9 g, 1.0 equiv) 13, and EDCI (23.6 g, 1.2 equiv) in ACN (600 mL) at 0° C. was added DIEA (21.5 mL, 1.3 equiv) dropwise. The reaction mixture was stirred for additional 1 h after completion of addition. Water (1.2 L) was added and the reaction mixture was stirred overnight. The solid powder (14) was collected, washed with water, and dried for use in the next step without further purification (39.1 g).

Step 3

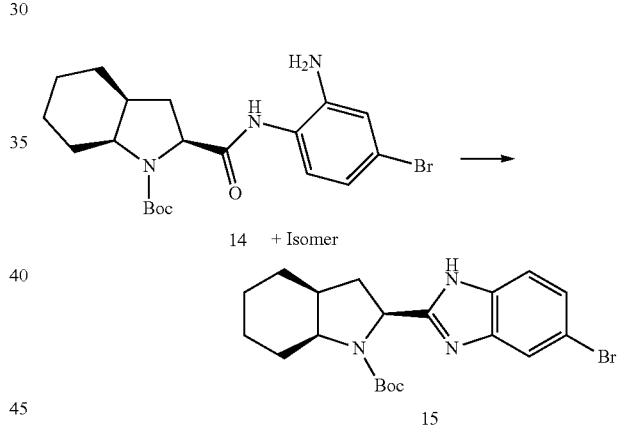

An isomeric mixture (14) of (2S,3aS,7aS)-tert-butyl 2-((2-amino-4-bromophenyl)carbamoyl)octahydro-1H-indole-1-carboxylate and (2S,3aS,7aS)-tert-butyl 2-((2-amino-5-bromophenyl)carbamoyl)octahydro-1H-indole-1-carboxylate (160 g, 0.36 mol) was dissolved in acetic acid (480 mL) and the reaction mixture was stirred at 65° C. until the starting materials were consumed (as judged by LC-MS analysis). The reaction was cooled to rt and the solvent was removed under vacuum. The remaining residue was dissolved in ethyl acetate (500 mL) and aq ammonia (100 mL) was added carefully. Additional water (100 mL) was added and the organic layer was separated and collected. The aq phase was extracted with ethyl acetate (2×300 mL). The combined organic phase was washed with water (200 mL), followed by brine (200 mL), and dried over $MgSO_4$. The solution was concentrated and the remaining residue was purified by silica gel column chromatography (hexanes/ ethyl acetate) to afford (2S,3aS,7 aS)-tert-butyl 2-(6-bromo-1H-benzo[d]imidazol-2-yl)octahydro-1H-indole-1-carboxylate (15) (140 g).

Step 4

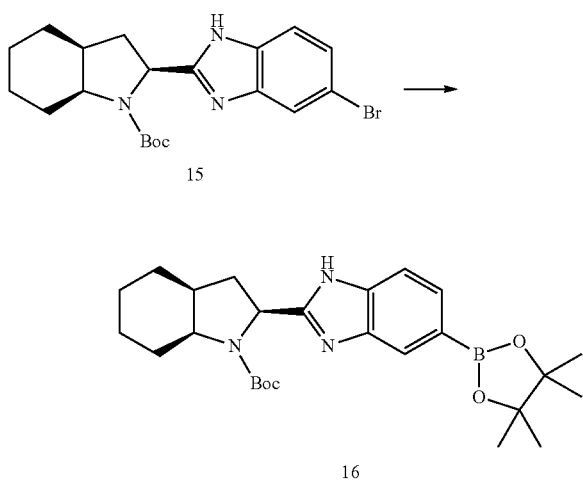

Under an atmosphere of argon, a mixture of (2S,3aS,7aS)-tert-butyl 2-(6-bromo-1H-benzo[d]imidazol-2-yl)octahydro-1H-indole-1-carboxylate (15) (30 g, 1.0 equiv), bis(pinacolato)diborane (27.2 g, 1.5 equiv), potassium acetate (21 g, 3.0 equiv), and Pd(dppf)Cl$_2$ (5.7 g, 0.098 equiv) in anhydrous 1,4-dioxane (300 mL) was heated at 80-90° C. for ~4 h (until the reaction was complete as judged by LC-MS). The cooled (rt) reaction mixture was diluted with ethyl acetate (300 mL), stirred with activated carbon (60 g) for 1 h, and filtered through a pad of Celite. The filtrate was concentrated under reduce pressure and the resulting brown foam was purified by silica gel column chromatography (hexanes/ethyl acetate, 5:1→1:2 v/v) to give (2S,3 aS,7aS)-tert-butyl 2-(6-(4,4,5,5-tetramethyl-1,3,2-dioxaborolan-2-yl)-1H-benzo[d]imidazol-2-yl)octahydro-1H-indole-1-carboxylate as an off-white solid) (16).

Step 5

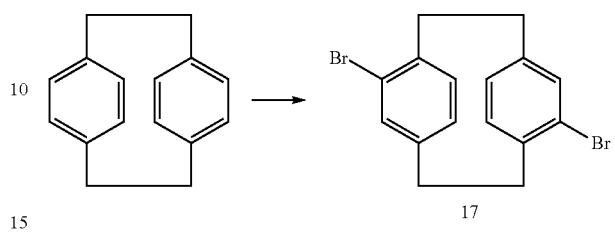

A mixture of Br$_2$ (82.8 g) and iron powder (4.6 g) in DCM (1.6 L) was stirred at rt for 1 h. To this mixture was added, in one portion, a slurry of [2.2]paracyclophane (200 g, 1.0 equiv) in DCM. The resulting mixture was heated to reflux, and to it was added slowly a solution of Br$_2$ (228 g) in DCM (400 mL) over a 3-h period. After this addition was complete, the reaction mixture continued to reflux for 3 h, was allowed to cool to rt with stirring overnight, was washed with 5% w/v aq Na$_2$S$_2$O$_3$ (2 L) and water (2 L), dried (MgSO$_4$), and evaporated to dryness. The isolated crude solid was dissolved in hot toluene (1.2 L, ~100° C.), allowed to cool slowly overnight to rt with stirring, and further cooled to 5° C. for 3 h. The resulting solid was collected and washed with cold toluene (~100 mL) to afford 4,16-dibromo[2.2]paracyclophane (17) (83 g). $^1$H NMR (300 MHz, CDCl$_3$, rt): δ 2.79-3.00 (m, 4H), 3.10-3.21 (m, 2H), 3.44-3.54 (m, 2H), 6.44 (d, J=8.0 Hz, 2H), 6.51 (d, J=2.0 Hz, 2H), 7.14 (dd, J=8.0 Hz, 2.0 Hz, 2H).

Step 6

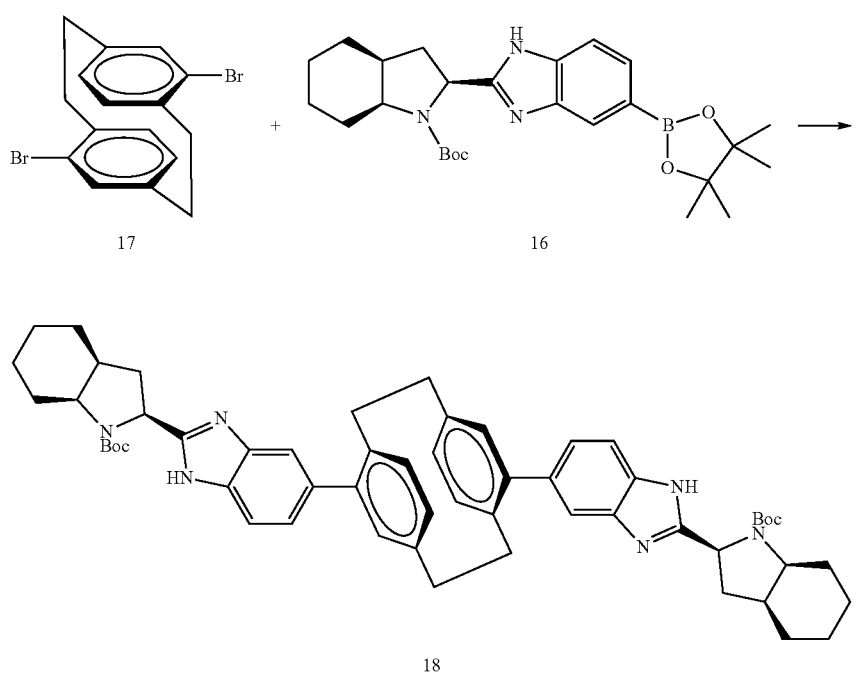

Under an atmosphere of argon, a mixture of 4,16-dibromo[2.2]paracyclophane (17) (20 g, 1.0 equiv), (2S,3aS,7aS)-tert-butyl 2-(6-(4,4,5,5-tetramethyl-1,3,2-dioxaborolan-2-yl)-1H-benzo[d]imidazol-2-yl)octahydro-1H-indole-1-carboxylate (64 g, 2.5 equiv), Cs$_2$CO$_3$ (16) (44.5 g, 2.5 equiv), Pd(PPh$_3$)$_4$ (3.16 g, 0.05 equiv), DMF (500 mL), and water (25 mL) was heated at 130° C. for ~2-3 h (until the reaction was complete as judged by LC-MS). The reaction mixture was allowed to cool to rt and filtered through a pad of silica gel (30 g) layered with Celite. This pad was washed with DMF (2×50 mL) and the combined filtrates were added to stirred water (2.5 L) to give a pale yellow precipitate. This solid was collected by filtration, washed with water (1 L) and ACN (500 mL), and dissolved in a mixture of DCM (250 mL) and MeOH (25 mL). To this solution was added ACN (250 mL) to generate a fine slurry, which was then concentrated under reduce pressure at 30-35° C. to remove ~150 mL of solvent. Another portion of ACN (500 mL) was added and additional solvent (~100 mL) was removed under reduce pressure at 40-45° C. The solid was collected by filtration and dried under vacuum to give (2S,2'S,3aS,3a'S,7aS,7a'S)-di-tert-butyl 2,2'-(5,5'-(tricyclo[8.2.2.2$^{4,7}$]hexadeca-4,6,10,12,13,15-hexaene-5,11-diyl)bis(1H-benzo[d]imidazole-5,2-diyl))bis(octahydro-1H-indole-1-carboxylate) as a pale yellow powder (33.8 g).

Step 7

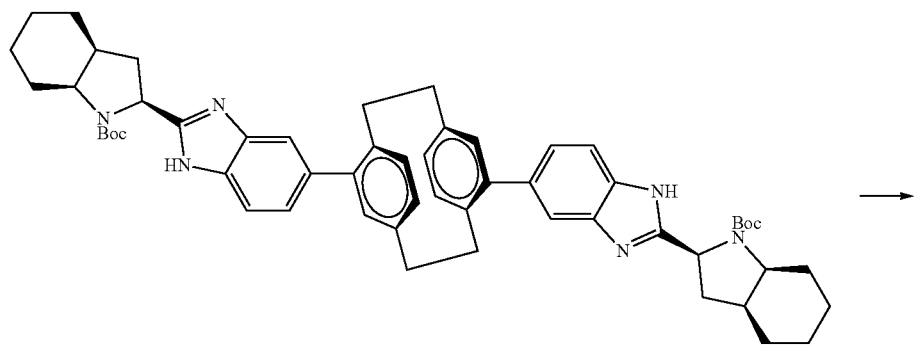

18

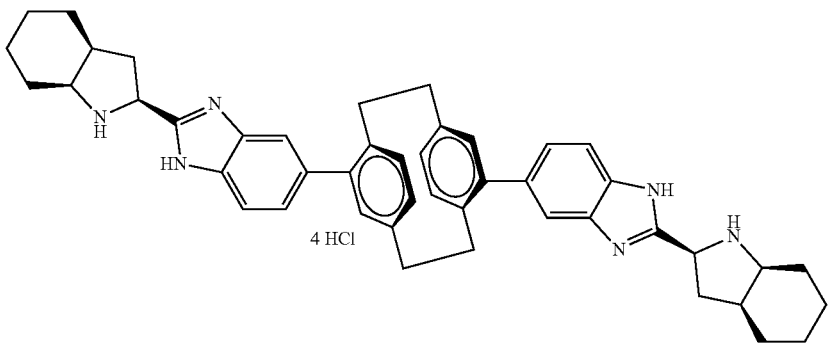

19

To a cooled (0° C.) solution of (2S,2'S,3aS,3a'S,7aS,7a'S)-di-tert-butyl 2,2'-(5,5'-(tricyclo[8.2.2.2$^{4,7}$]hexadeca-4,6,10,12,13,15-hexaene-5,11-diyl)bis(1H-benzo[d]imidazole-5,2-diyl))bis(octahydro-1H-indole-1-carboxylate) (18) (20.33 g, 1.0 equiv) in DCM/MeOH (4/1 v/v, 200 mL) was added a 4 N HCl/dioxane solution (100 mL). The reaction mixture was stirred at rt for 30 min and concentrated under reduce pressure to give a pale yellow powder (19) (21.7 g). The solid obtained was dried under vacuum until residual MeOH was undetectable by $^1$H NMR spectroscopic analysis. This thoroughly dried material was used directly in the next step.

Step 8

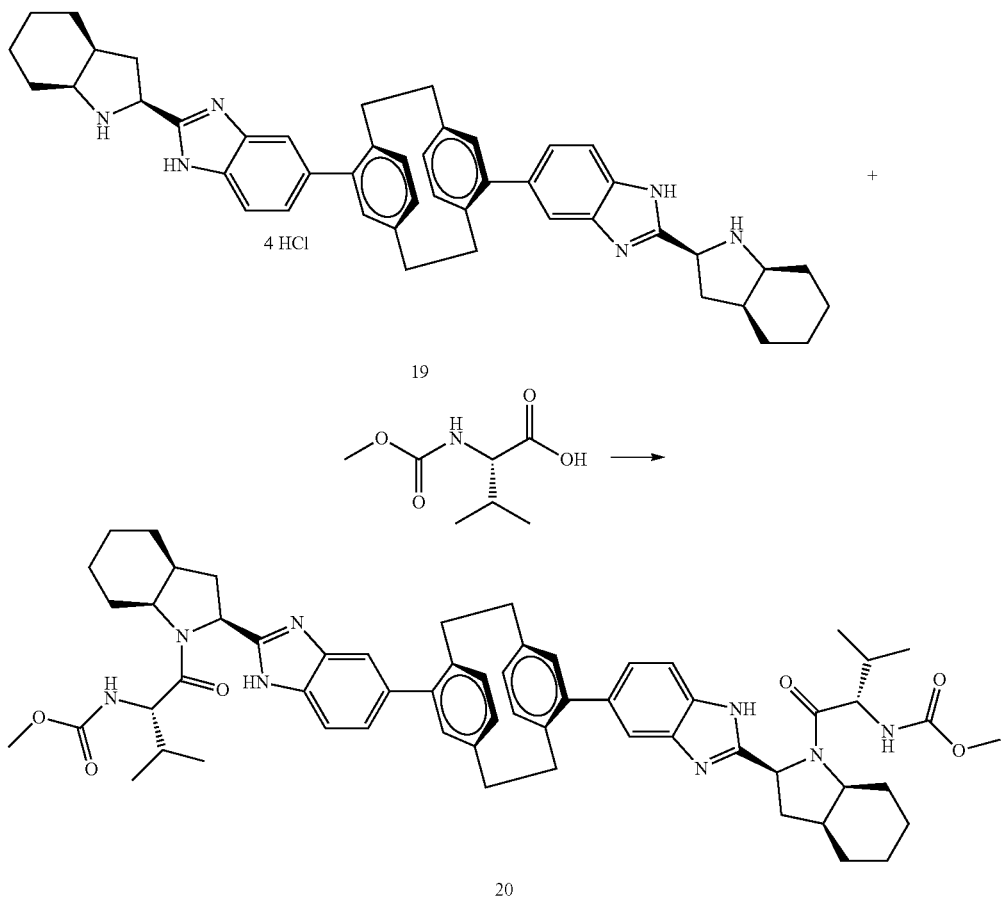

To a mixture of (S)-2-((methoxycarbonyl)amino)-3-methylbutanoic acid (10 g, 2.3 equiv), HOBt monohydrate (8.8 g, 2.3 equiv), and ACN (50 mL) at rt was added EDCI (11.14 g, 2.3 equiv). After stirring 5 min, this activated acid mixture was added to a solution of the hydrochloride salt (19) from above (21.7 g) and DIEA (32 mL, 7.2 equiv) in DMF (250 mL). The reaction mixture was stirred at rt until the reaction was judged as complete by LC-MS analysis (~4 h) and then poured into water (1.2 L) with stirring. The precipitate was collected by filtration, stirred in ACN/water (4:1 v/v, 500 mL) overnight, collected again by filtration, and dried in vacuo to give dimethyl ((2S,2'S)-((2S,2'S,3aS,3a'S,7aS,7a'S)-2,2'-(5,5'-(tricyclo[8.2.2.2$^{4,7}$]hexadeca-4,6,10,12,13,15-hexaene-5,11-diyl)bis(1H-benzo[d]imidazole-5,2-diyl))bis(octahydro-1H-indole-2,1-diyl))bis(3-methyl-1-oxobutane-2,1-diyl))dicarbamate (20) (22.62 g).

$^1$H NMR (300 MHz, DMSO-d$_6$, 120° C.): δ 0.87 (d, J=6.5 Hz, 6H), 0.92 (d, J=6.5 Hz, 6H), 1.20-1.60 (m, 6H), 1.65-2.10 (m, 12H), 2.31 (m, 2H), 2.38-2.52 (m, 2H), 2.54-2.76 (m, 4H), 2.85 (m, 2H), 3.07 (m, 2H), 3.45 (m, 2H), 3.57 (br s, 6H), 4.07 (t, J=8.0 Hz, 2H), 4.34 (m, 2H), 5.28 (t, J=8.5 Hz, 2H), 6.51 (br, 2H), 6.57 (d, J=8.0 Hz, 2H), 6.73 (s, 2H), 6.76 (d, J=8.0 Hz, 2H), 7.33 (d, J=8.5 Hz, 2H), 7.64 (d, J=8.5 Hz, 2H), 7.72 (s, 2H).

Example 4

Synthesis of Dimethyl ((2S,2'S,3R,3'R)-((2S,2'S,3aS,3a'S,7aS,7a'S)-2,2'-(5,5'-(tricyclo[8.2.2.2$^{4,7}$]hexadeca-4,6,10,12,13,15-hexaene-5,11-diyl)bis(1H-benzo[d]imidazole-5,2-diyl))bis(octahydro-1H-indole-2,1-diyl))bis(3-methoxy-1-oxobutane-2,1-diyl))dicarbamate (22)

Step 1

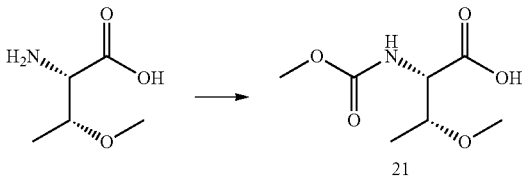

O-Methyl-L-threonine (25 g, 0.19 mol) was dissolved in 1,4-dioxane (125 mL) and cooled to 0° C. An aq 2 M NaOH (22.5 g, 0.56 mol, 3 equiv) solution was then added to the reaction mixture followed by methyl chloroformate (17.4 mL, 0.22 mol, 1.2 equiv) at the same temperature. The reaction mixture was warmed to rt and stirred for 16 h. The reaction mixture was washed with ethyl acetate (500 mL). The aq layer was acidified with 3 N HCl (up to pH 2) and extracted with ethyl acetate (3×250 mL). The combined organic layers were dried over Na₂SO₄ and concentrated to afford the crude product (23 g). Ethyl acetate (46 mL) was added to the crude product and heated at 80° C. to obtain a clear solution. This solution was then cooled to 0° C. The solid obtained was filtered and dried to afford the desired pure product (21) (18.75 g).
Step 2 brine (50 mL), dried over sodium sulphate, and concentrated under reduced pressure. The residue was purified by silica gel column chromatography to give dimethyl ((2S,2'S,3R, 3'R)-((2S,2'S,3aS,3a'S,7aS,7a'S)-2,2'-(5,5'-(tricyclo [8.2.2.2$^{4,7}$]hexadeca-4,6,10,12,13,15-hexaene-5,11-diyl)bis (1H-benzo[d]imidazole-5,2-diyl))bis(octahydro-1H-indole-2,1-diyl))bis(3-methoxy-1-oxobutane-2,1-diyl))dicarbamate

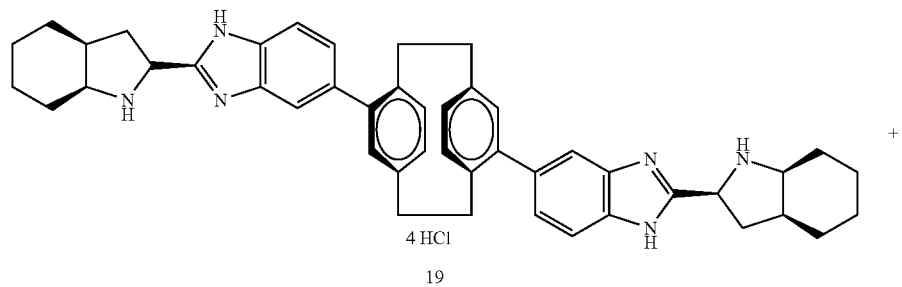

19

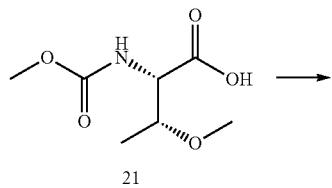

21

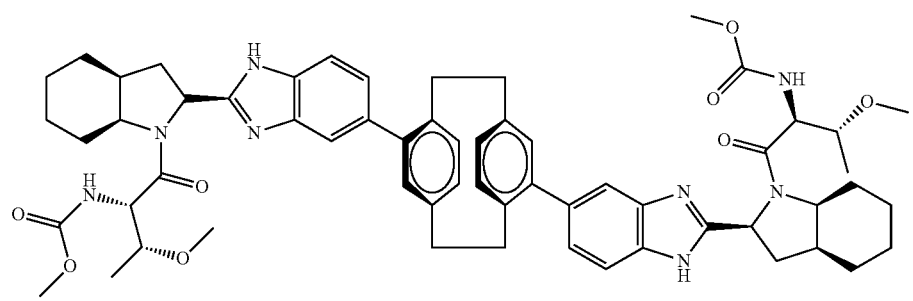

22

DIEA (32.8 mL, 0.192 mol) was added dropwise to a mixture of the hydrochloride salt from above (32.0 g, 0.0384 mol), Moc-O-methyl-L-threonine (18.3 g, 0.0960 mol), and HATU (36.5 g, 0.09604 mol) in DMF (160 mL) at 0° C. The reaction mixture was allowed to warm to rt, stirred for 16 h, and poured into water (1.6 L). The resulting solid was collected by filtration and dissolved in DCM (500 mL). This solution was washed with water (100 mL), washed with

(22) (30 g). $^1$H NMR (400 MHz, DMSO-d₆, rt): δ0.91-1.04 (m, 6H), 1.21-1.59 (m, 6H), 1.64-1.88 (m, 6H), 1.90-2.07 (m, 4H), 2.23-2.49 (m, 6H), 2.62 (m, 2H), 2.85 (m, 2H), 3.08 (m, 2H), 3.19 (s, 3H), 3.20 (s, 3H), 3.42 (m, 2H), 3.57 (s, 6H), 4.15 (apparent t, J=8.0 Hz, 2H), 4.47 (m, 2H), 5.16 (apparent t, J=8.5 Hz, 2H), 6.52 (apparent t, J=8.5 Hz, 2H), 6.75 (s, 2H), 6.82 (m, 2H), 7.41 (m, 2H), 7.71 (apparent t, J=6.0 Hz, 2H), 7.64-7.79 (m, 4H).

Example 5

Synthesis of Dimethyl ((2S,2'S,3R,3'R)-((2S,2'S,3aS,3a'S,7aS,7a'S)-2,2'-(5,5'-(tricyclo[8.2.2.2$^{4,7}$]hexadeca-4,6,10,12,13,15-hexaene-5,11-diyl)bis(1H-benzo[d]imidazole-5,2-diyl))bis(octahydro-1H-indole-2,1-diyl))bis(3-methoxy-1-oxobutane-2,1-diyl))dicarbamate (23)

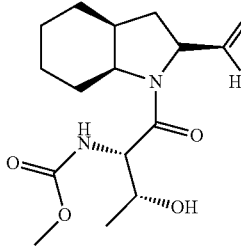
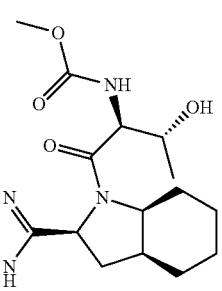

23

Dimethyl ((2S,2'S,3R,3'R)-((2S,2'S,3aS,3a'S,7aS,7a'S)-2,2'-(5,5'-(tricyclo[8.2.2.2$^{4,7}$]hexadeca-4,6,10,12,13,15-hexaene-5,11-diyl)bis(1H-benzo[d]imidazole-5,2-diyl))bis(octahydro-1H-indole-2,1-diyl))bis(3-hydroxy-1-oxobutane-2,1-diyl))dicarbamate was prepared in a manner analogous to that described above for the synthesis of dimethyl ((2S,2'S,3R,3'R)-((2S,2'S,3aS,3a'S,7aS,7a'S)-2,2'-(5,5'-(tricyclo[8.2.2.2$^{4,7}$]hexadeca-4,6,10,12,13,15-hexaene-5,11-diyl)bis(1H-benzo[d]imidazole-5,2-diyl))bis(octahydro-1H-indole-2,1-diyl))bis(3-methoxy-1-oxobutane-2,1-diyl))dicarbamate. $^1$H NMR (400 MHz, DMSO-$d_6$, rt): $^1$H NMR (400 MHz, DMSO-$d_6$, rt): δ0.95-1.04 (m, 6H), 1.20-1.56 (m, 6H), 1.64-1.85 (m, 6H), 1.90-2.09 (m, 4H), 2.25 (m, 2H), 2.32-2.49 (m, 4H), 2.63 (m, 2H), 2.83 (m, 2H), 3.06 (m, 2H), 3.39 (m, 2H), 3.57 (s, 6H), 3.69 (m, 2H), 4.06 (apparent t, J=7.5 Hz, 2H), 4.46 (m, 2H), 4.72 (m, 2H), 5.13 (m, 2H), 6.44-6.57 (m, 2H), 6.68-6.87 (m, 4H), 7.23-7.35 (m, 4H), 7.53-7.78 (m, 4H).

Example 6

Synthesis of Compound 29 Via the Tetraamine Synthetic Route

Step 1

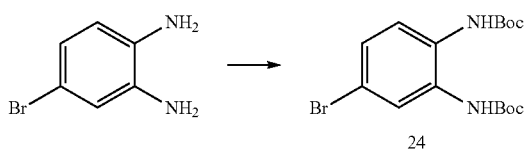 [SMILES: Nc1ccc(Br)cc1N ; CC(C)(C)OC(=O)Nc1ccc(Br)cc1NC(=O)OC(C)(C)C]

1,2-Diamino-4-bromobenzene (10 g, 0.053 mol) was dissolved in DCM (150 mL) and cooled to 0° C. A solution of NaOH (50 mL, 2.5 mol) was added dropwise at the same temperature. After 15 min, di-tert-butyl dicarbonate (58 g, 0.26 mol) was added dropwise at the same temperature. Then the reaction mixture was allowed to warm to room temperature, stirred for 16 h, diluted with DCM (100 mL), and washed with water (100 mL). The organic layer was separated, dried over Na$_2$SO$_4$, and concentrated. The crude material was purified by silica gel column chromatography (petroleum ether/ethyl acetate, 1:1 v/v) to afford the desired product (18 g)

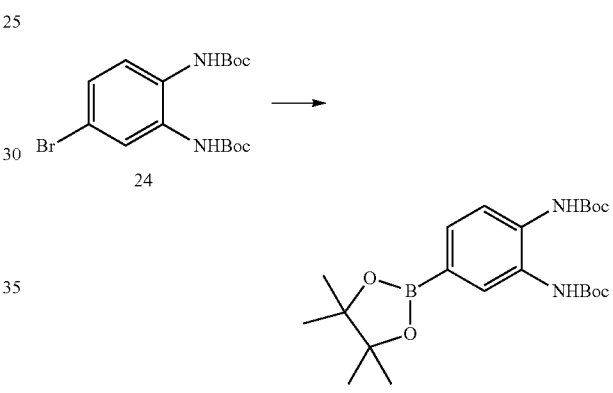

Step 2

Under an atmosphere of argon, a mixture of di-tert-butyl (4-bromo-1,2-phenylene)dicarbamate (24) (18 g, 0.046 mol), bis(pinacolato)diboron (17.7 g, 0.070 mol), potassium acetate (13.66 g, 0.14 mol), and Pd(dppf)Cl$_2$ (3.8 g, 0.0046 mol) in 1,4-dioxane (360 mL) was heated at 85° C. for 16 h. The reaction mixture was then diluted with ethyl acetate (200 mL) and filtered through a bed of Celite. The filtrate was concentrated under reduced pressure and the remaining material was purified by silica gel column chromatography (petroleum ether/ethyl acetate, 80:20 v/v) to afford the desired product (25) (16.0 g).

Step 3

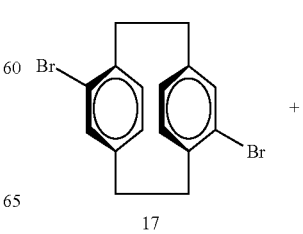

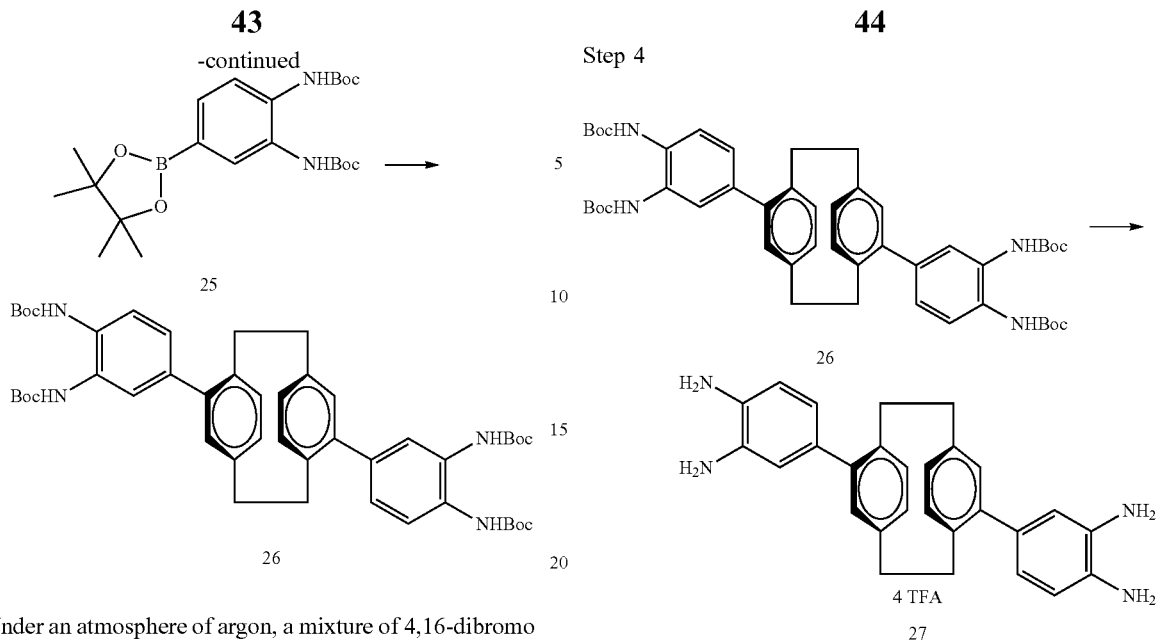

Under an atmosphere of argon, a mixture of 4,16-dibromo[2.2]paracyclophane (17) (6 g, 0.014 mol), di-tert-butyl (4-(4,4,5,5-tetramethyl-1,3,2-dioxaborolan-2-yl)-1,2-phenylene)dicarbamate (17.78 g, 0.032 mol), aq $Cs_2CO_3$ solution (15.98 g, 0.049 mol, in 66 mL water), and $Pd(PPh_3)_4$ (1.33 g, 0.0016 mol) was heated in a sealed tube at 80° C. for 16 h. The reaction mixture was poured into water (250 mL) and the resulting precipitate was collected by filtration and washed with water. This crude material was purified by column chromatography (petroleum ether/ethyl acetate, 6:4 v/v) to afford the desired product (26) (5.0 g).

Step 4

The tetra Boc-protected product from above (26) (10 g) was added to TFA (100 mL) at 0-5° C. After completion of the addition, the reaction mixture was warmed to rt and stirred for 3 h. The reaction mixture was then concentrated and co-evaporated with DCM (3×50 mL). The crude material (27) was used directly in the next step.

Step 5

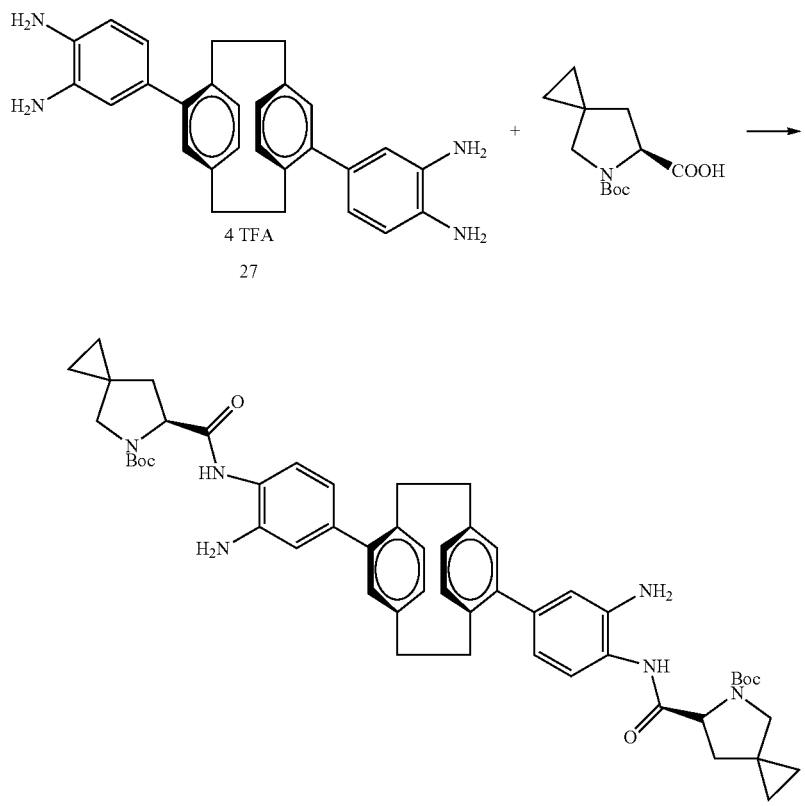

DIEA (1 mL, 0.0125 mol) was added dropwise to a cooled (0° C.) mixture of (S)-5-(tert-butoxycarbonyl)-5-azaspiro [2.4]heptane-6-carboxylic acid (0.5 g, 0.00057 mol), HOBt (0.35 g, 0.0026 mol), EDCI (0.5 g, 0.0026 mol), and the TFA salt (27) from above (0.343 g, 0.0014 mol) in DMF (5 mL) at 0° C. After the addition was complete, the reaction mixture was allowed to warm to rt and stirred for 16 h. The reaction mixture was poured into water and the precipitate (28) was collected by filtration and purified by silica gel column chromatography to give the desired product (0.32 g).

Step 6

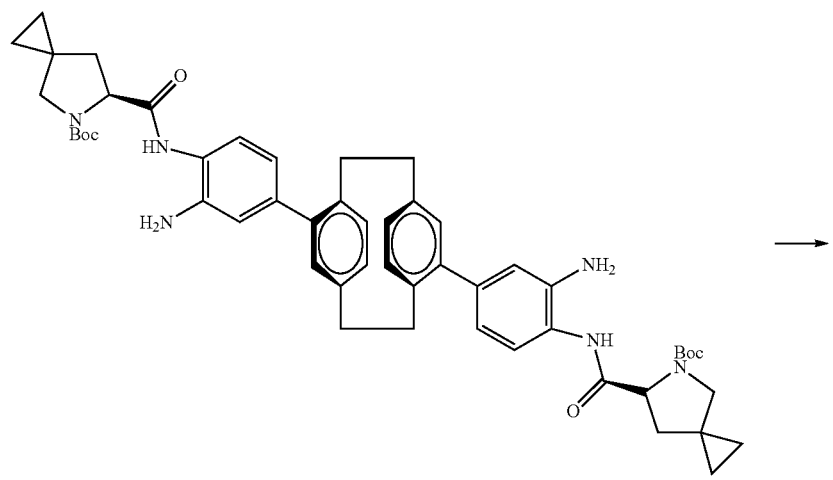

28

29

Acetic acid (5 mL) was added to the diamide product from above (28) (0.32 g, 0.00035 mol) and heated at 45° C. for 4 h. The reaction mixture was evaporated and the residue was diluted with ethyl acetate (95 mL), then washed with aq NaHCO$_3$ (2×25 mL) and water (2×30 mL). The organic layer was separated, dried over Na$_2$SO$_4$, and evaporated under reduced pressure. The crude material was purified by column chromatography to give the desired product (29) (0.2 g).

Step 7

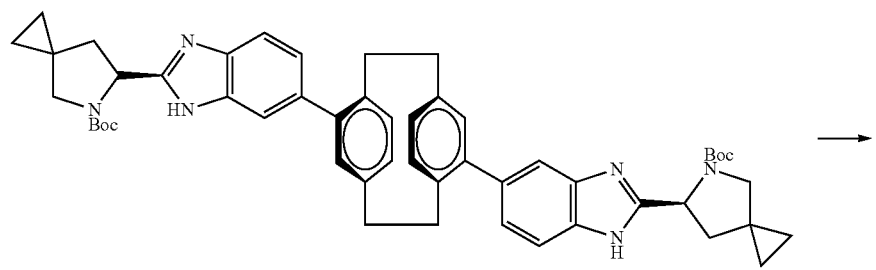

29

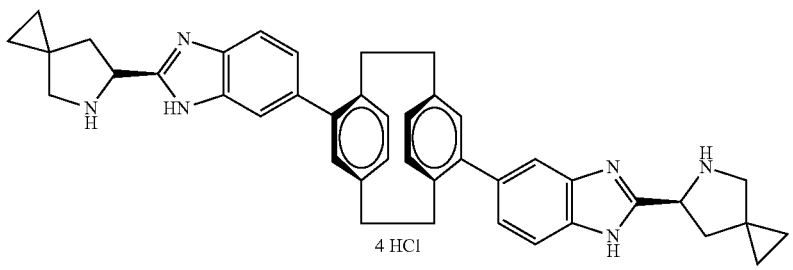

30

The boc-protected product from above (0.09 g) was dissolved in DCM (0.9 mL) and cooled at 0° C. Then 4 N HCl/dioxane (0.9 mL) was added dropwise. The reaction mixture was warmed to rt and stirred for 3 h. Then the volatiles were removed under vacuum and co-evaporated with DCM (3×50 mL). The remaining crude material (30) was used directly in the next step without further purification.

Step 8

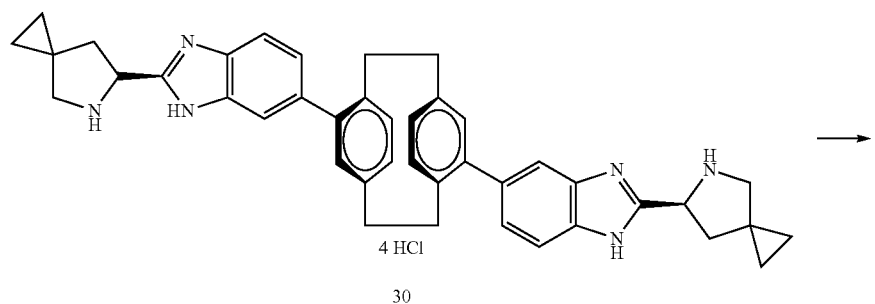

30

0.000033 mol, 2.5 equiv) and EDCI (0.0063 g, 0.000033 mol, 2.5 equiv). DIEA (0.02 mL, 0.00013 mol, 10 equiv) was then added dropwise at the same temperature. The reaction mixture was allowed to warm to rt and stirred for 16 h. The reaction mixture was then poured into water (25 mL) and the precipitated solid was collected by filtration, dried, and purified by silica gel column chromatography to give the desired product (31) (3 mg). $^1$H NMR (400 MHz, DMSO-$d_6$, rt): δ 0.91-1.04 (m, 6H), 1.21-1.59 (m, 6H), 1.64-1.88 (m, 6H), 1.90-2.07 (m, 4H), 2.23-2.49 (m, 6H), 2.62 (m, 2H),

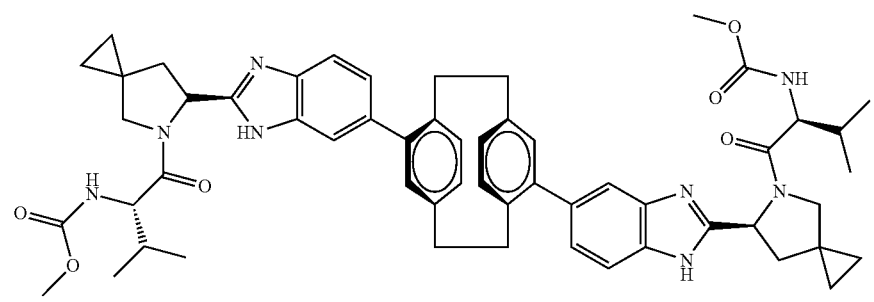

31

The hydrochloride salt (30) from above (0.011 g, 0.0000141 mol, 1.0 equiv) was dissolved in DMF (1 mL) and cooled to 0° C. To this cooled solution were added (S)-2-((methoxycarbonyl)amino)-3-methylbutanoic acid (0.0062 g, 0.000033 mol, 2.5 equiv), HOBt (0.0044 g, 2.85 (m, 2H), 3.08 (m, 2H), 3.19 (s, 3H), 3.20 (s, 3H), 3.42 (m, 2H), 3.57 (s, 6H), 4.15 (apparent t, J=8.0 Hz, 2H), 4.47 (m, 2H), 5.16 (apparent t, J=8.5 Hz, 2H), 6.52 (apparent t, J=8.5 Hz, 2H), 6.75 (s, 2H), 6.82 (m, 2H), 7.41 (m, 2H), 7.71 (apparent t, J=6.0 Hz, 2H), 7.64-7.79 (m, 4H).

Example 7

Synthesis of Ferrocene NS5A Inhibitors (32)

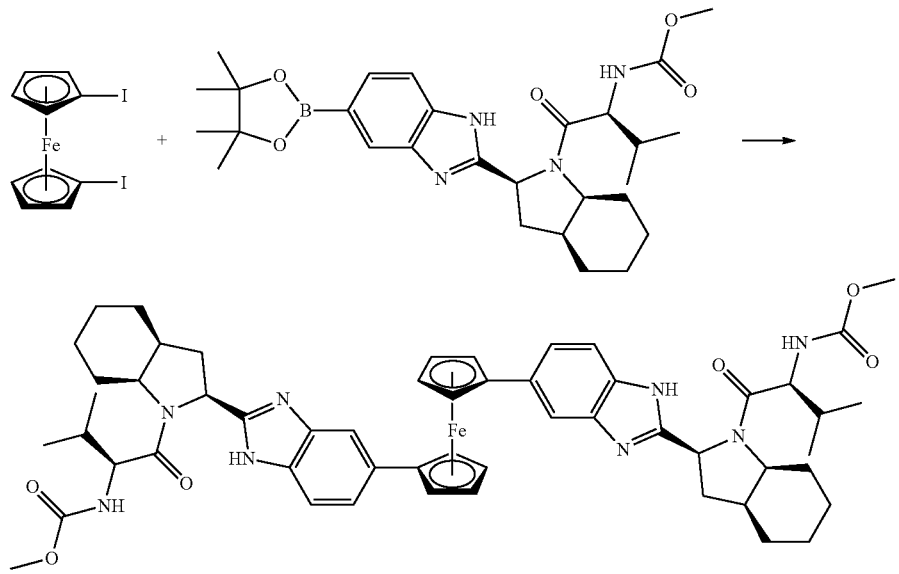

32

Ferrocene compounds are prepared by the method discussed in Butler, I. R., et al., "A Convenient Preparation of Iodoferrocenes," *Polyhedron* (1993) 12: 129-131. To a stirred solution of 1,1'-diiodoferrocene (220 mg, 0.5 mmol) in 1,4-dioxane (10 mL) was added methyl ((S)-3-methyl-1-oxo-1-((2S,3aS,7aS)-2-(5-(4,4,5,5-tetramethyl-1,3,2-dioxaborolan-2-yl)-1H-benzo[d]imidazol-2-yl)octahydro-1H-indol-1-yl)butan-2-yl)carbamate (1.1 g, 4 equiv), $K_3PO_4$ (853 mg, 2 M aq solution, 8 equiv), and $PdCl_2dppf$ (49 mg, 12 mol %) under an atmosphere of argon. The resulting mixture was subjected to microwave irradiation (CEM Discover System) at 80° C. for 1 h. The reaction mixture was allowed to cool to room temperature, filtered, and concentrated in vacuo. The remaining residue was purified by preparative HPLC to give the desired product as the trifluoroacetate salt (43 mg). $^1$H NMR (400 MHz, DMSO-$d_6$, 27° C.): δ 0.63 (d, J=6.5 Hz, 6H), 0.78 (d, J=6.5 Hz, 6H), 1.13-1.49 (m, 6H), 1.55-1.87 (m, 10H), 1.95 (m, 2H), 2.26 (m, 2H), 2.35 (m, 2H), 2.42 (m, 2H), 3.48 (s, 6H), 3.83 (t, J=8.0 Hz, 2H), 4.18 (m, 4H), 4.37 (m, 2H), 4.67 (m, 4H), 5.10 (dd, J=10.0 Hz, 7.5 Hz, 2H), 7.39 (d, J=9.0 Hz, 2H), 7.42 (d, J=9.0 Hz, 2H), 7.45 (d, J=8.0 Hz, 2H), 7.53 (s, 2H).

Example 8

Additional Compounds of Formula I

The following compounds are prepared by the methods set forth in Examples 1-6.

| No. | Structure | EC50 (μM) | | HPLC | | MS |
|---|---|---|---|---|---|---|
| | | NS5A1b | NS5A1b | LC | method | |
| 40 | 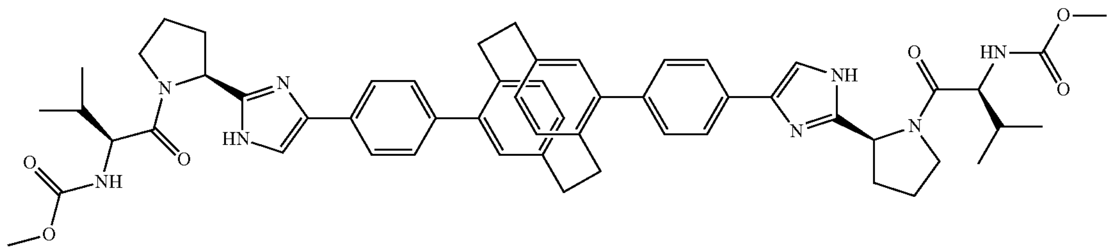 | .000012 | | 1.57 | 1 | 945 |
| 41 | 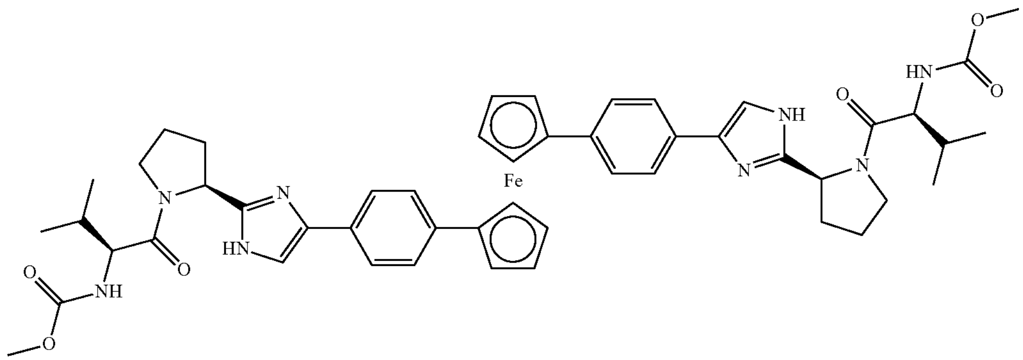 | <0.0032 | 0.00781 | 1.67 | 1 | 923 |
| 42 | 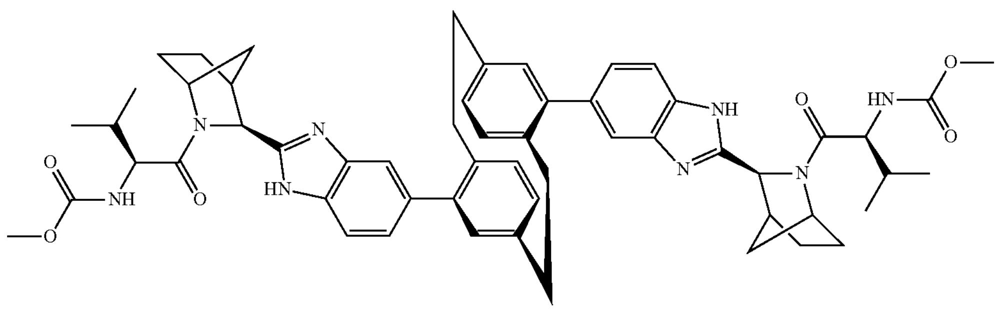 | <0.0032 | 0.0044 | 2.15 | 1 | 945 |

| No. | Structure | EC50 (μM) NS5A1b | EC50 (μM) NS5A1b | HPLC LC | HPLC method | MS |
|---|---|---|---|---|---|---|
| 43 | 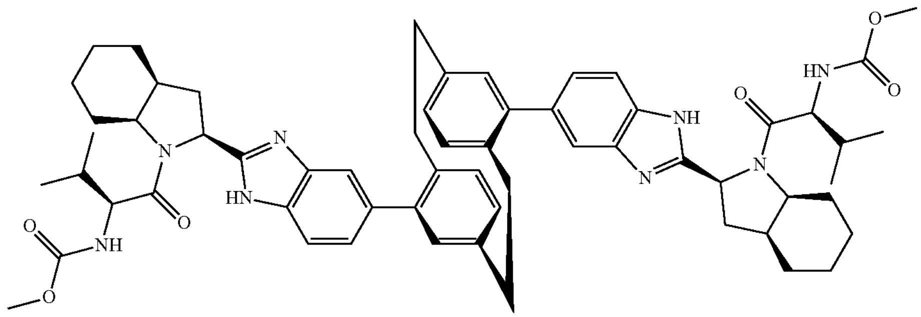 | 0.0285 | | 2.86 | 1 | 1001 |
| 44 | dimethyl ((2S,2′S)-((2S,2′S)-2,2′-(5,5′-(bicyclo[1.1.1]pentane-1,3-diyl)bis(4,1-phenylene))bis(1H-imidazole-5,2-diyl))bis(pyrrolidine-2,1-diyl))bis(3-methyl-1-oxobutane-2,1-diyl))dicarbamate | 0.00408 | | 1.35 | 1 | 805 |
| 45 | 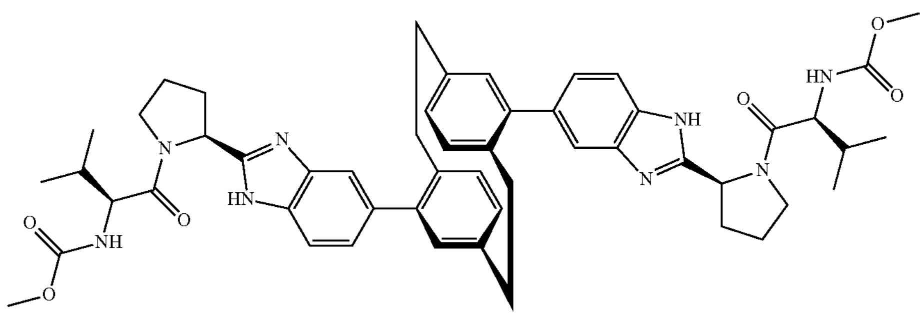 | <0.0032 | | 1.93 | 1 | 893 |

| No. | Structure | EC50 (µM) NS5A1b | EC50 (µM) NS5A1b | HPLC LC | HPLC method | MS |
|---|---|---|---|---|---|---|
| 46 | 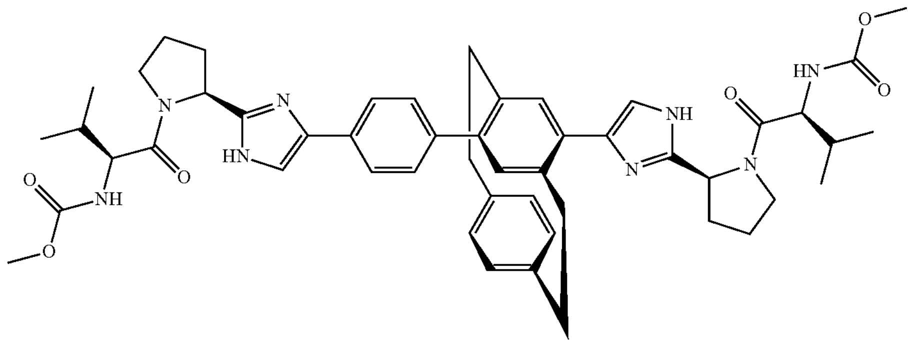 | <0.00317 | | 1.69 | 1 | 870 |
| 47 | 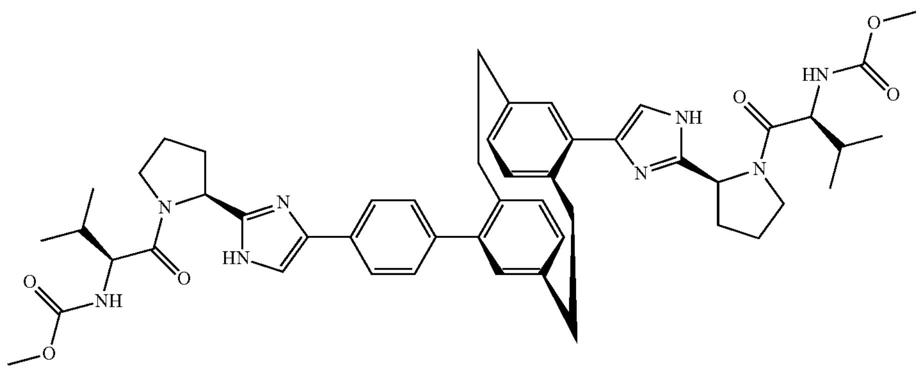 | 0.00502 | | 1.67 | 1 | 870 |
| 48 | 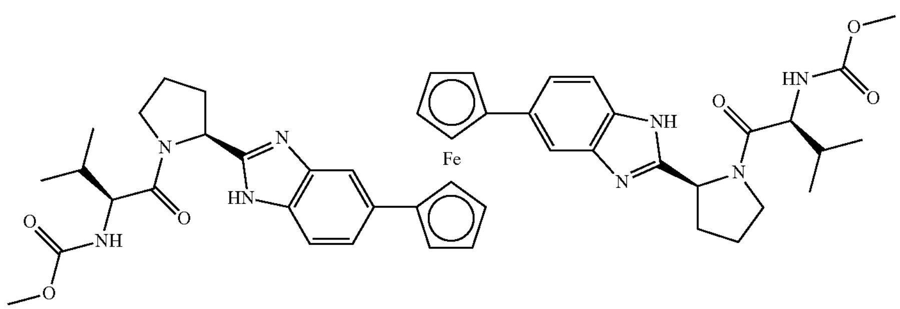 | <0.00317 | | 6.06 | 2 | 871 |

-continued

| No. | Structure | EC50 (μM) NS5A1b | EC50 (μM) NS5A1b | LC | HPLC method | MS |
|---|---|---|---|---|---|---|
| 49 | 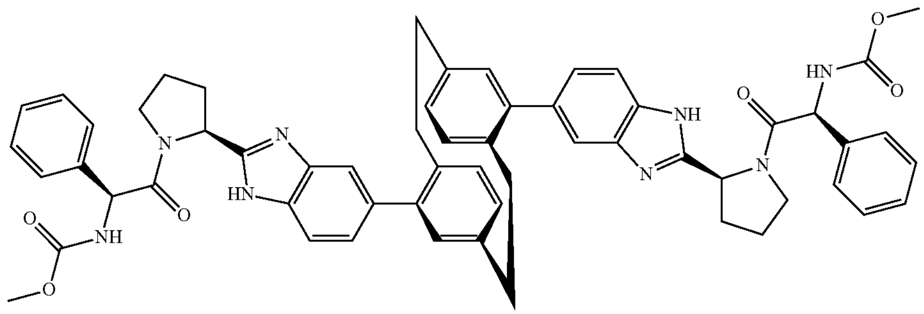 | 0.0102 |  | 1.94 | 1 | 962 |
| 50 | 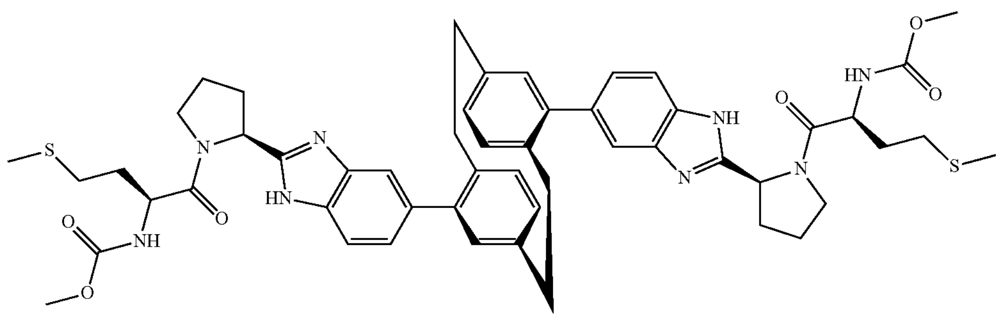 | 0.00841 |  | 1.8 | 1 | 957 |

-continued

| No. | Structure | EC50 (µM) NS5A1b | EC50 (µM) NS5A1b | LC | HPLC method | MS |
|---|---|---|---|---|---|---|
| 51 | 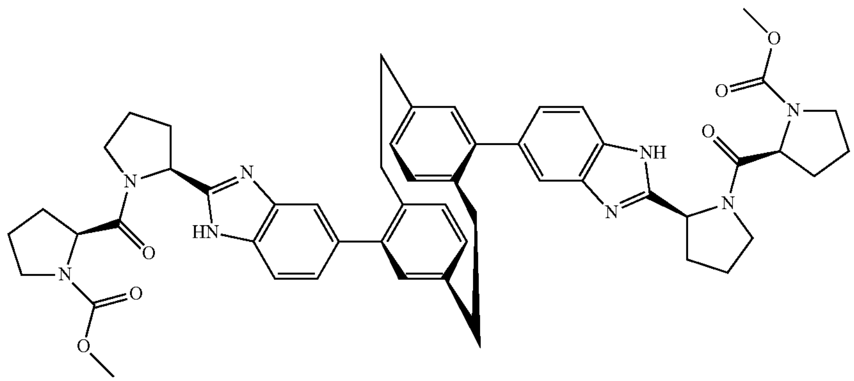 | >1 | | 1.62 | 1 | 889 |
| 52 | 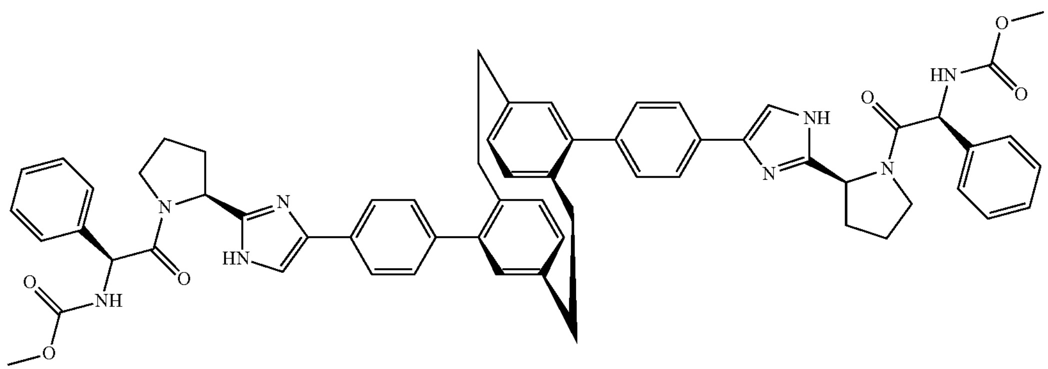 | 0.00983 | | 1.88 | 1 | 1014 |

-continued

| No. | Structure | EC50 (μM) NS5A1b | EC50 (μM) NS5A1b | HPLC LC | HPLC method | MS |
|---|---|---|---|---|---|---|
| 53 | 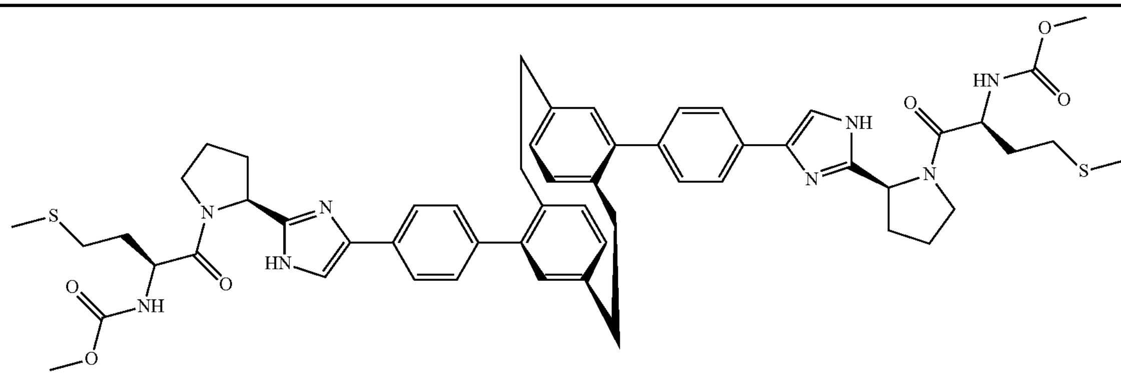 | 0.211 | | 1.78 | 1 | 1009 |
| 54 | 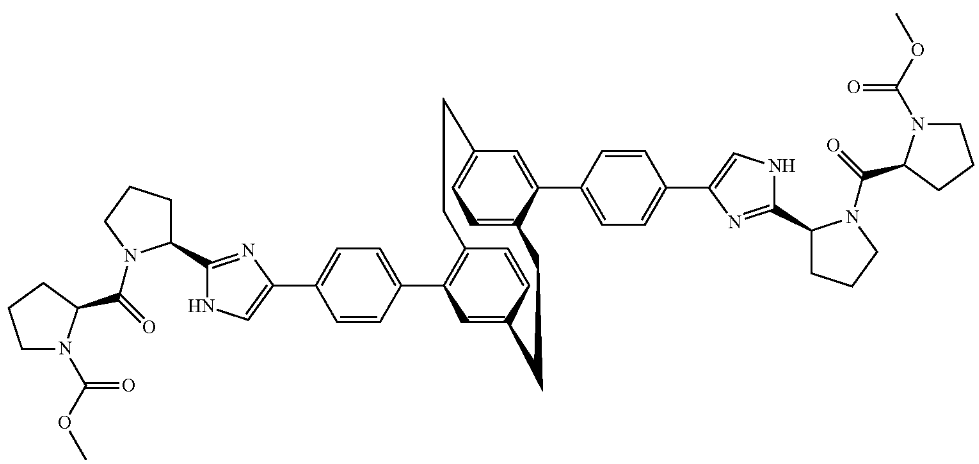 | >1 | | 1.64 | 1 | 942 |

-continued
| No. | Structure | EC50 (μM) NS5A1b | EC50 (μM) NS5A1b | LC | HPLC method | MS |
|---|---|---|---|---|---|---|
| 55 | 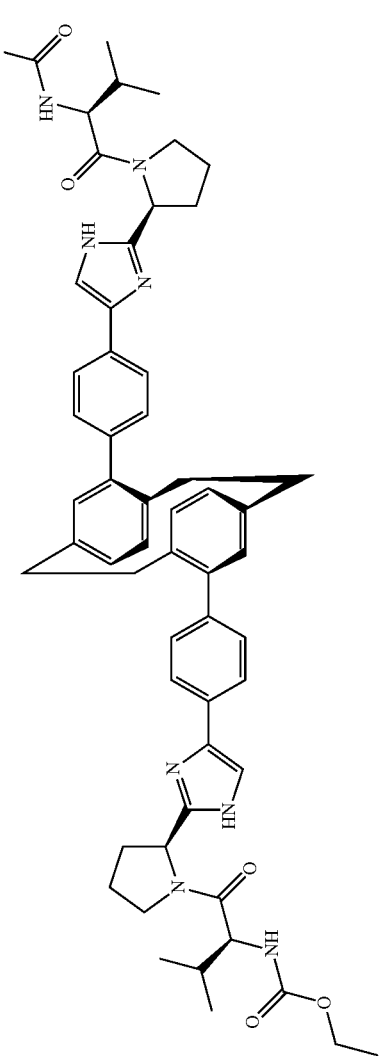 | >1 | | 2.02 | 1 | 998 |
| 56 | 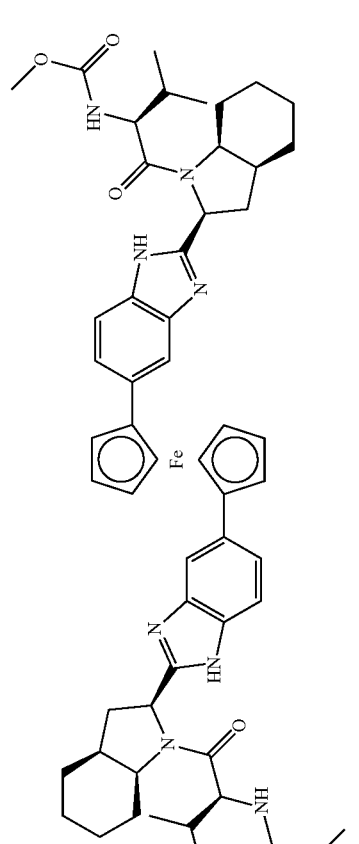 | 0.00164 | | 8.18 | 2 | 979 |

-continued

| No. | Structure | EC50 (μM) NS5A1b | EC50 (μM) NS5A1b | LC | HPLC method | MS |
|---|---|---|---|---|---|---|
| 57 | 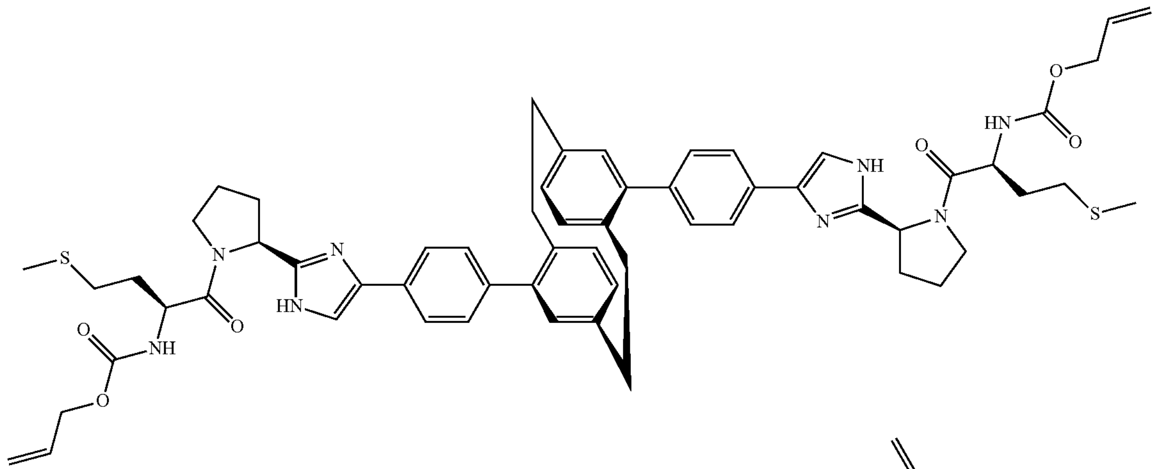 | >1 | | 2.04 | 1 | 1062 |
| 58 | 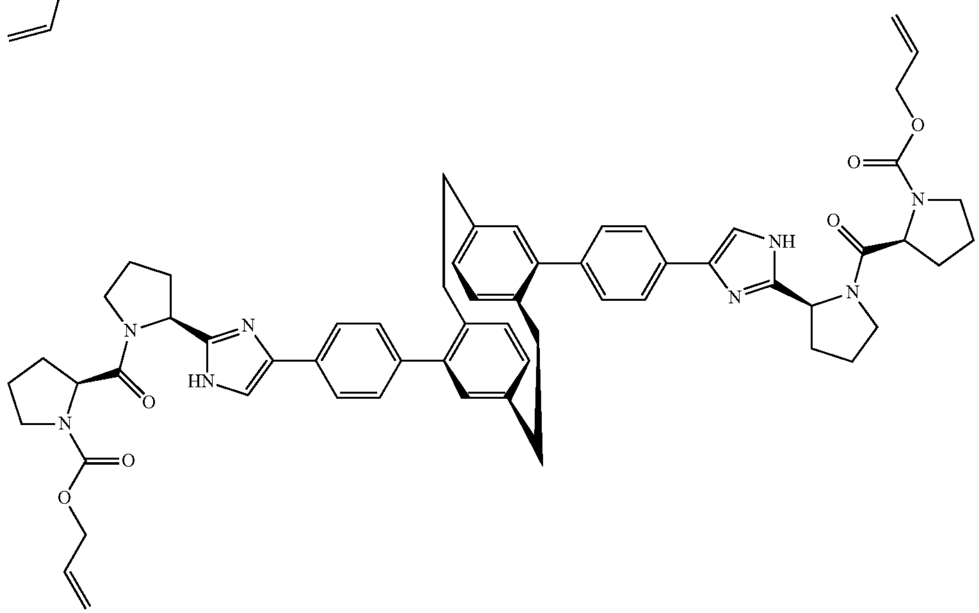 | >1 | | 1.9 | 1 | 994 |

-continued

| No. | Structure | EC50 (µM) | | HPLC | | MS |
| --- | --- | --- | --- | --- | --- | --- |
| | | NS5A1b | NS5A1b | LC | method | |
| 59 | 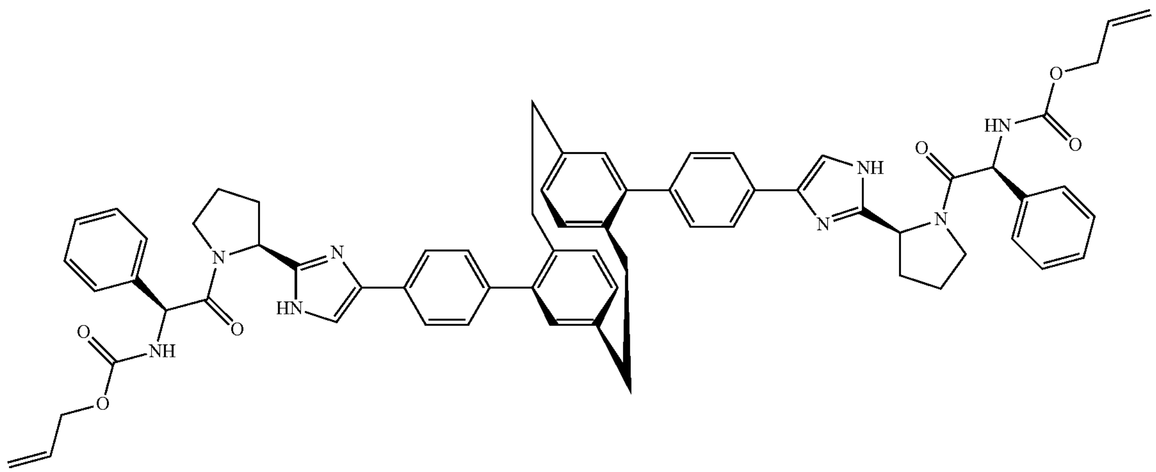 | 0.548 | | 2.21 | 1 | 1066 |
| 60 | 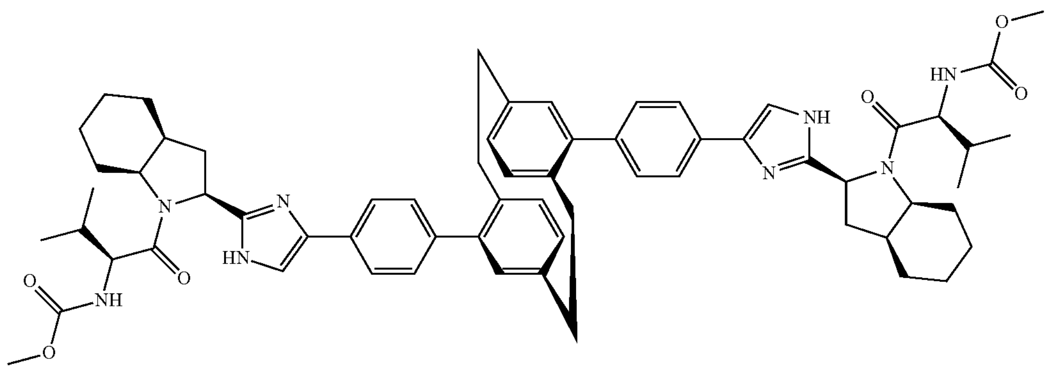 | 0.128 | | 2.45 | 1 | 1054 |

-continued

| No. | Structure | EC50 (μM) NS5A1b | EC50 (μM) NS5A1b | LC | HPLC method | MS |
|---|---|---|---|---|---|---|
| 61 | 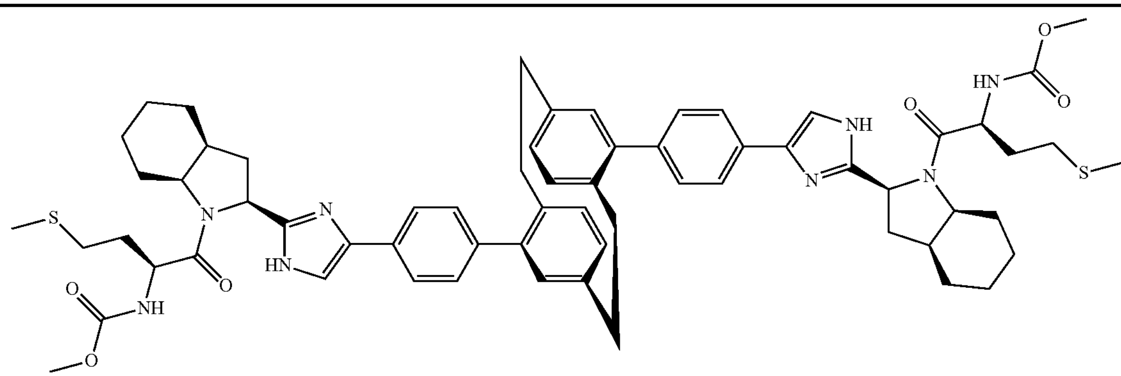 | 0.0752 | | 2.43 | 1 | 1118 |
| 62 | 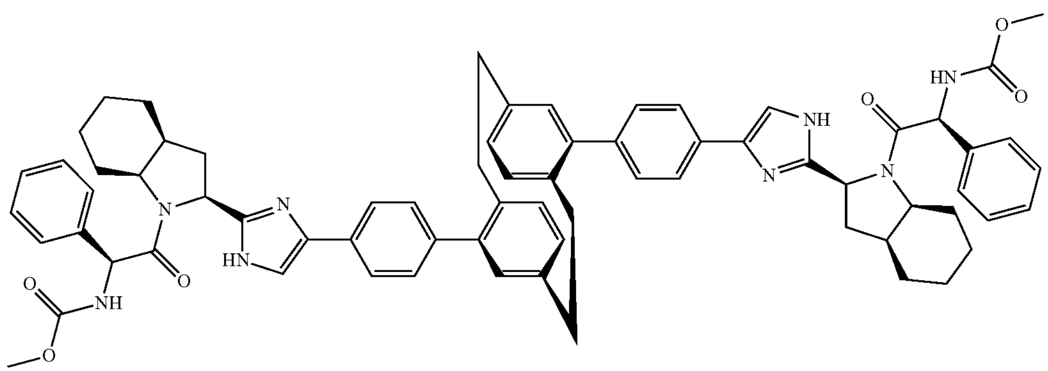 | 0.075 | | 2.58 | 1 | 1122 |

-continued

| No. | Structure | EC50 (μM) NS5A1b | EC50 (μM) NS5A1b | HPLC LC | HPLC method | MS |
|---|---|---|---|---|---|---|
| 63 | 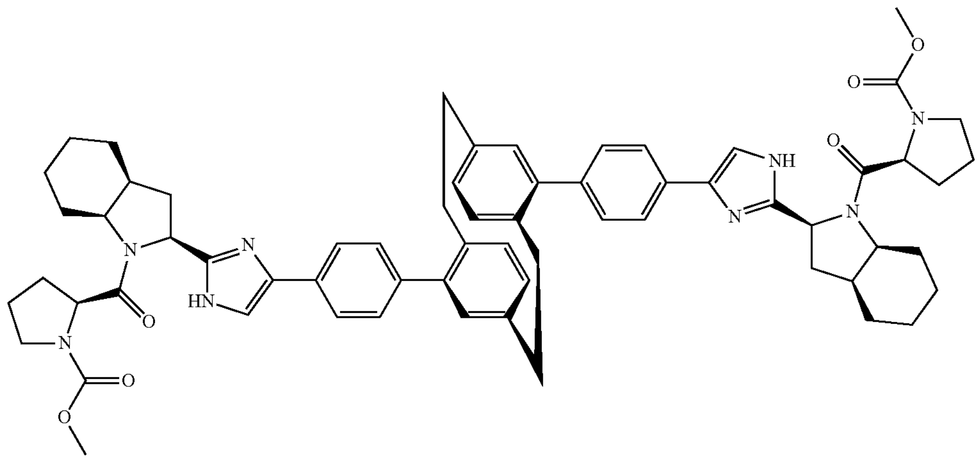 | 0.899 | | 2.33 | 1 | 1051 |
| 64 | 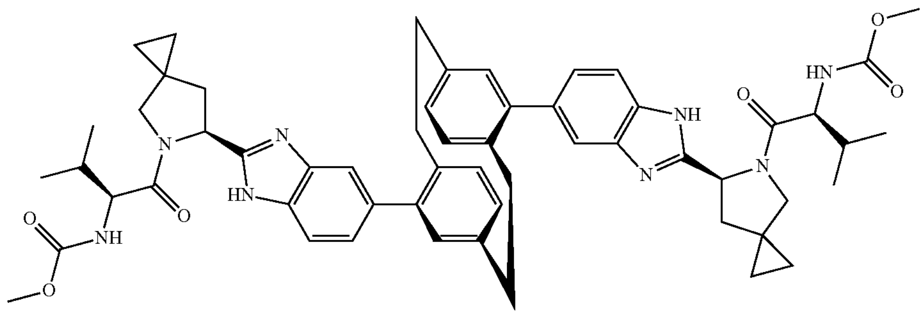 | | | | | |

-continued

| No. | Structure | EC50 (µM) NS5A1b | EC50 (µM) NS5A1b | LC | HPLC method | MS |
|---|---|---|---|---|---|---|
| 65 | 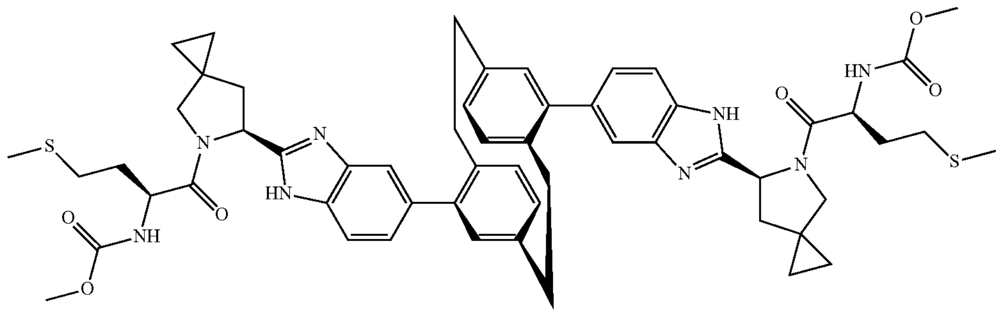 | | | | | |
| 66 | 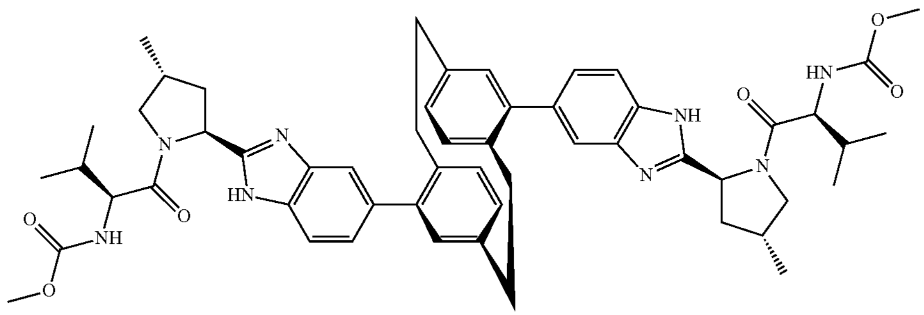 | 0.000005 | | 1.99 | 1 | 921 |
| 67 | 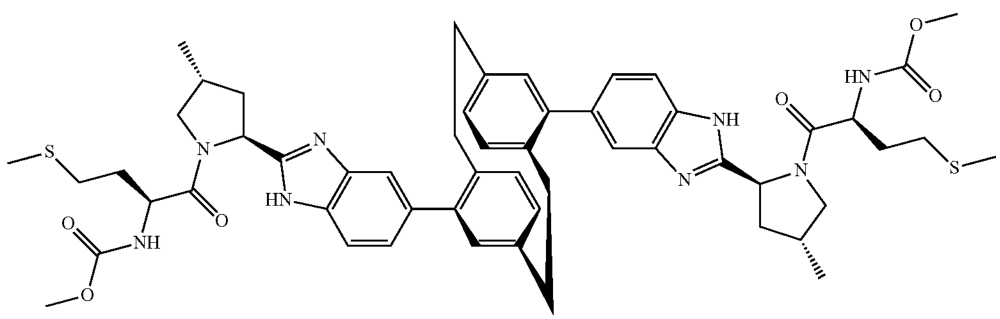 | | | | | |

-continued

| No. | Structure | EC50 (μM) NS5A1b | EC50 (μM) NS5A1b | LC | HPLC method | MS |
|---|---|---|---|---|---|---|
| 68 | 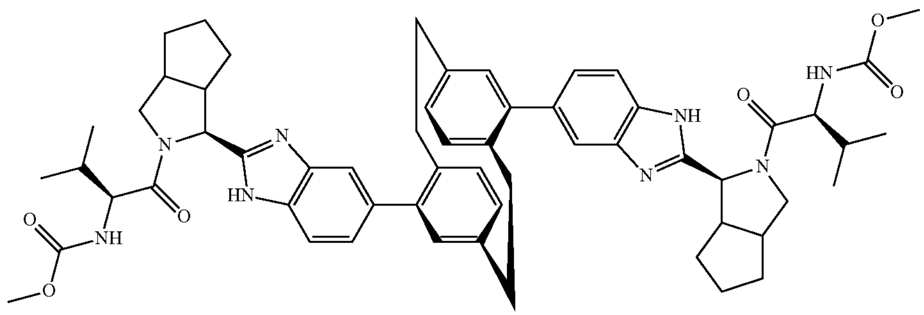 | | | | | |
| 69 | 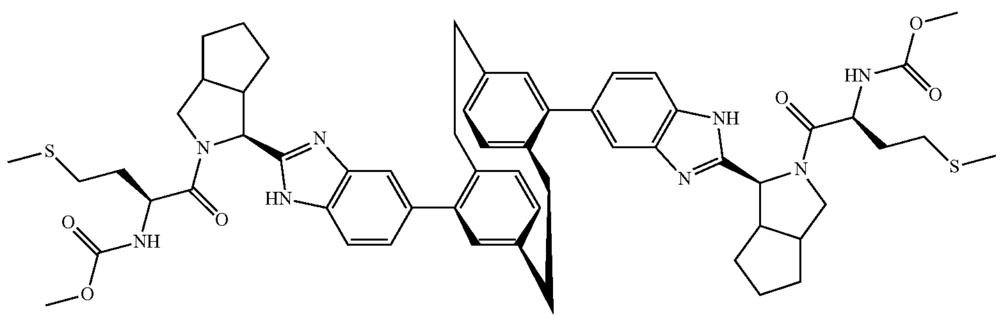 | | | | | |
| 70 | 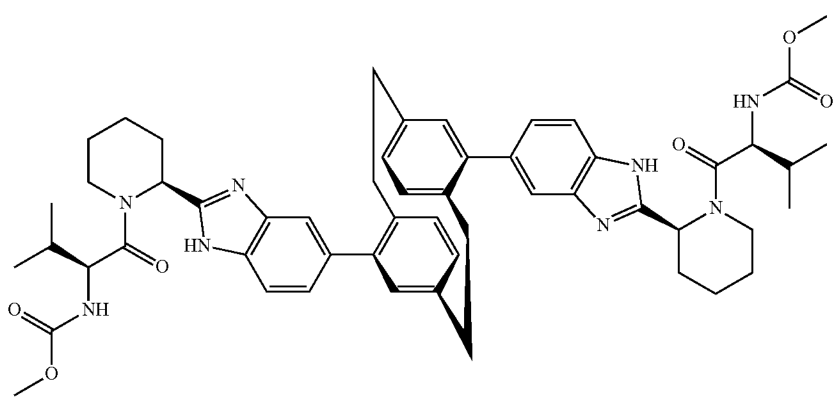 | | | 2.21 | 1 | 921 |

| No. | Structure | EC50 (μM) NS5A1b | EC50 (μM) NS5A1b | HPLC LC | HPLC method | MS |
|---|---|---|---|---|---|---|
| 71 | 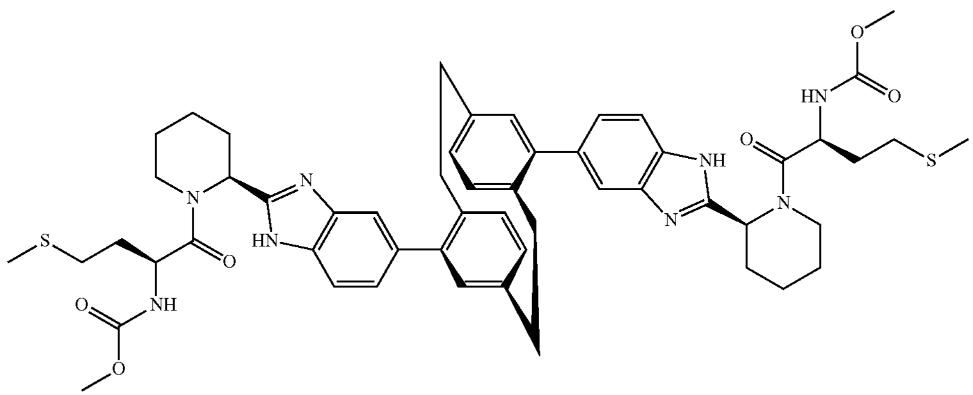 | | | | | |
| 72 | 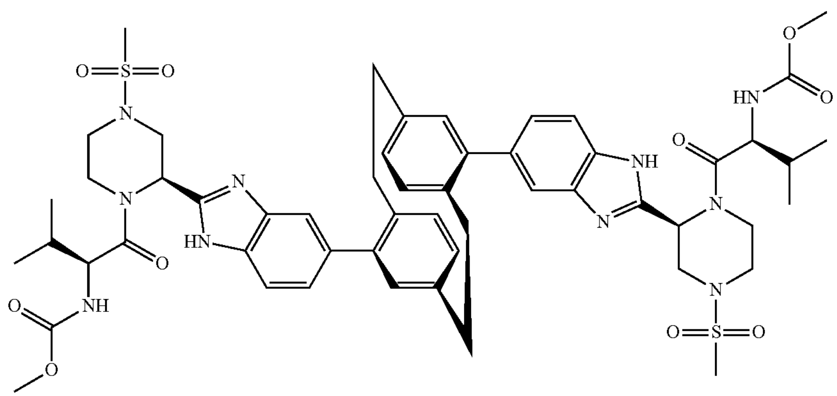 | | | 2.03 | 1 | 1079 |

| No. | Structure | EC50 (μM) NS5A1b | EC50 (μM) NS5A1b | LC | HPLC method | MS |
|---|---|---|---|---|---|---|
| 73 | 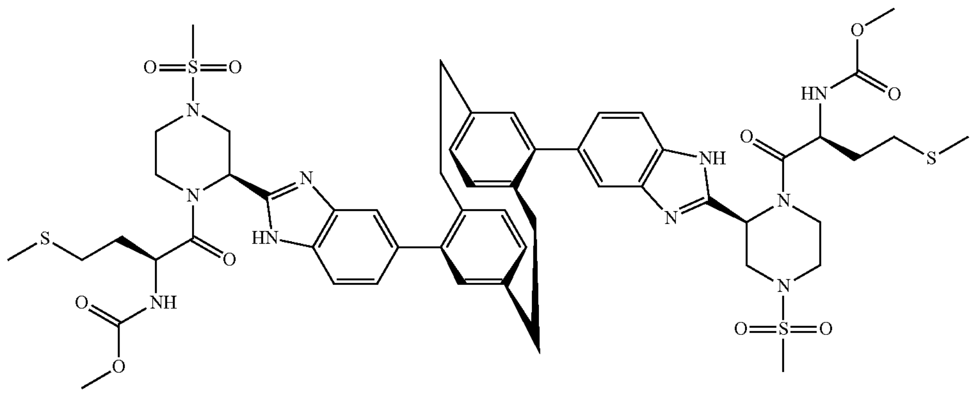 | | | 1.86 | 1 | 1143 |
| 74 | 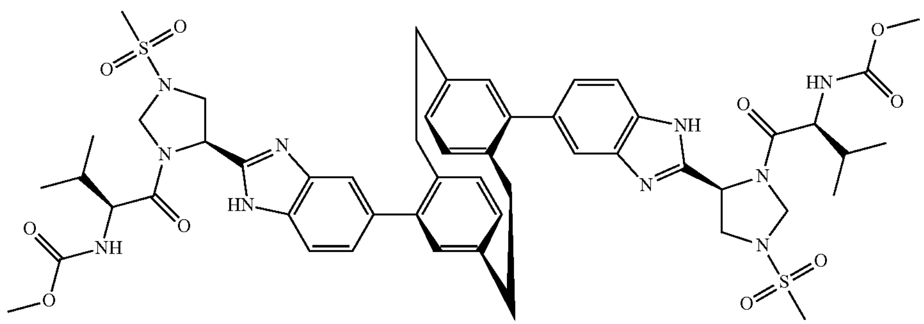 | | | | | |

-continued

| No. | Structure | EC50 (μM) NS5A1b | EC50 (μM) NS5A1b | HPLC LC | HPLC method | MS |
|---|---|---|---|---|---|---|
| 75 | 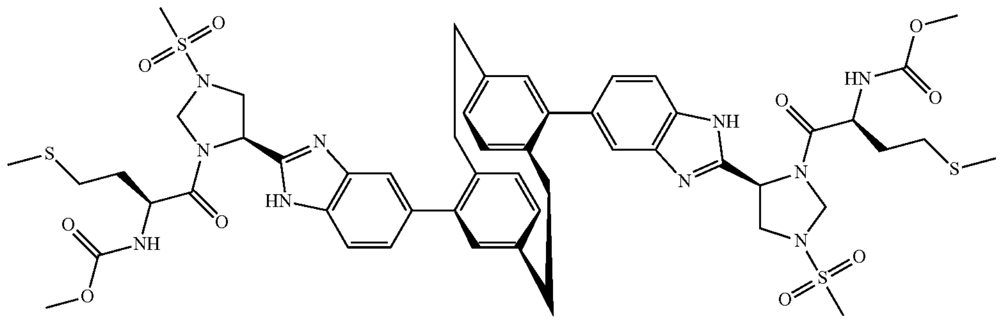 | | | | | |
| 76 | 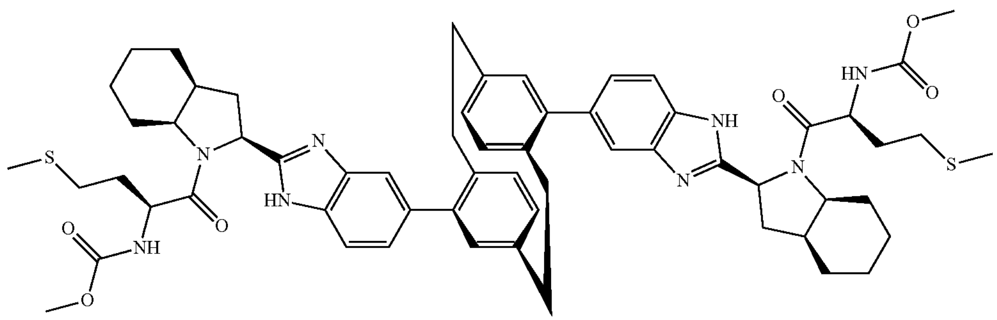 | | | | | |
| 77 | 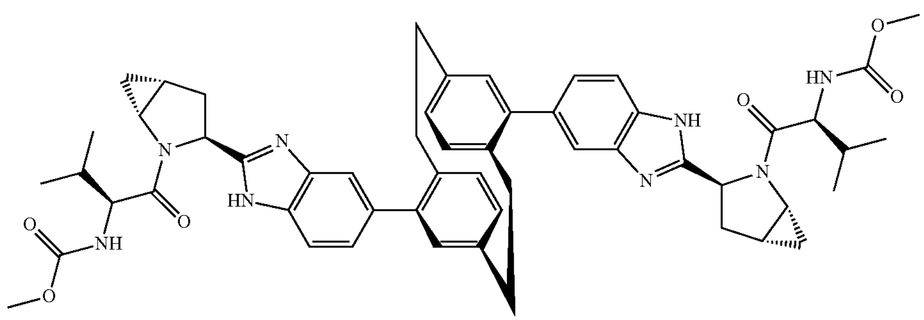 | | | 1.33 | 1 | 917 |

-continued

| No. | Structure | EC50 (μM) NS5A1b | EC50 (μM) NS5A1b | HPLC LC | HPLC method | MS |
|---|---|---|---|---|---|---|
| 78 | 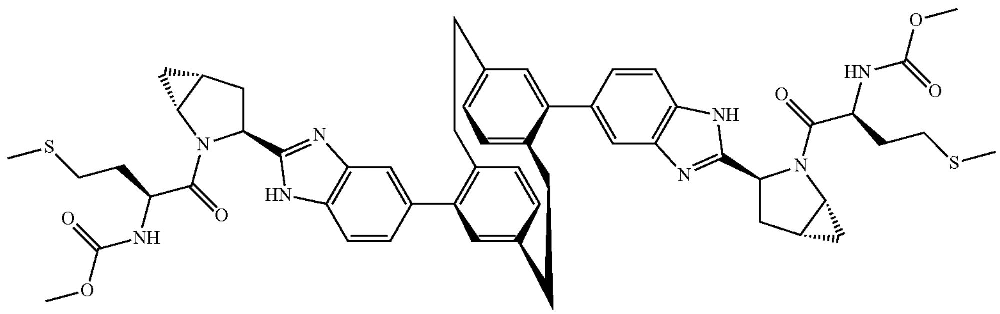 | | | 1.64 | 1 | 981 |
| 79 | 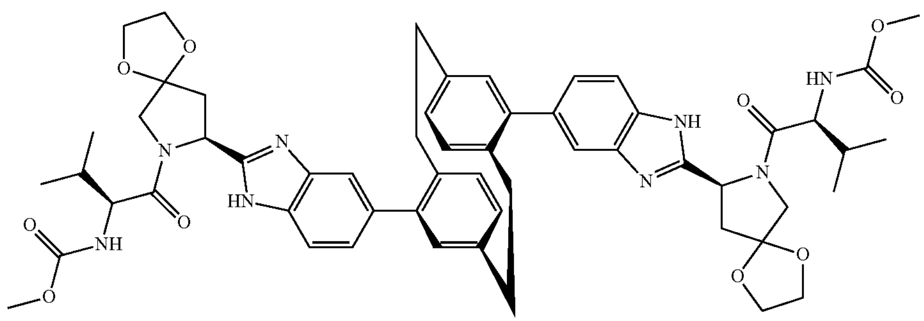 | | | | | |
| 80 | 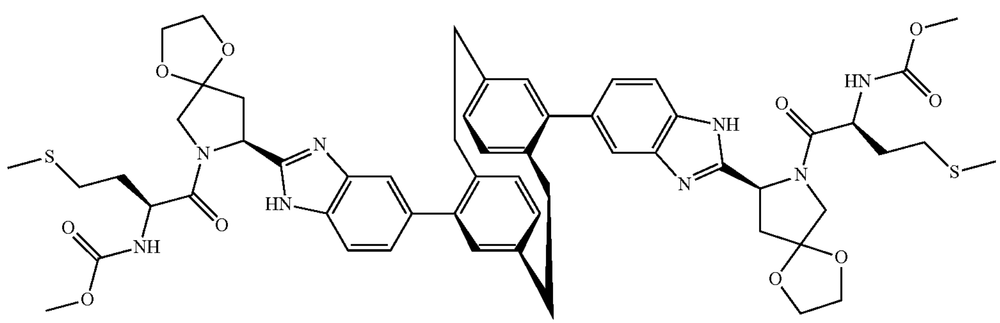 | | | | | |

| No. | Structure | EC50 (μM) NS5A1b | EC50 (μM) NS5A1b | LC | HPLC method | MS |
|---|---|---|---|---|---|---|
| 81 | 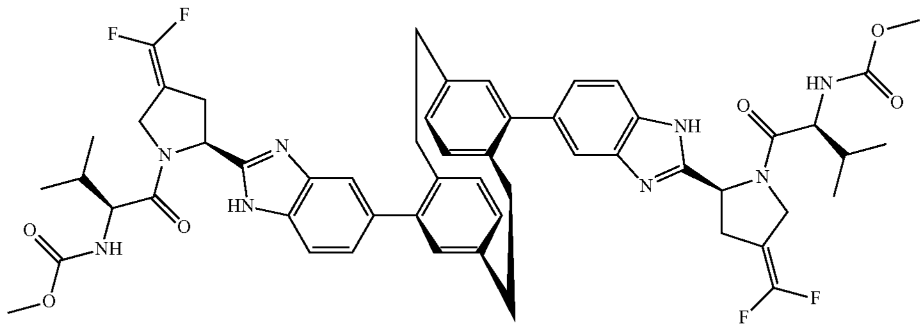 | | | | | |
| 82 | 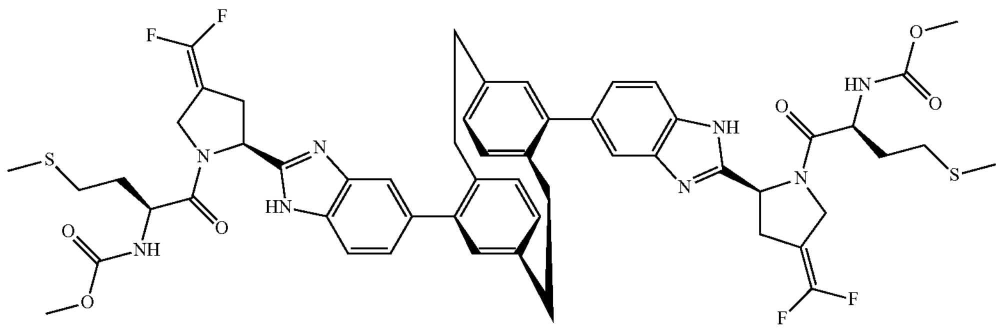 | | | | | |
| 83 | 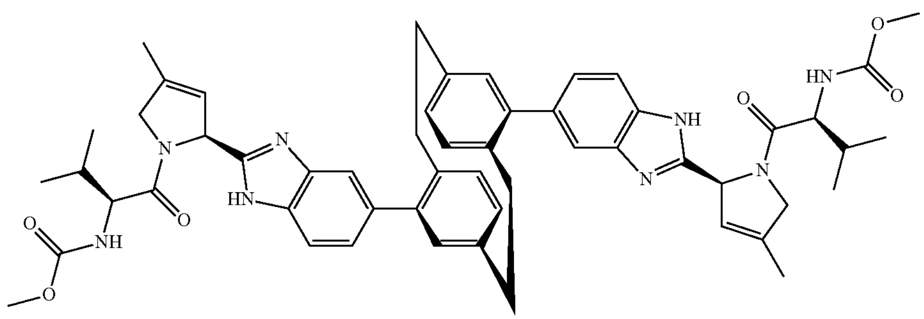 | | | | | |

| No. | Structure | EC50 (μM) | | HPLC | |
|---|---|---|---|---|---|
| | | NS5A1b | NS5A1b | LC | method MS |
| 84 | 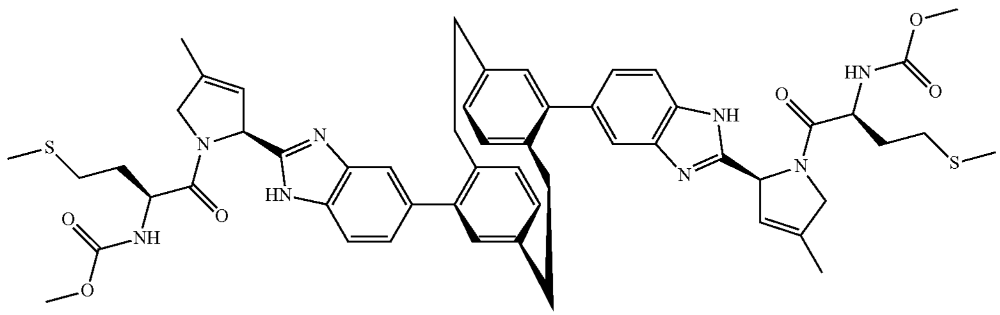 | | | | |
| 85 | 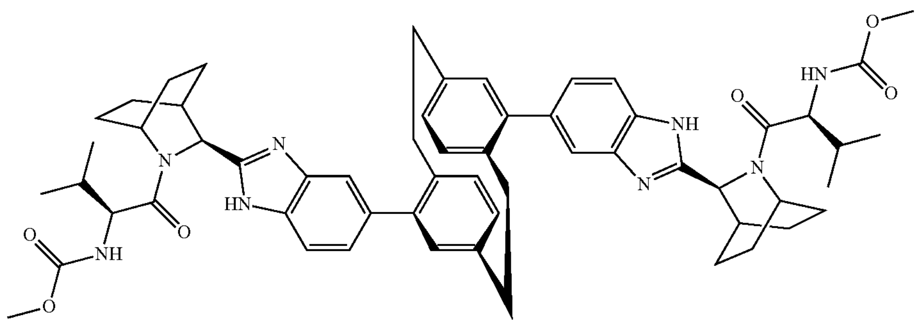 | | | | |
| 86 | 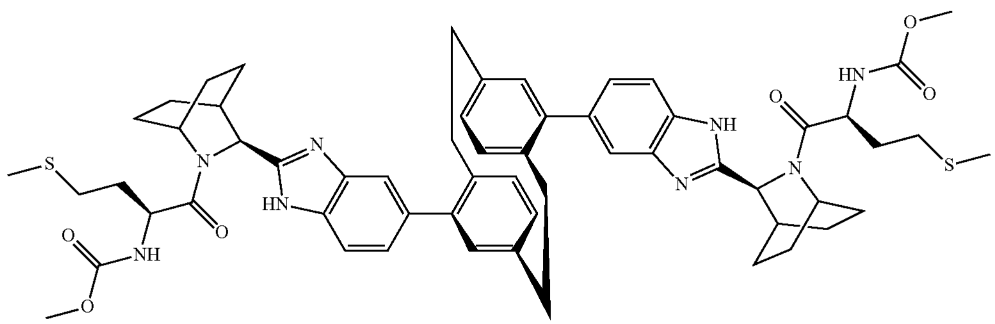 | | | | |

-continued

| No. | Structure | EC50 (μM) NS5A1b | EC50 (μM) NS5A1b | LC | HPLC method | MS |
|---|---|---|---|---|---|---|
| 87 | 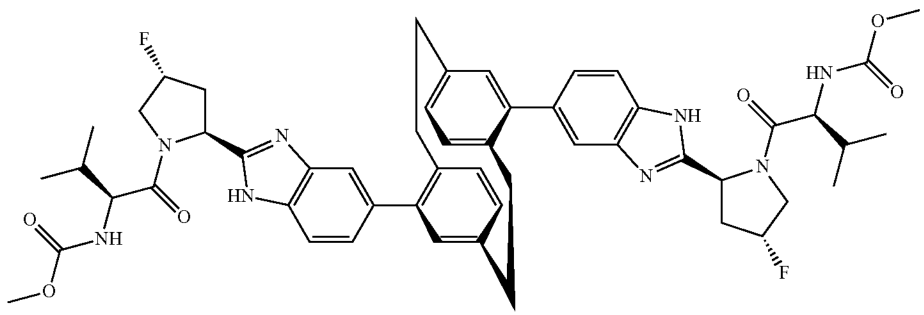 | 0.00653 | 0.0184 | 1.87 | 1 | 930 |
| 88 | 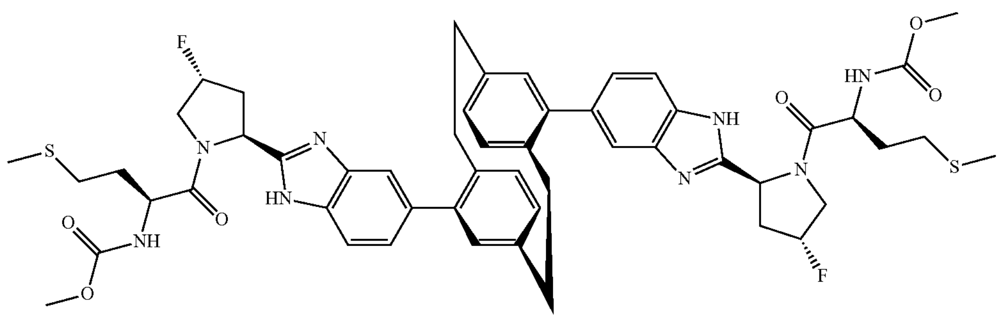 | 0.00643 | 0.0618 | 1.91 | 1 | 993 |
| 89 | 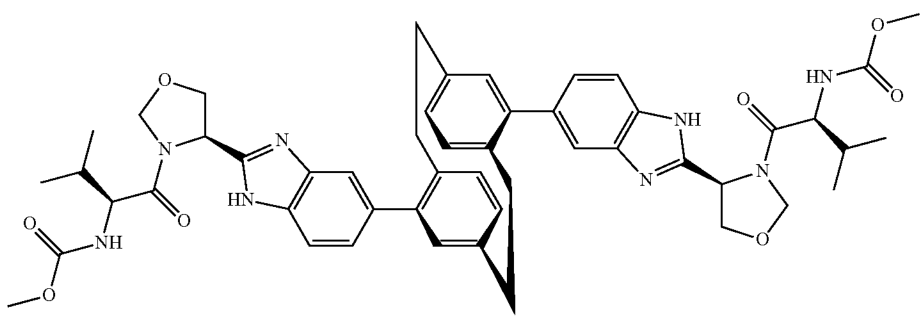 | | | | | |

| No. | Structure | EC50 (μM) NS5A1b | EC50 (μM) NS5A1b | LC | HPLC method | MS |
|---|---|---|---|---|---|---|
| 90 | 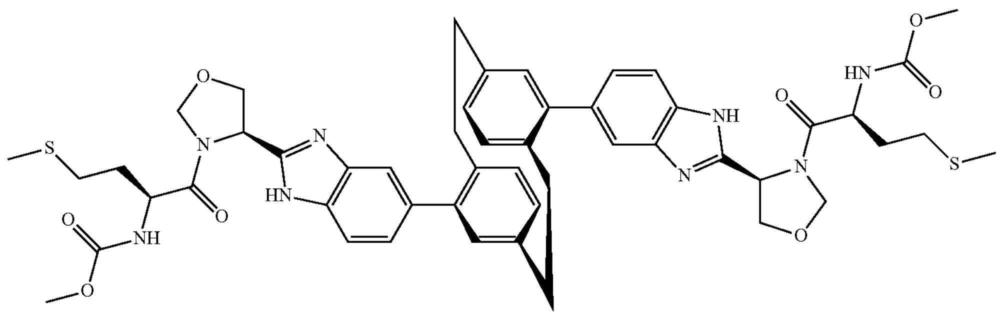 | | | | | |
| 91 | 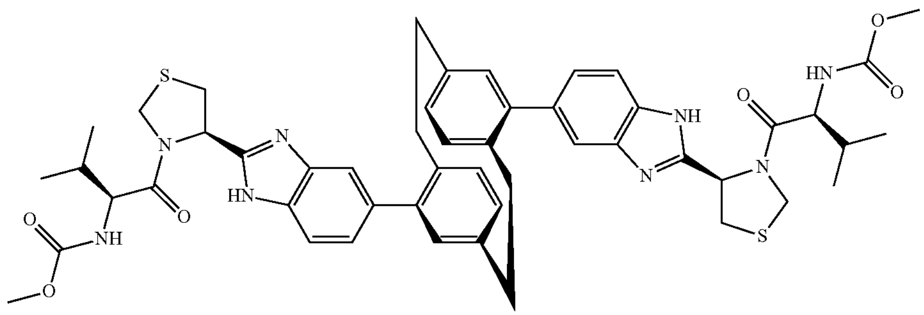 | | | 1.68 | 1 | 929 |
| 92 | 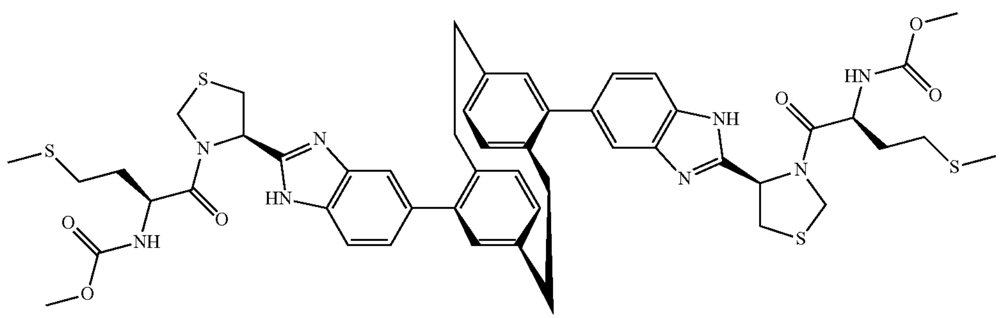 | | | | | |

-continued

| No. | Structure | EC50 (μM) | | HPLC | |
|---|---|---|---|---|---|
| | | NS5A1b | NS5A1b | LC | method | MS |
| 93 | | | | | | |
| 94 | | | | | | |

-continued

| No. | Structure | EC50 (μM) NS5A1b | EC50 (μM) NS5A1b | HPLC LC | HPLC method | MS |
|---|---|---|---|---|---|---|
| 95 | 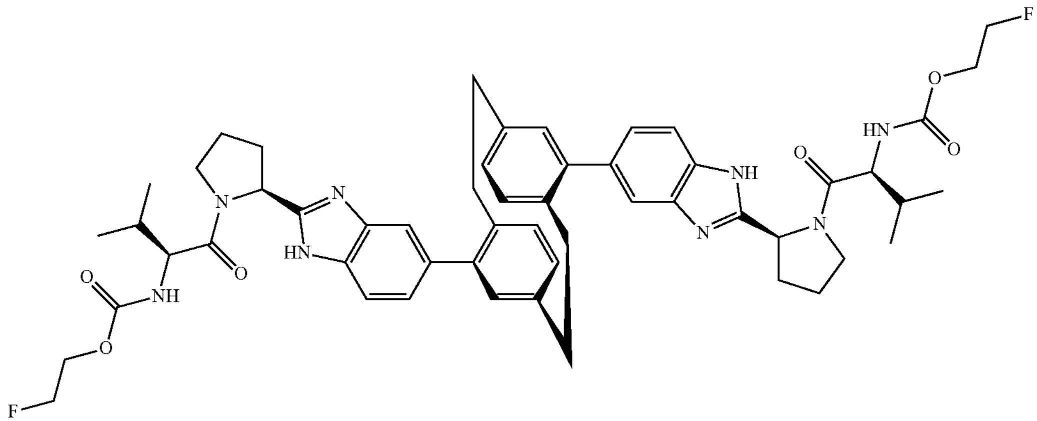 | | 1.76 | | 1 | 957 |
| 96 | 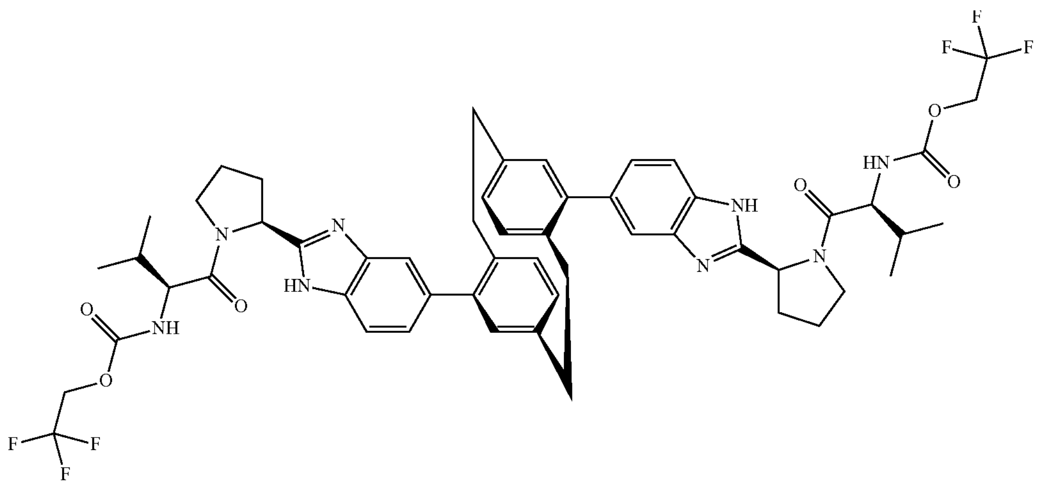 | | 2.11 | | 1 | 1029 |

-continued

| No. | Structure | EC50 (μM) NS5A1b | EC50 (μM) NS5A1b | LC | HPLC method | MS |
|---|---|---|---|---|---|---|
| 97 | 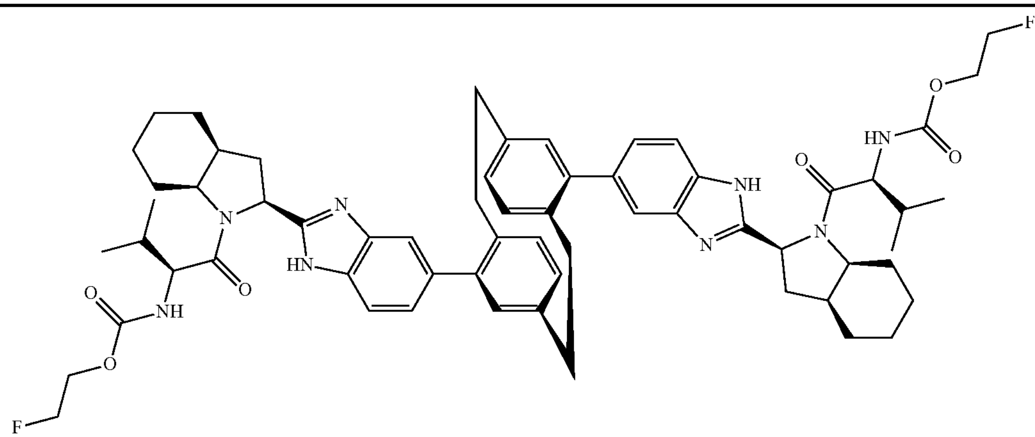 | | | 2.51 | 1 | 1060 |
| 98 | 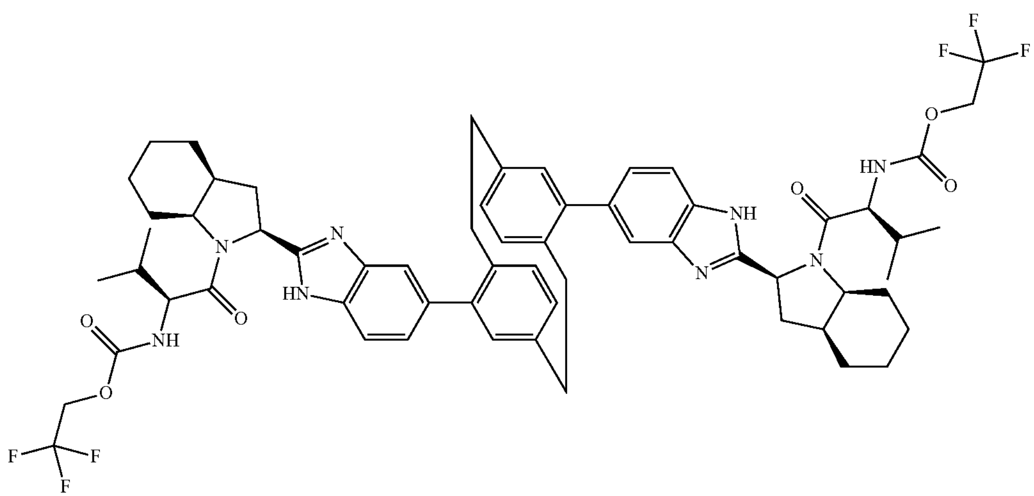 [SMILES: CC(C)[C@H](NC(=O)OCC(F)(F)F)C(=O)N1[C@H](c2nc3cc(-c4cc5ccc4CCc4ccc(c(-c6ccc7[nH]c([C@@H]8C[C@@H]9CCCC[C@@H]9N8C(=O)[C@@H](NC(=O)OCC(F)(F)F)C(C)C)nc7c6)c4)CC5)ccc3[nH]2)C[C@@H]2CCCC[C@@H]21] | | | 2.93 | 1 | 1138 |

| No. | Structure | EC50 (μM) NS5A1b | EC50 (μM) NS5A1b | HPLC LC | HPLC method | MS |
|---|---|---|---|---|---|---|
| 99 | 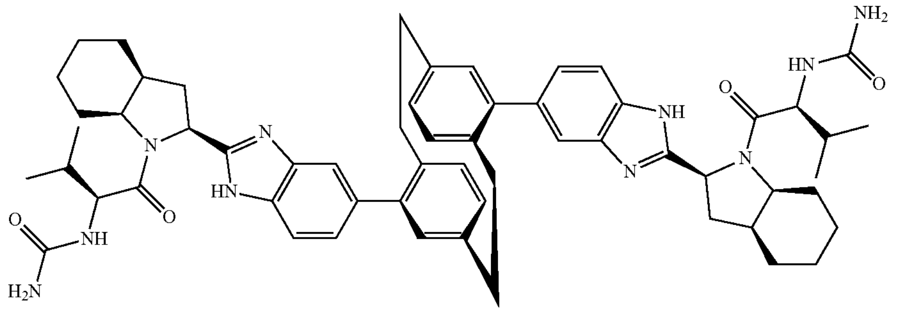 | | | | | |
| 100 | 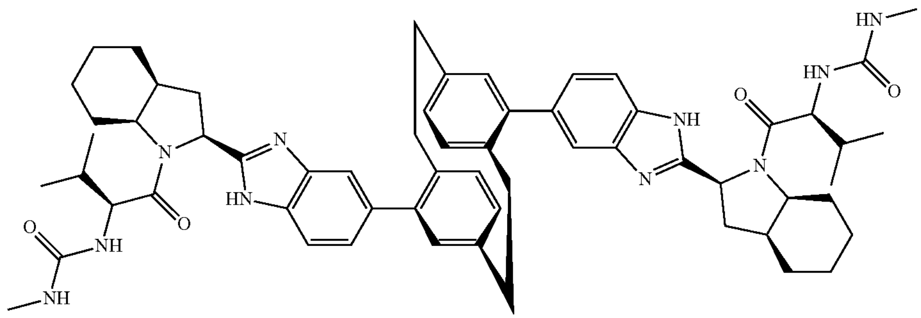 | | | | | |
| 101 | 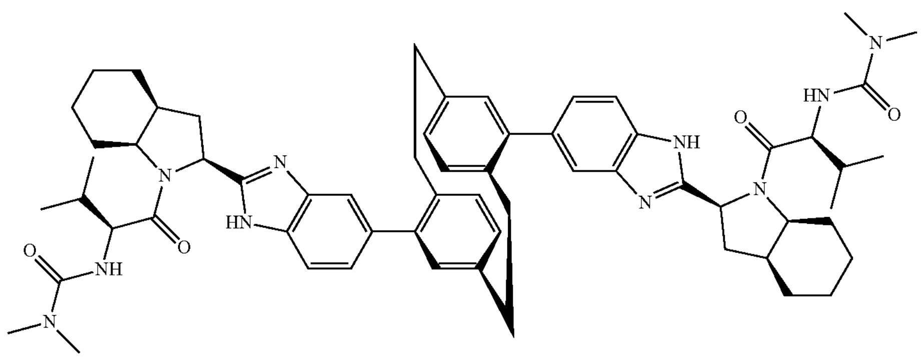 | | | 2.17 | 1 | 1028 |

-continued

| No. | Structure | EC50 (μM) NS5A1b | EC50 (μM) NS5A1b | LC | HPLC method | MS |
|---|---|---|---|---|---|---|
| 102 | 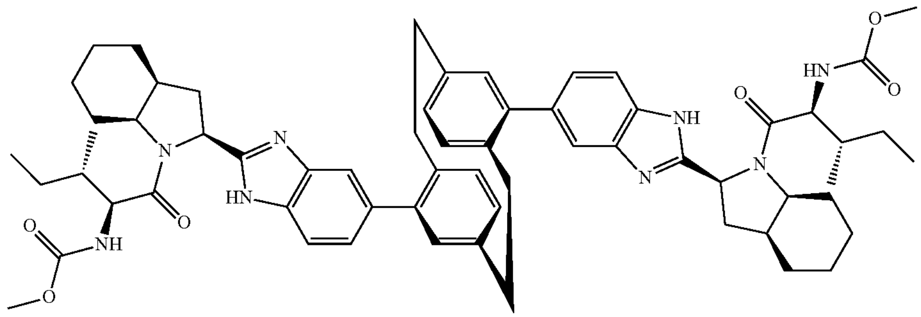 | 0.0119 | 0.0358 | 2.79 | 1 | 1030 |
| 103 | 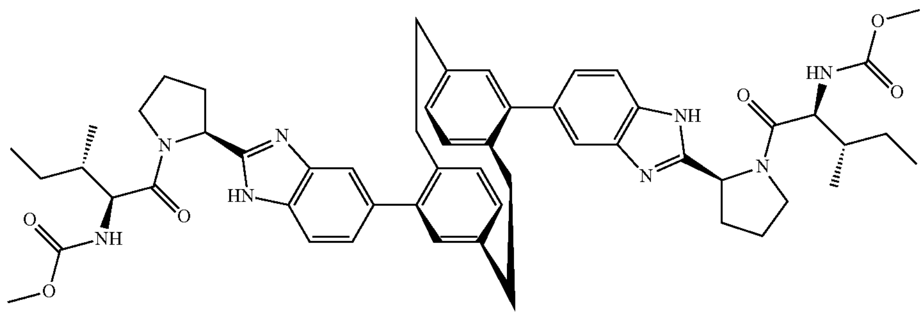 | <0.00317 | 0.47 | 1.99 | 1 | 922 |
| 104 | 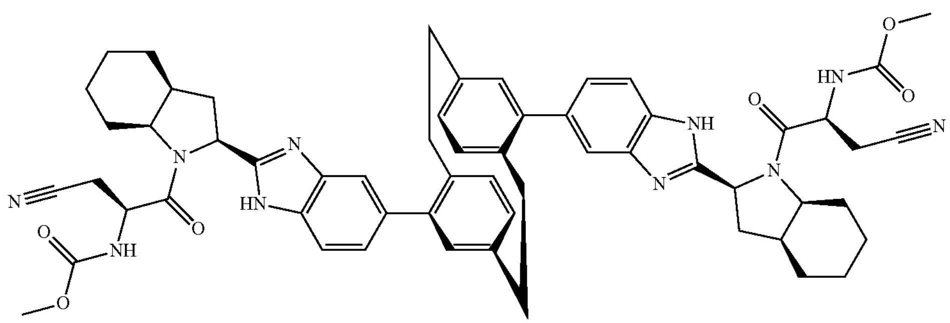 | | | 2.24 | 1 | 996 |

-continued

| No. | Structure | EC50 (µM) NS5A1b | EC50 (µM) NS5A1b | LC | HPLC method | MS |
|---|---|---|---|---|---|---|
| 105 | 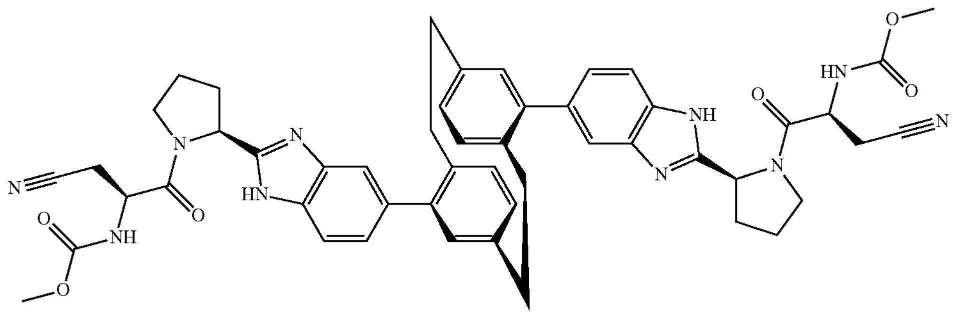 | | | 1.51 | 1 | 888 |
| 106 | 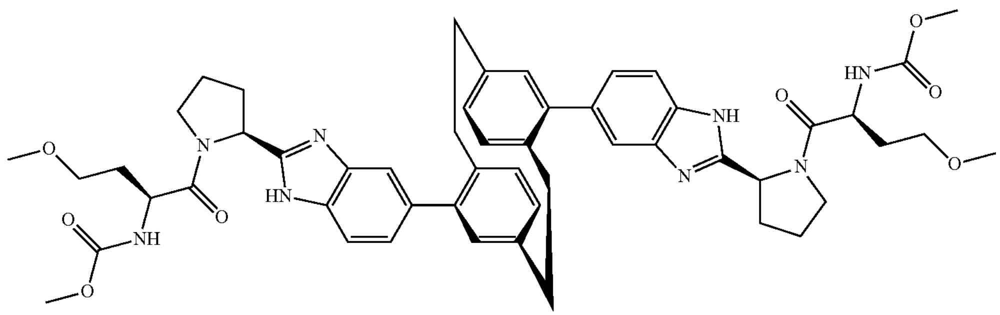 | | | | | |
| 107 | 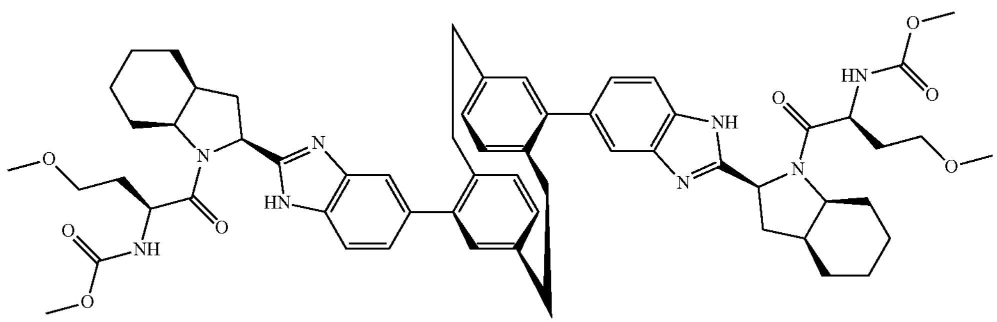 | | | | | |

-continued

| No. | Structure | EC50 (μM) NS5A1b | EC50 (μM) NS5A1b | LC | HPLC method | MS |
|---|---|---|---|---|---|---|
| 108 | 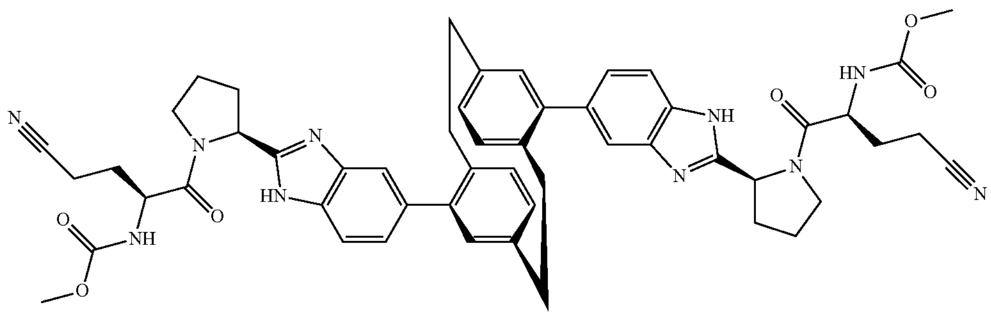 | | | 1.63 | 1 | 915 |
| 109 | 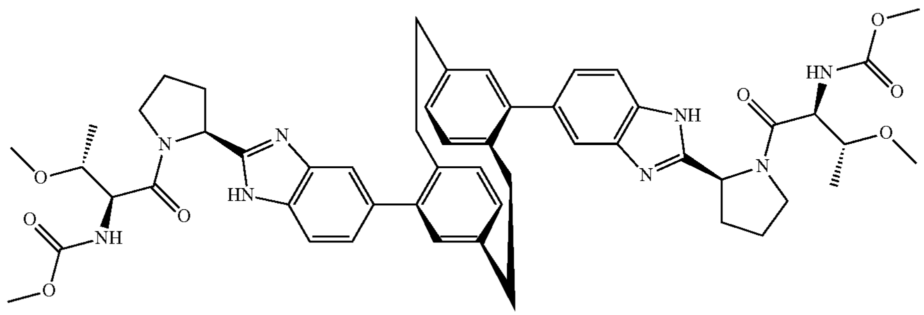 | 0.00883 | 0.0118 | 1.63 | 1 | 926 |
| 110 | 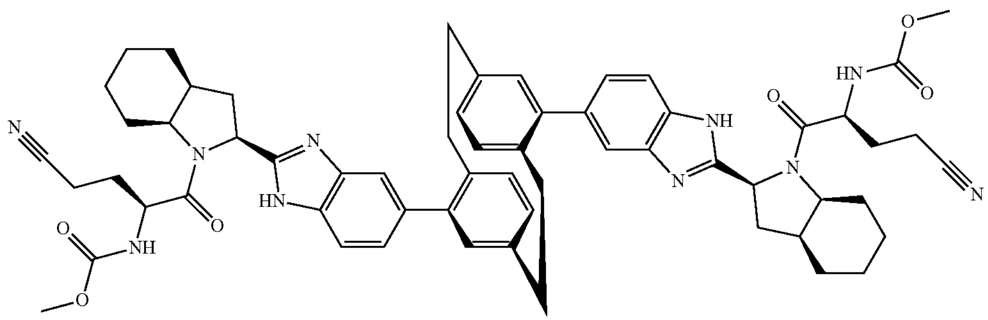 | 0.000006 | | 2.11 | 1 | 1024 |

-continued

| No. | Structure | EC50 (μM) NS5A1b | EC50 (μM) NS5A1b | LC | HPLC method | MS |
|---|---|---|---|---|---|---|
| 111 | 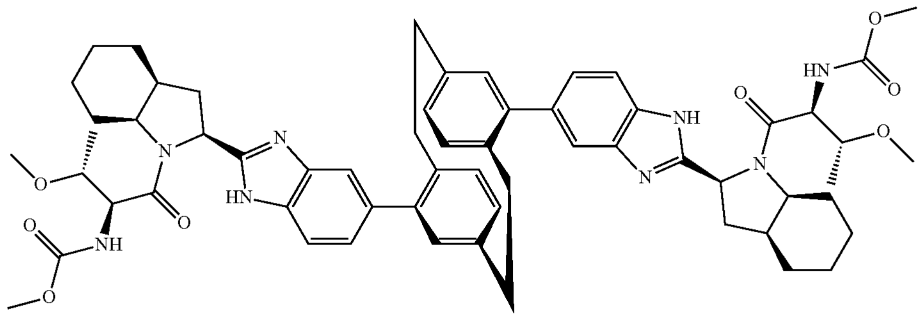 | 0.000005 | | 2.37 | 1 | 1034 |
| 112 | 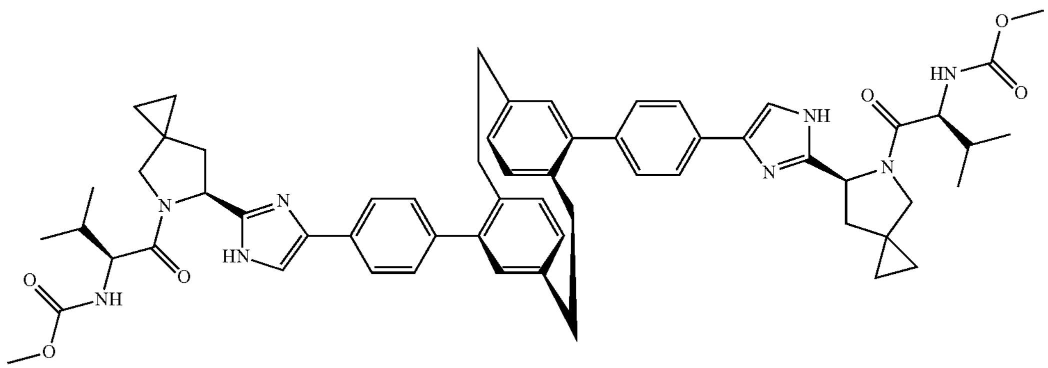 | | | | | |

| No. | Structure | EC50 (μM) NS5A1b | NS5A1b | LC | HPLC method | MS |
|---|---|---|---|---|---|---|
| 113 | 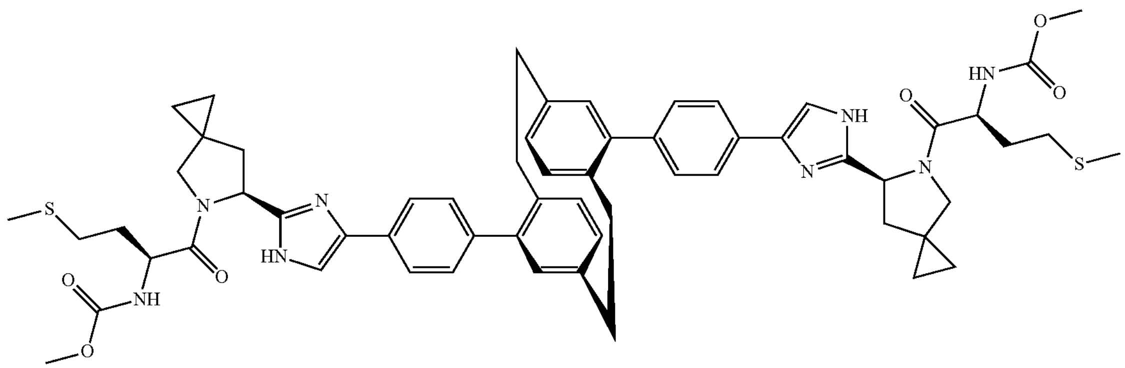 | | | | | |
| 114 | 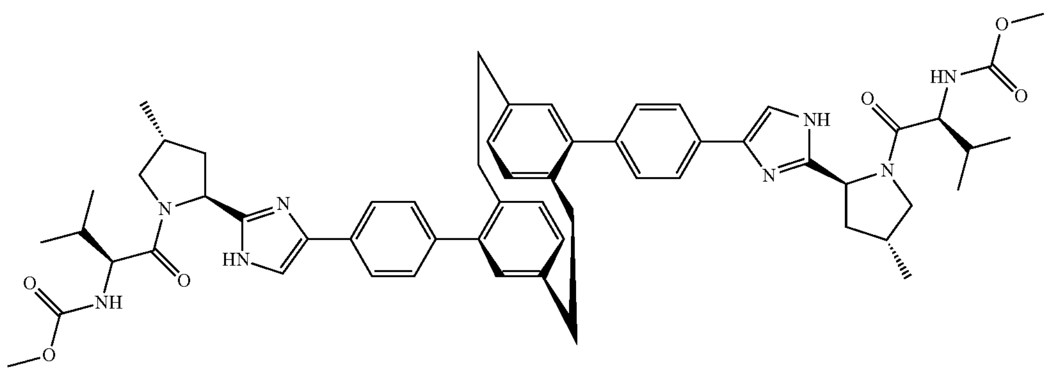 | | | | | |

| No. | Structure | EC50 (μM) NS5A1b | EC50 (μM) NS5A1b | LC | HPLC method | MS |
|---|---|---|---|---|---|---|
| 115 | 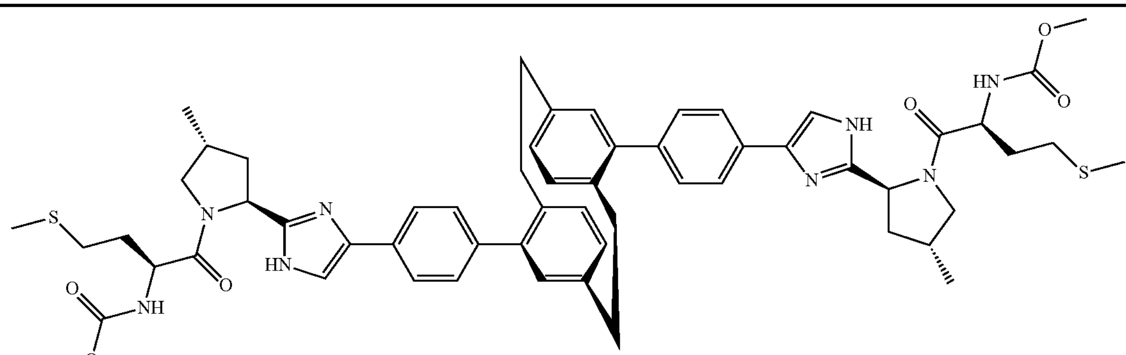 | | | | | |
| 116 | 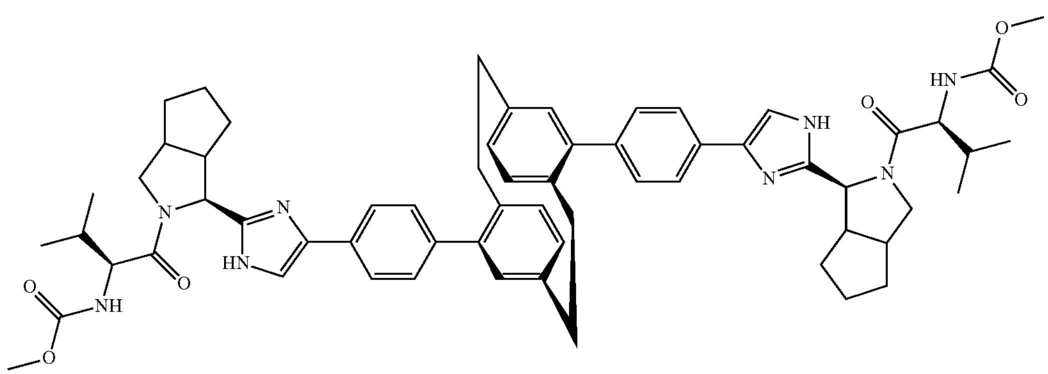 | | | | | |

| No. | Structure | EC50 (μM) NS5A1b | EC50 (μM) NS5A1b | LC | HPLC method | MS |
|---|---|---|---|---|---|---|
| 117 | 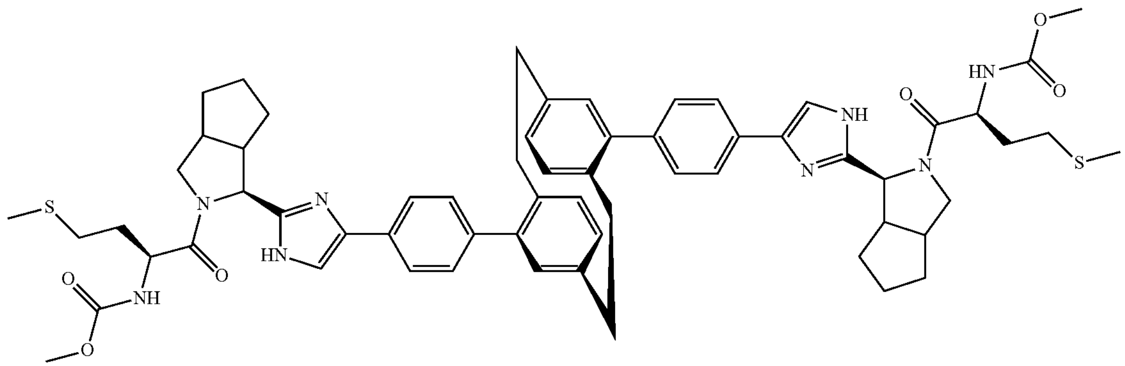 | | | | | |
| 118 | 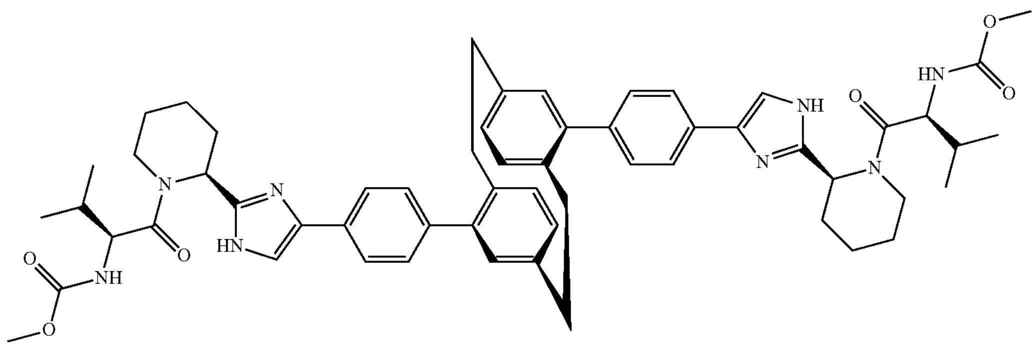 | | | | | |

-continued

| No. | Structure | EC50 (μM) | | HPLC | |
|---|---|---|---|---|---|
| | | NS5A1b | NS5A1b | LC | method MS |
| 119 | 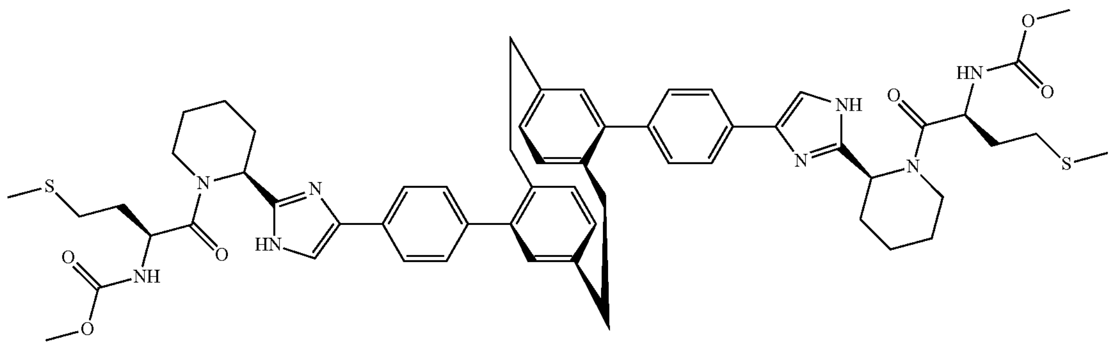 | | | | |
| 120 | 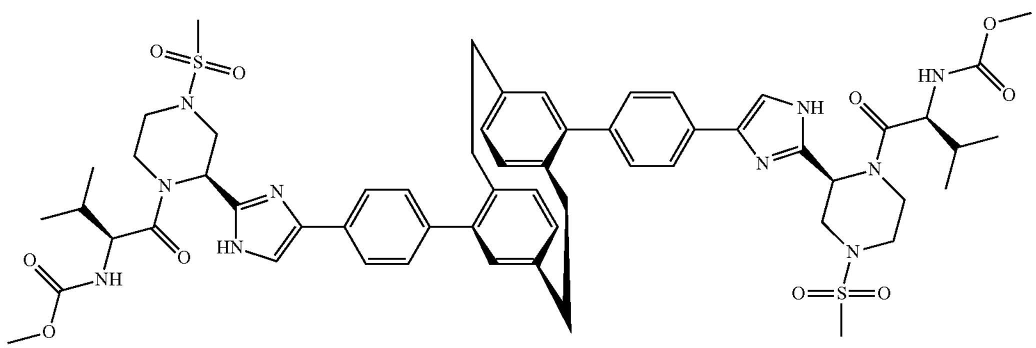 | | | | |

| No. | Structure | EC50 (μM) | | LC | HPLC method | MS |
|---|---|---|---|---|---|---|
| | | NS5A1b | NS5A1b | | | |
| 121 | 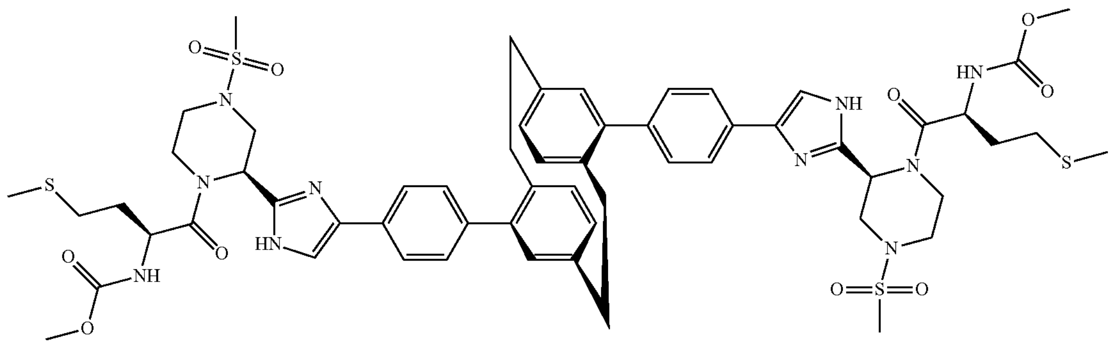 | | | | | |
| 122 | 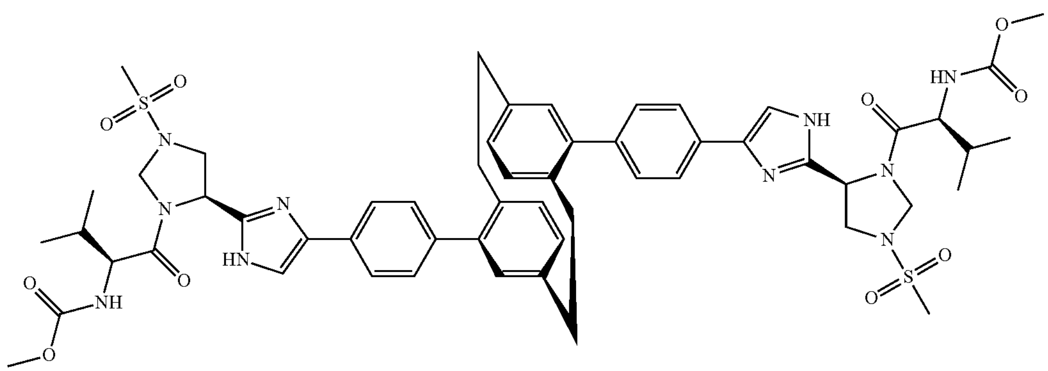 | | | | | |

| No. | Structure | EC50 (μM) NS5A1b | EC50 (μM) NS5A1b | LC | HPLC method | MS |
|---|---|---|---|---|---|---|
| 123 | 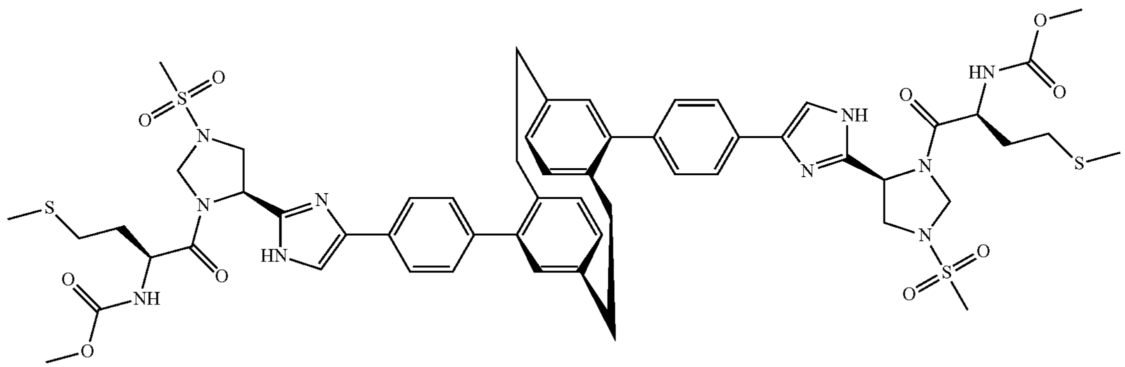 | | | 1.8 | 1 | 910 |
| 124 | 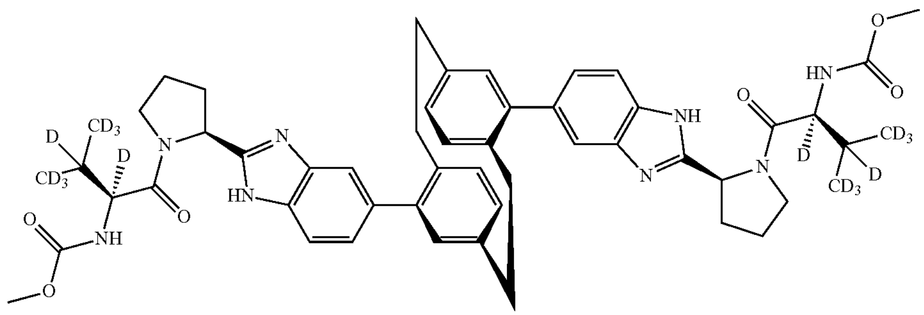 | | | 2.73 | 1 | 1018 |
| 125 | 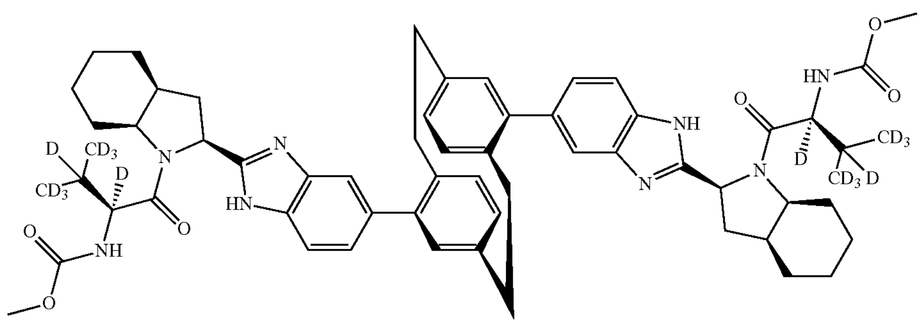 | | | | | |

| No. | Structure | EC50 (μM) NS5A1b | EC50 (μM) NS5A1b | HPLC LC | HPLC method | MS |
|---|---|---|---|---|---|---|
| 126 | 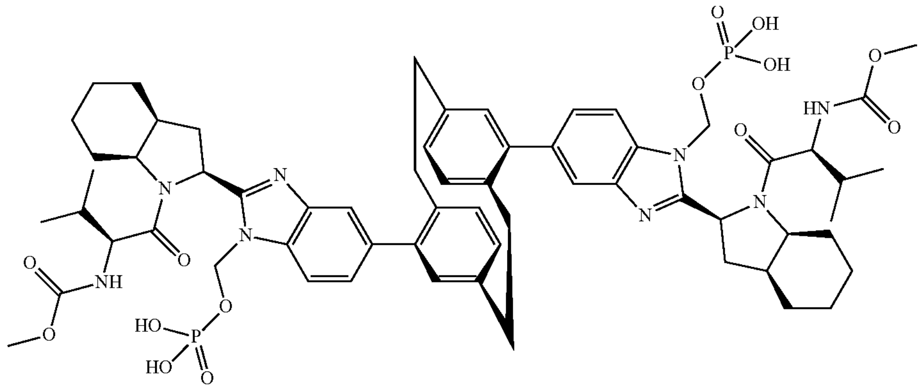 | | | 2.08 | 1 | 1222 |
| 127 | 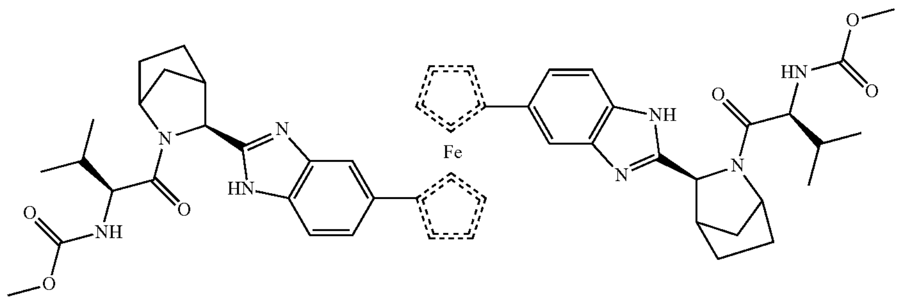 | 0.633 | >1 | 8.2 | 2 | 923 |
| 128 | 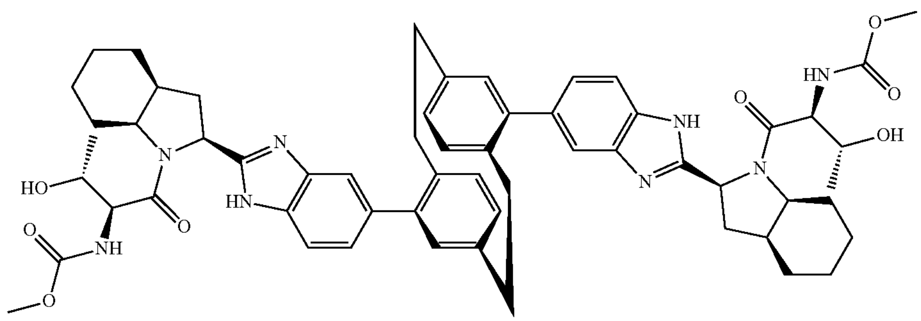 | 0.000008 | | 2.15 | 1 | 1006 |

-continued

| No. | Structure | EC50 (µM) NS5A1b | EC50 (µM) NS5A1b | LC | HPLC method | MS |
|-----|-----------|------------------|------------------|-----|-------------|-----|
| 129 | 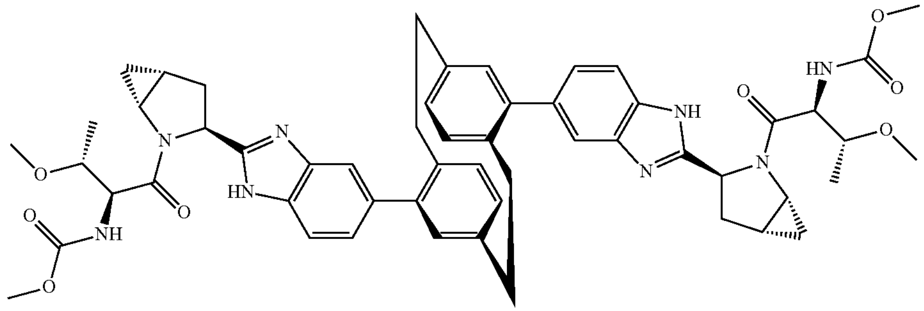 | | | | | |
| 130 | 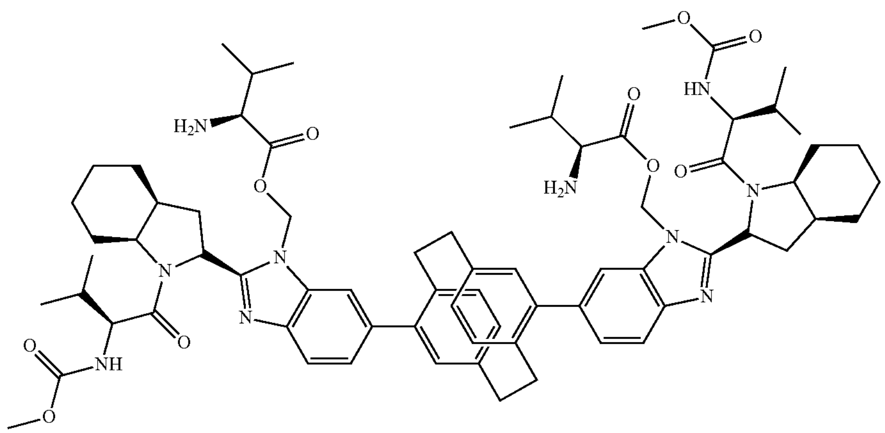 | 0.000009 | | 2.2 | 1 | 1261 |

| No. | Structure | EC50 (μM) | | HPLC | |
| --- | --- | --- | --- | --- | --- |
| | | NS5A1b | NS5A1b | LC method | MS |
| 131 | 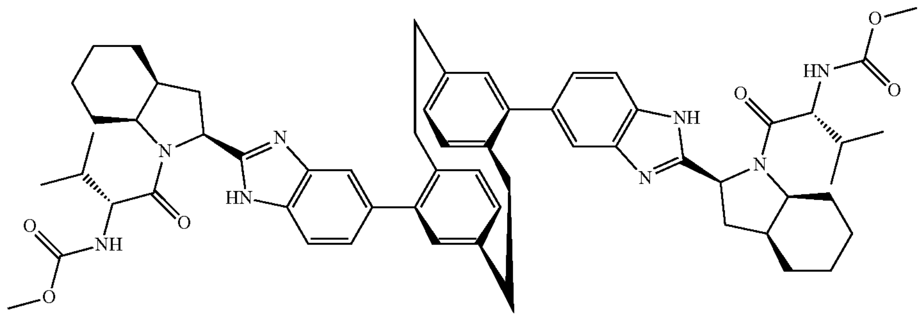 | | | | |
| 132 | 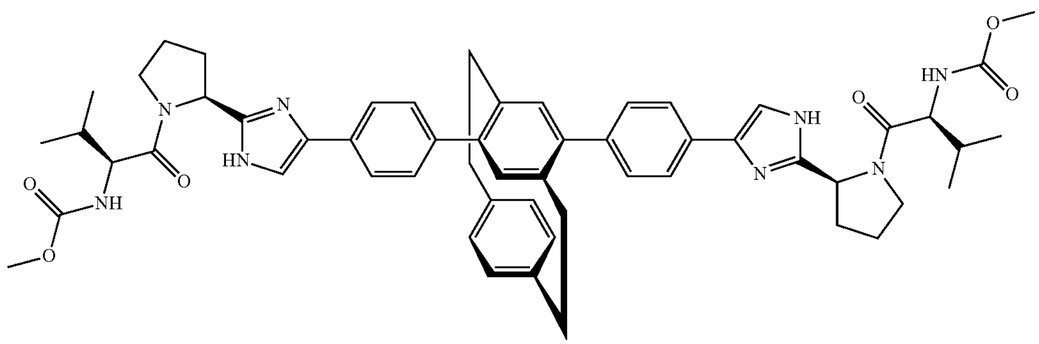 | | | | |

| No. | Structure | EC50 (μM) NS5A1b | NS5A1b | LC | HPLC method | MS |
|---|---|---|---|---|---|---|
| 133 | 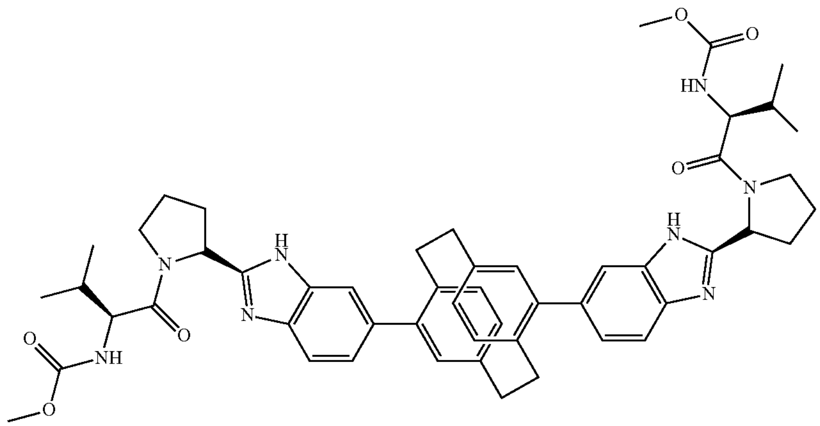 | | | | | |
| 134 | 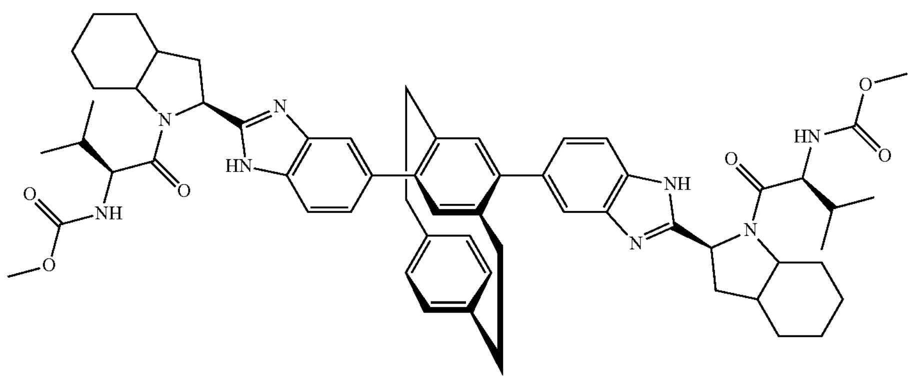 | | | | | |

|  | | EC50 (μM) | | HPLC | |
|---|---|---|---|---|---|
| No. | Structure | NS5A1b | NS5A1b | LC method | MS |
| 135 | | | | | |
| 136 | | | | | |

| No. | Structure | EC50 (μM) NS5A1b | EC50 (μM) NS5A1b | LC | HPLC method | MS |
|---|---|---|---|---|---|---|
| 137 | 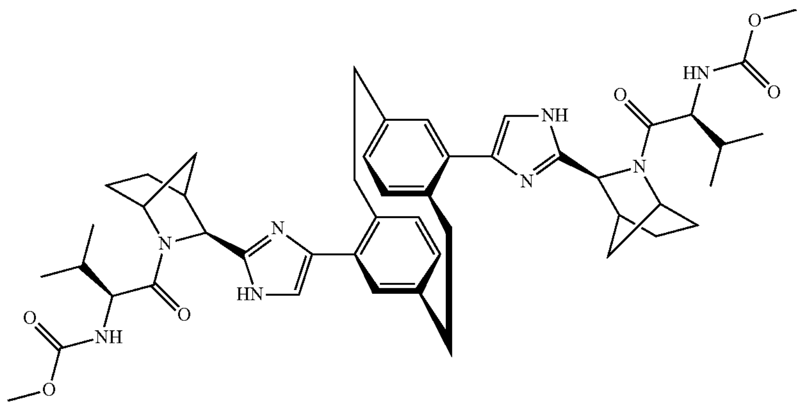 | | | | | |
| 138 | 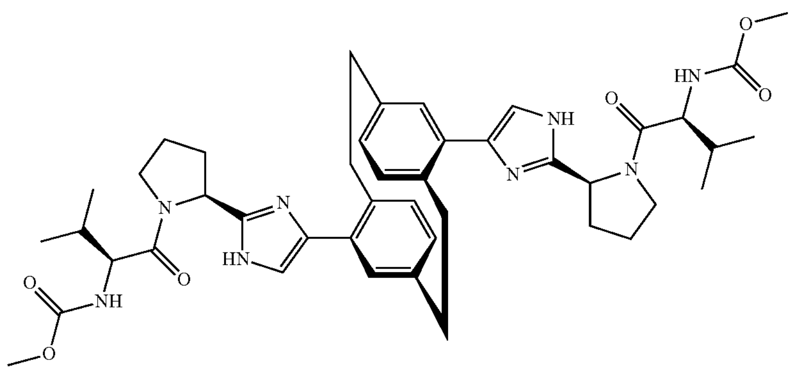 | | | | | |

| No. | Structure | EC50 (μM) NS5A1b | NS5A1b | LC | HPLC method | MS |
|---|---|---|---|---|---|---|
| 139 | 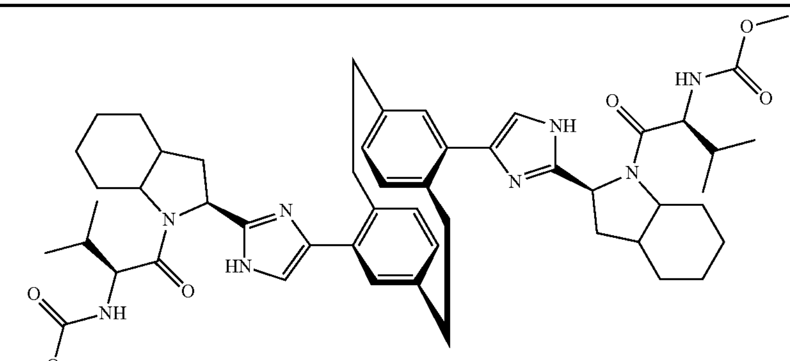 | | | | | |
| 140 | 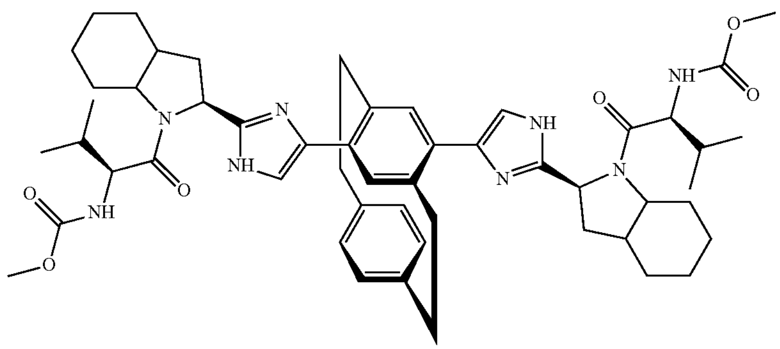 | | | | | |

-continued

| No. | Structure | EC50 (μM) NS5A1b | EC50 (μM) NS5A1b | HPLC LC | HPLC method | MS |
|---|---|---|---|---|---|---|
| 141 | 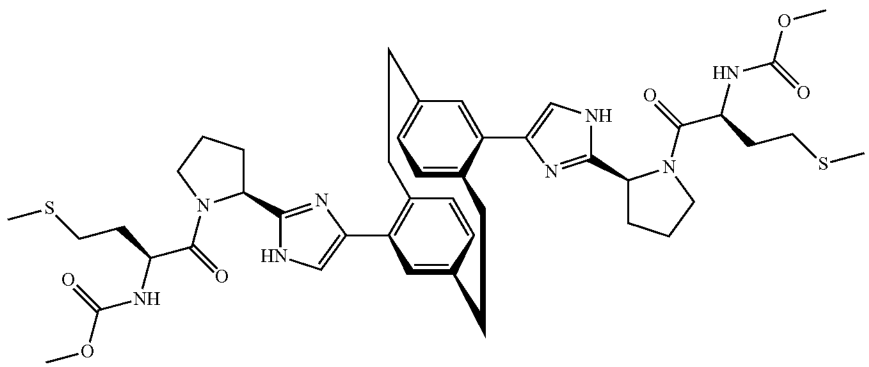 | | | | | |
| 142 | 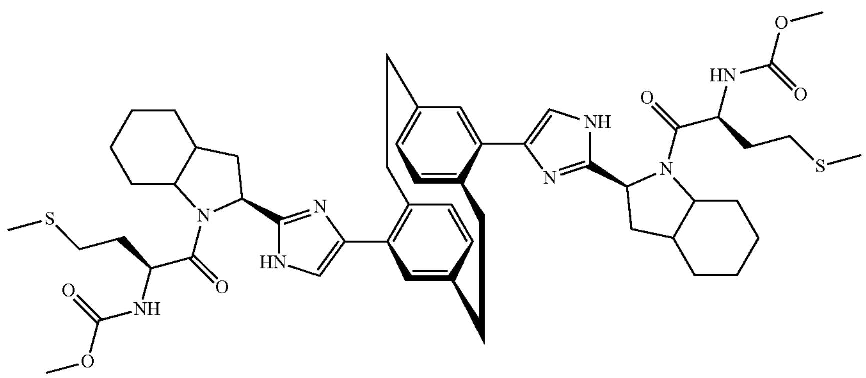 | | | | | |

| No. | Structure | EC50 (μM) NS5A1b | NS5A1b | HPLC LC method | MS |
|---|---|---|---|---|---|
| 143 | 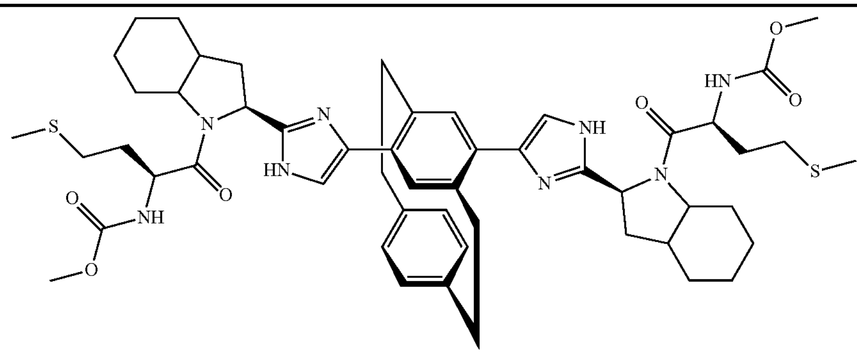 | | | | |
| 144 | 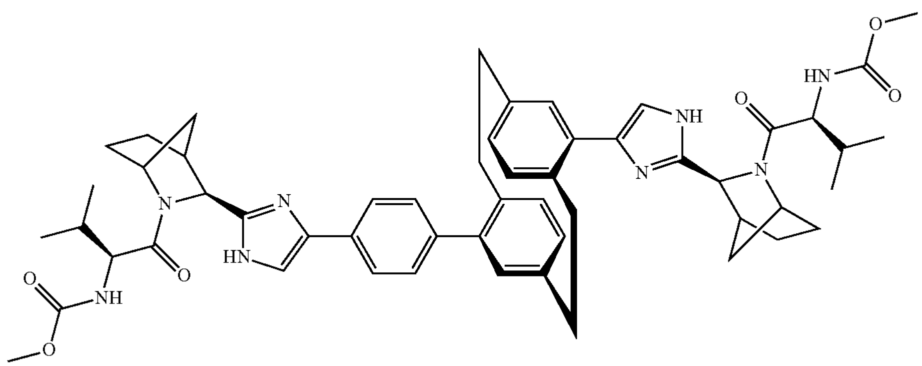 | | | | |

| No. | Structure | EC50 (μM) | | HPLC | |
|---|---|---|---|---|---|
| | | NS5A1b | NS5A1b | LC | method | MS |

145

146

-continued

| No. | Structure | EC50 (μM) NS5A1b | EC50 (μM) NS5A1b | LC | HPLC method | MS |
|---|---|---|---|---|---|---|
| 147 | 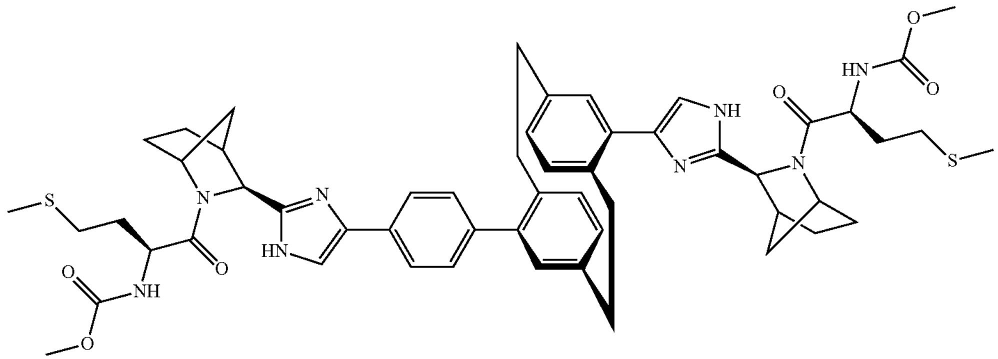 | | | | | |
| 148 | 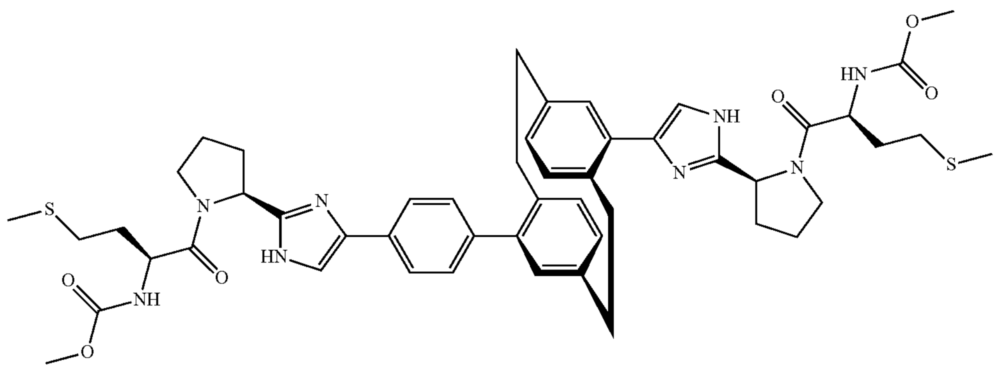 | | | | | |

| No. | Structure | EC50 (μM) NS5A1b | EC50 (μM) NS5A1b | LC | HPLC method | MS |
|---|---|---|---|---|---|---|
| 149 | 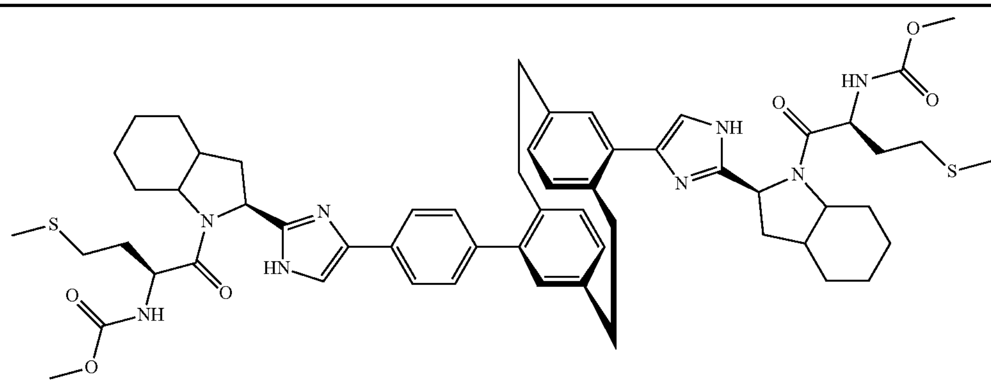 | | | | | |
| 150 | 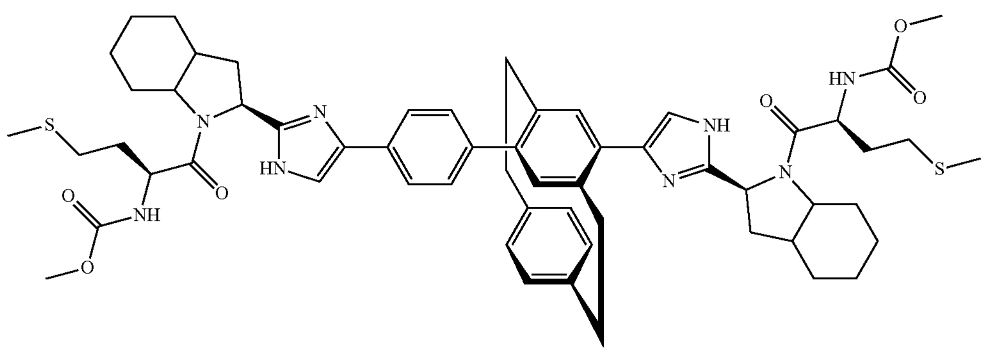 | | | | | |

| No. | Structure | EC50 (μM) NS5A1b | EC50 (μM) NS5A1b | HPLC LC | HPLC method | MS |
|---|---|---|---|---|---|---|
| 151 | 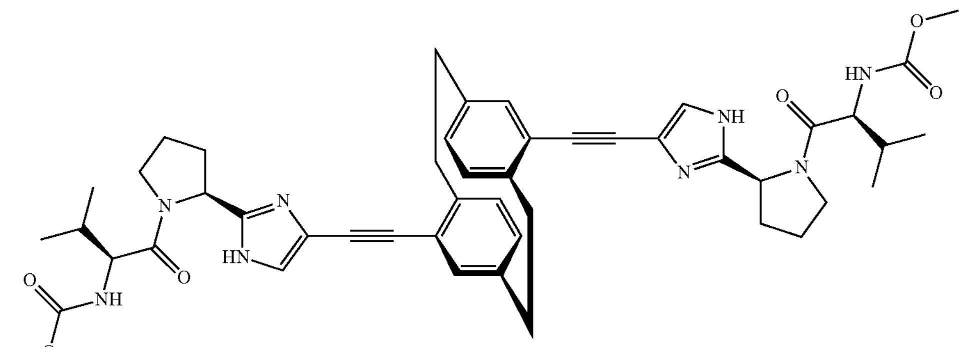 | | | | | |
| 152 | 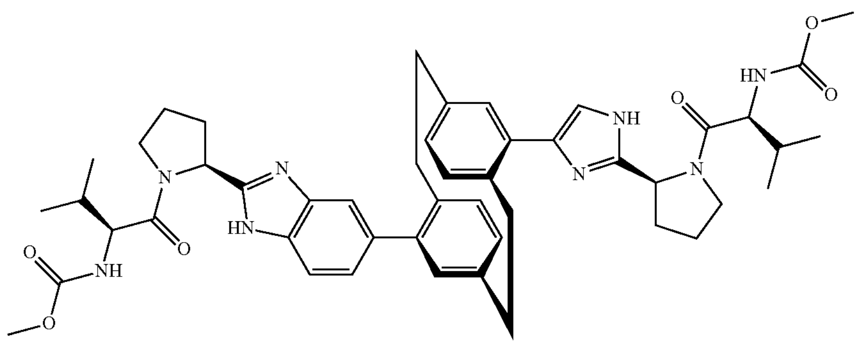 | | | | | |

-continued

| No. | Structure | EC50 (μM) | | HPLC | |
| --- | --- | --- | --- | --- | --- |
| | | NS5A1b | NS5A1b | LC | method | MS |
| 153 | | | | | | |
| 154 | | | | | | |

-continued

| No. | Structure | EC50 (μM) NS5A1b | EC50 (μM) NS5A1b | HPLC LC method | MS |
|---|---|---|---|---|---|
| 155 | 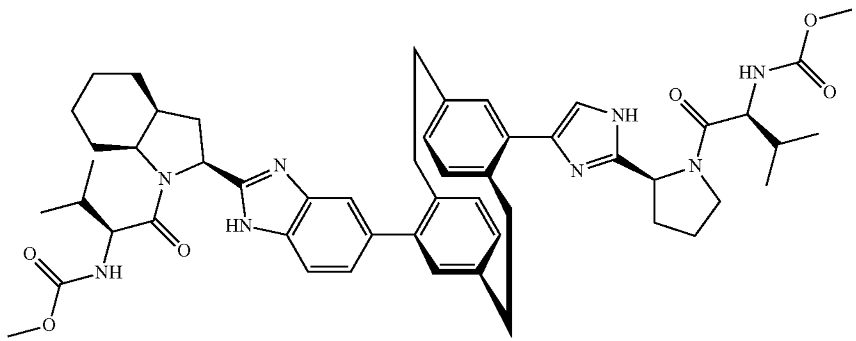 | | | | |
| 156 | 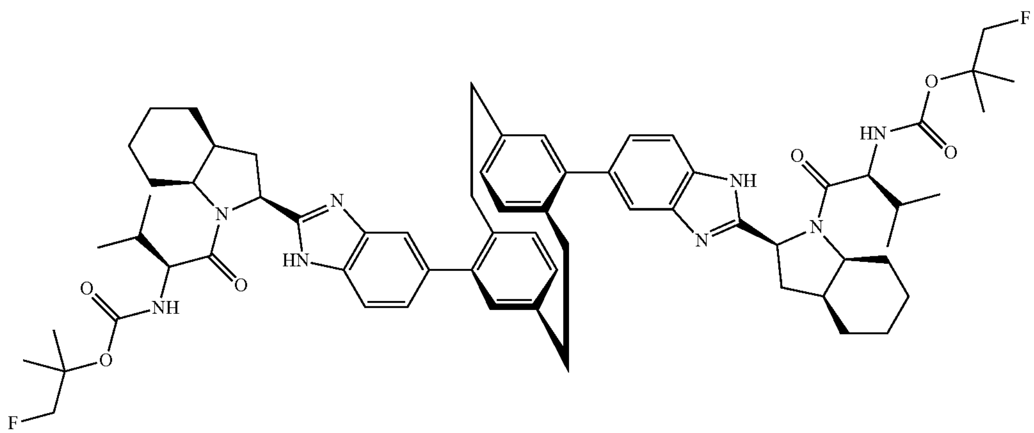 | | | | |

Example 9

Assay for Identifying Compounds which Inhibit HCV Replication

Compounds claimed herein are tested for the ability to inhibit viral replication of the Hepatitis C replicon in cultured cells in which the HCV replicon construct has been incorporated. The HCV replicon system was described by Bartenschlager, et. al (Science, 285, pp. 110-113 (1999)). The replicon system is predictive of in vivo anti-HCV activity; compounds that are active in humans uniformly evidence activity in the replicon assay.

In this assay HCV replicon containing cells are treated with different concentrations of the test compound to ascertain the ability of the test compound to suppress replication of the HCV replicon. As a positive control, HCV replicon-containing cells are treated with different concentrations of interferon alpha, a known inhibitor of HCV replication. The replicon assay system includes Neomycin Phosphotransferase (NPT) as a component of the replicon itself in order to detect the transcription of replicon gene products in the host cell. Cells in which the HCV replicon is actively replicating have high levels of NPT; the level of NPT is proportional to HCV replication. Cells in which the HCV replicon is not replicating also have low levels of NPT and thus do not survive when treated with Neomycin. The NPT level of each sample is measured using a captured ELISA.

A protocol for testing compounds for the ability to inhibit viral replication of the Hepatitis C replicon cultured cells in which the replicon construct has been incorporated, follows.

9A. HCV Replicon and Replicon Expression

The HCV genome consists of a single ORF that encodes a 3000 amino acid polyprotein. The ORF is flanked on the 5' side by an untranslated region that serves as an internal ribosome entry site (IRES) and at the 3' side by a highly conserved sequence necessary for viral replication (3'-NTR). The structural proteins, necessary for viral infection, are located near the 5' end of the ORF. The non-structural proteins, designated NS2 to NS5B comprise the remainder of the ORF.

The HCV replicon contains, 5'-3', the HCV-IRES, the neomycin phosphotransferase (neo) gene, the IRES of encephalomyocarditis virus, which directs translation of HCV sequences NS3 to NS5B, and the 3'-NTR. The sequence of the HCV replicon has been deposited in GenBank (Accession no. AJ242652).

The replicon is transfected into Huh-7 cells using standard methods such as electroporation.

9B. Cell Maintenance

The equipment and materials include, but are not limited to, Huh-7 HCV replicon-containing cells, maintenance media (DMEM (Dulbecco's modified Eagle media) supplemented with 10% FBS, L-glutamine, non-essential amino acids, penicillin (100 units/nil), streptomycin (100 micrograms/nil), and 500 micrograms/ml of Geneticin (G418), screening media (DMEM supplemented with 10% FBS, L-glutamine, non-essential amino acids, penicillin (100 units/nil) and streptomycin (100 micrograms/nil)), 96 well tissue culture plates (flat bottom), 96 well plates (U bottom for drug dilution), Interferon alpha for positive control, fixation reagent (such as methanol: acetone), primary antibody (rabbit anti-NPTII), secondary antibody: Eu-N11, and enhancement solution.

HCV replicon-containing cells support high levels of viral RNA replicon replication when their density is suitable. Over-confluency causes decreased viral RNA replication. Therefore, cells must be kept growing in log phase in the presence of 500 micrograms/ml of G418. Generally, cells should be passed twice a week at 1: 4-6 dilution. Cell maintenance is conducted as follows:

HCV replicon-containing cells are examined under a microscope to ensure that cells growing well. Cells are rinsed once with PBS and 2 ml trypsin is added. The cell/trypsin mixture is incubated at 37° C. in a $CO_2$ incubator for 3-5 minutes. After incubation 10 ml of complete media is added to stop the trypsinization reaction. Cells are blown gently, put into a 15 ml tube, and spun at 1200 rpm for 4 minutes. The trypsin/medium solution is removed. Medium (5 ml) is added and the cells are mixed carefully. The cells are counted.

The cells are then seeded onto 96-well plates at a density of 6000-7500 cells/100 microliters/well (6-7.5×105 cells/10 ml/plate). The plates are then incubated at 37° C. in a 5% CO2 incubator.

Cells are examined under a microscope approximated 24 hours after seeding and prior to adding drugs. If counting and dilution were performed correctly, cells are 60-70% confluent and nearly all cells should attach and spread evenly in the well.

6C. Treatment of HCV-Replicon Containing Cells with Test Compound

HCV replicon-containing cells are rinsed with once PBS once; 2 mls of trypsin are then added. Cells are incubated at 37° C. in a 5% CO2 incubator for 3-5 minutes. 10 mls of complete medium is added to stop the reaction. Cells are blown gently, put into a 15 ml tube, and spun at 1200 rpm for four minutes. The trypsin/medium solution is removed and 5 mls of medium (500 ml DMEM (high glucose)) from BRL catalog #12430-054; 50 mls 10% FBS, 5% Geneticin G418 (50 mg/ml, BRL catalog #10131-035), 5 ml MEM non-essential amino acids (100×BRL #11140-050) and 5 ml pen-strep (BRL #15140-148) is added. The cells and media are mixed carefully Cells are plated with screening medium (500 ml DMEM (BRL #21063-029), 50 ml FBS (BRL #10082-147) and 5 ml MEM non-essential amino acid (BRL #11140-050) at 6000-7500 fcells/100 μl/well of 96 well plate (6-7.5×105 cells/10 ml/plate). Plates are placed into 37° C. 5% $CO_2$ incubator overnight.

4D. Assay

The following morning, drugs (test compounds or interferon alpha) are diluted in 96 well U bottom plates with media or DMSO/media, depending on the final concentration chosen for screening. Generally for 6 concentrations of each test compounds ranging from 10 micromolar to 0.03 micromolar are applied. 100 μl of the test compound dilution is placed in wells of the 96 well plate containing the HCV replicon cells. Media without drug is added to some wells as a negative controls. DMSO is known to affect cell growth. Therefore, if drugs diluted in DMSO are used, all wells, including negative control (media only) and positive control (interferon alpha) wells, must contain the same concentration of DMSO, for single dose screening. The plates are incubated at 37° C. in a humidified 5% CO2 environment for three days.

On day four, the NTPII assay is quantitated. The medium is poured from the plates and the plates are washed once in 200 μl of PBS. The PBS is then decanted and the plates tapped in a paper towel to remove any remaining PBS. Cells are fixed in situ with 100 μl/well of pre-cooled (−20° C.) methanol:acetone (1:1) and the plates are placed at −20° C. for 30 minutes.

The fixing solution is poured from the plates and the plates allowed to air-dry completely (approximately one hour). The appearance of the dried cell layer is recorded and the density of the cells in the toxic wells is scored with the naked eye. Alternatively cell viability may be assessed using the MTS assay described below.

The wells are blocked with 200 µl of blocking solution (10% FBS; 3% NGS in PBS) for 30 minutes at room temperature. The blocking solution is removed and 100 µl of rabbit anti-NPTII diluted 1:1000 in blocking solution is added to each well. The plates are then incubated 45-60 minutes at room temperature. After incubation, wells are washed six times with PBS-0.05% Tween-20 solution. 100 µl of 1:15,000 diluted Europium (EU)-conjugated goat anti-rabbit in blocking buffer is added to each well and incubated at room temperature for 30-45 minutes. The plates are washed again and 100 µl of enhancement solution (Perkin Elmer #4001-0010) is added to each well. Each plate is shaken (approx. 30 rpm) in a plate shaker for three minutes. 95 µl is transferred from each well to a black plate; the EU signal is quantitated in a Perkin-Elmer VICTOR plate reader (EU-Lance).

When tested in this assay Compounds 11, 16, 25, 33, 38, 39, and 40 exhibit EC50 values of about 10 micromolar or less.

Example 10

Cytotoxicity Assays

To insure that the decrease in replicon replication is due to compound activity against the HCV replicon rather than nonspecific toxicity assays are used to quantitate compound cytotoxicity.

10A. Cellular Protein Albumin Assay for Cytotoxicity

Cellular protein albumin measurements provide one marker of cytotoxicity. The protein levels obtained from cellular albumin assays may also be used to provide a normalization reference for antiviral activity of compounds.

In the protein albumin assay HCV replicon-containing cells are treated for three days with different concentrations of helioxanthin; a compound that is known to be cytotoxic at high concentrations. The cells are lysed and the cell lysate used to bind plate-bound goat anti-albumin antibody at room temperature (25° C. to 28° C.) for 3 hours. The plate is then washed 6 times with 1×PBS. After washing away the unbound proteins, mouse monoclonal anti-human serum albumin is applied to bind the albumin on the plate. The complex is then detected using phosphatase-labeled anti-mouse IgG as a second antibody.

10B. MTS Assay for Cytotoxicity

Cell viability may also be determined by CELLTITER 96 AQUEOUS ONE Solution Cell Proliferation Assay (Promega, Madison Wis.), a colorimetric assay for determining the number of viable cells. In this method, before fixing the cells, 10-20 µl MTS reagent is added to each well according to manufacturer's instructions, plates are incubated at 37° C. and read at OD 490 nm. During the incubation period living cells covert the MTS reagent to a formazan product which absorbs at 490 nm. Thus the 490 nm absorbance is directly proportional to the number of living cells in culture.

A direct comparison of the Cellular Albumin and MTS methods for determining cytotoxicity may be obtained as follows: Cells are treated with different concentrations of test compound or Helioxanthin for a three day-period. Prior to lysis for detection albumin as described above, the MTS reagent is added according to manufacturer's instruction to each well and incubate at 37° C. and read at OD 490 nm. The cellular albumin quantitation is then performed as described above.

What is claimed is:

1. A compound of the formula:

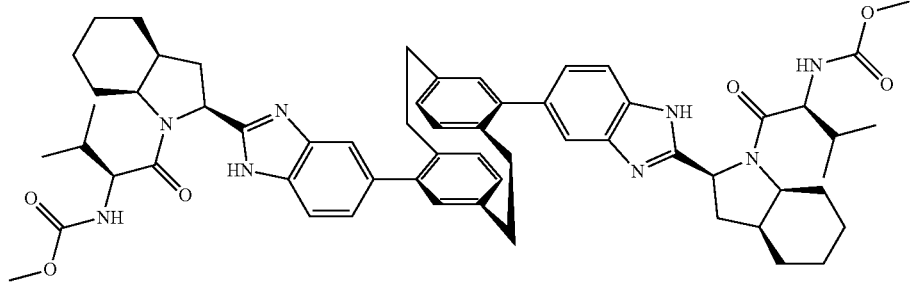

2. A pharmaceutical composition comprising an effective amount of a compound of the formula:

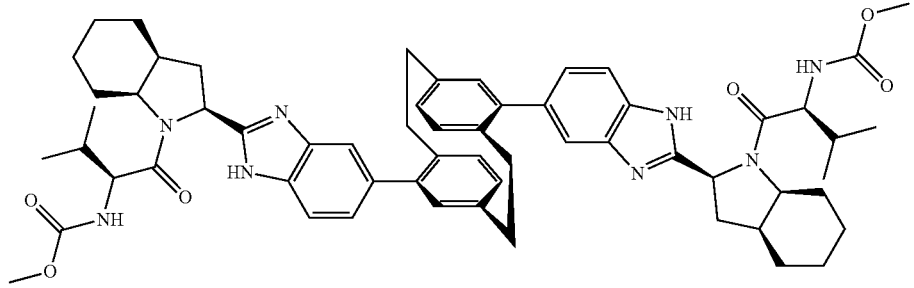

to treat HCV in a patient diagnosed with HCV or its pharmaceutically acceptable salt, further comprising an additional active agent, in a pharmaceutically acceptable carrier.

3. The pharmaceutical composition of claim 2, wherein the additional active agent is a protease inhibitor.

4. The pharmaceutical composition of claim 2, wherein the additional active agent is a nucleoside analog.

5. The pharmaceutical composition of claim 2, wherein the additional active agent is a NS5a inhibitor.

6. The pharmaceutical composition of claim 2, wherein the additional active agent is a NS5b inhibitor.

7. The pharmaceutical composition of claim 2, wherein the additional active agent is a NS4a inhibitor.

8. The pharmaceutical composition of claim 2, wherein the additional active agent is a NS4b inhibitor.

9. The pharmaceutical composition of claim 2, wherein the additional active agent is a polymerase inhibitor.

10. The pharmaceutical composition of claim 2, wherein the additional active agent is a NS3a inhibitor.

11. The pharmaceutical composition of claim 2, wherein the additional active agent is an immunomodulatory compound.

12. The pharmaceutical composition of claim 2, in an oral dosage form.

13. The pharmaceutical composition of claim 3, in an oral dosage form.

14. The pharmaceutical composition of claim 4, in an oral dosage form.

15. The pharmaceutical composition of claim 5, in an oral dosage form.

16. The pharmaceutical composition of claim 6, in an oral dosage form.

17. The pharmaceutical composition of claim 7, in an oral dosage form.

18. The pharmaceutical composition of claim 8, in an oral dosage form.

19. The pharmaceutical composition of claim 9, in an oral dosage form.

20. The pharmaceutical composition of claim 10, in an oral dosage form.

21. The pharmaceutical composition of claim 11, in an oral dosage form.

22. The pharmaceutical composition of claim 2, in a tablet.

23. The pharmaceutical composition of claim 3, in a tablet.

24. The pharmaceutical composition of claim 4, in a tablet.

25. The pharmaceutical composition of claim 5, in a tablet.

26. The pharmaceutical composition of claim 6, in a tablet.

27. The pharmaceutical composition of claim 7, in a tablet.

28. The pharmaceutical composition of claim 8, in a tablet.

29. The pharmaceutical composition of claim 9, in a tablet.

30. The pharmaceutical composition of claim 10, in a tablet.

31. The pharmaceutical composition of claim 11, in a tablet.

32. A method to treat HCV in a patient diagnosed with HCV with a pharmaceutical composition comprising a compound of the formula:

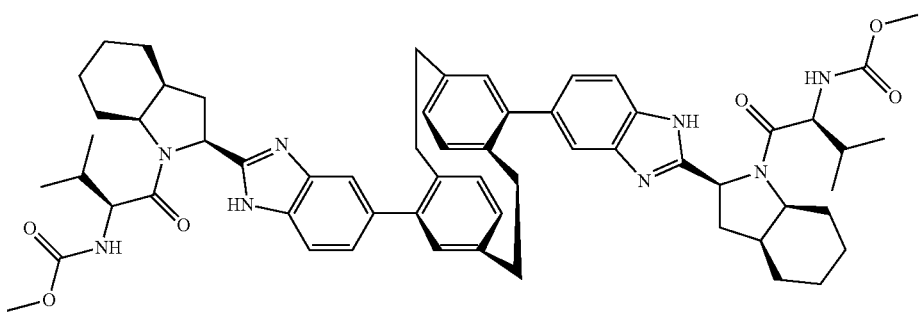

and or its pharmaceutically acceptable salt, and further comprising an additional active agent optionally in a pharmaceutically acceptable carrier.

33. The method of claim 32, wherein the additional active agent is a protease inhibitor.

34. The method of claim 32, wherein the additional active agent is a nucleoside analog.

35. The method of claim 32, wherein the additional active agent is a NS5a inhibitor.

36. The method of claim 32, wherein the additional active agent is a NS5b inhibitor.

37. The method of claim 32, wherein the additional active agent is a NS4a inhibitor.

38. The method of claim 32, wherein the additional active agent is a NS4b inhibitor.

39. The method of claim 32, wherein the additional active agent is a polymerase inhibitor.

40. The method of claim 32, wherein the additional active agent is a NS3a inhibitor.

41. The method of claim 32, wherein the additional active agent is an immunomodulatory compound.

* * * * *